(12) United States Patent
Fuchigami et al.

(10) Patent No.: US 7,746,452 B2
(45) Date of Patent: Jun. 29, 2010

(54) PORTABLE METER TO MEASURE CHLOROPHYLL, NITROGEN AND WATER AND METHODS

(75) Inventors: Leslie H. Fuchigami, Corvallis, OR (US); Pinghai Ding, Burnaby (CA); Guy E. Barnes, Jr., Hillsboro, OR (US)

(73) Assignee: State of Oregon acting by and through the State Board of Higher Education on behalf of Oregon State University, Corvallis, OR (US)

( * ) Notice: Subject to any disclaimer, the term of this patent is extended or adjusted under 35 U.S.C. 154(b) by 77 days.

(21) Appl. No.: 12/089,902

(22) PCT Filed: Nov. 21, 2006

(86) PCT No.: PCT/US2006/045350

§ 371 (c)(1),
(2), (4) Date: Apr. 10, 2008

(87) PCT Pub. No.: WO2007/062196

PCT Pub. Date: May 31, 2007

(65) Prior Publication Data

US 2008/0239293 A1   Oct. 2, 2008

Related U.S. Application Data

(60) Provisional application No. 60/738,752, filed on Nov. 21, 2005, provisional application No. 60/742,217, filed on Dec. 2, 2005.

(51) Int. Cl.
*G01N 21/00* (2006.01)

(52) U.S. Cl. ............................. 356/73; 356/51; 356/420
(58) Field of Classification Search ................ 356/73
See application file for complete search history.

(56) References Cited

U.S. PATENT DOCUMENTS

| 4,295,042 A | * | 10/1981 | Watanabe et al. ............ 250/226 |
| 4,986,665 A | * | 1/1991 | Yamanishi et al. ........... 356/402 |
| 5,296,702 A | | 3/1994 | Beck et al. |
| 5,424,840 A | | 6/1995 | Moore et al. |
| 6,020,587 A | * | 2/2000 | Spiering et al. ......... 250/339.11 |
| 2002/0011567 A1 | | 1/2002 | Ozanich |

FOREIGN PATENT DOCUMENTS

JP   2000-88747   *   3/2000

OTHER PUBLICATIONS

International Search Report and Written Opinion for PCT/US2006/045350, filed Nov. 21, 2006 (mailed Jul. 31, 2007).

* cited by examiner

*Primary Examiner*—F. L Evans
(74) *Attorney, Agent, or Firm*—Klarquist Sparkman, LLP

(57) ABSTRACT

Methods for determining chlorophyll content comprise providing a sample, subjecting the sample to light at a first wavelength and detecting a first wavelength response, subjecting the sample to light at a second wavelength and detecting a second wavelength response, and calculating a chlorophyll content of the sample based on at least the first wavelength response and the second wavelength response. Optional approaches include detecting the nitrogen content and/or water content of the sample. Associated apparatus for determining chlorophyll content, which may comprise a handheld device, is also disclosed.

50 Claims, 34 Drawing Sheets

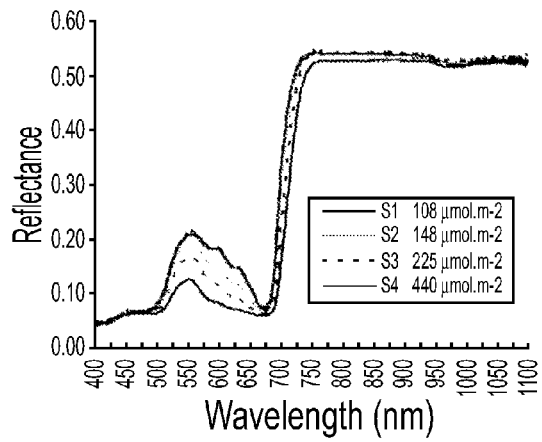
FIG. 1A
FIG. 1B
FIG. 1C
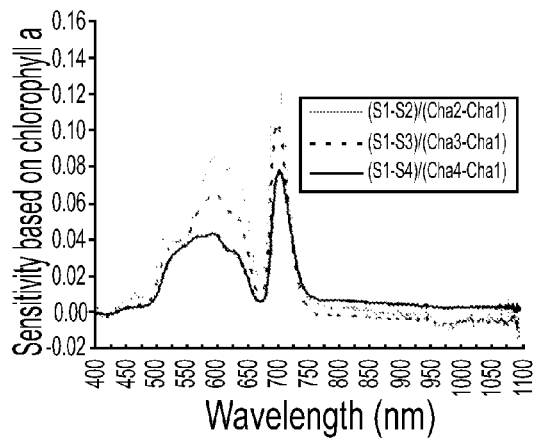
FIG. 1D
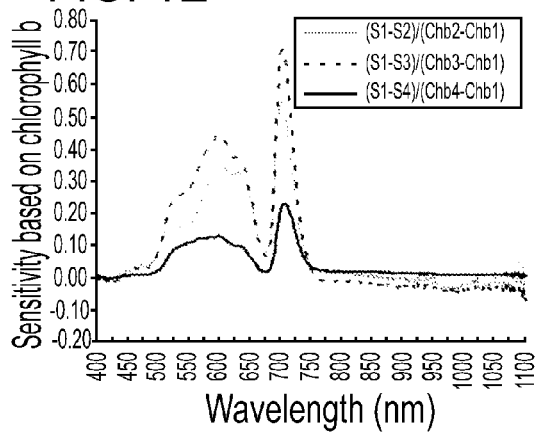
FIG. 1E
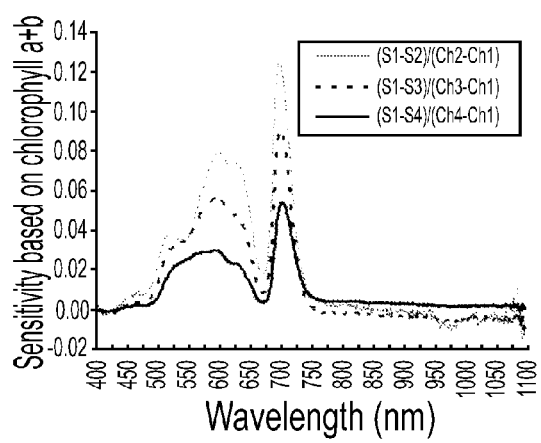
FIG. 1F

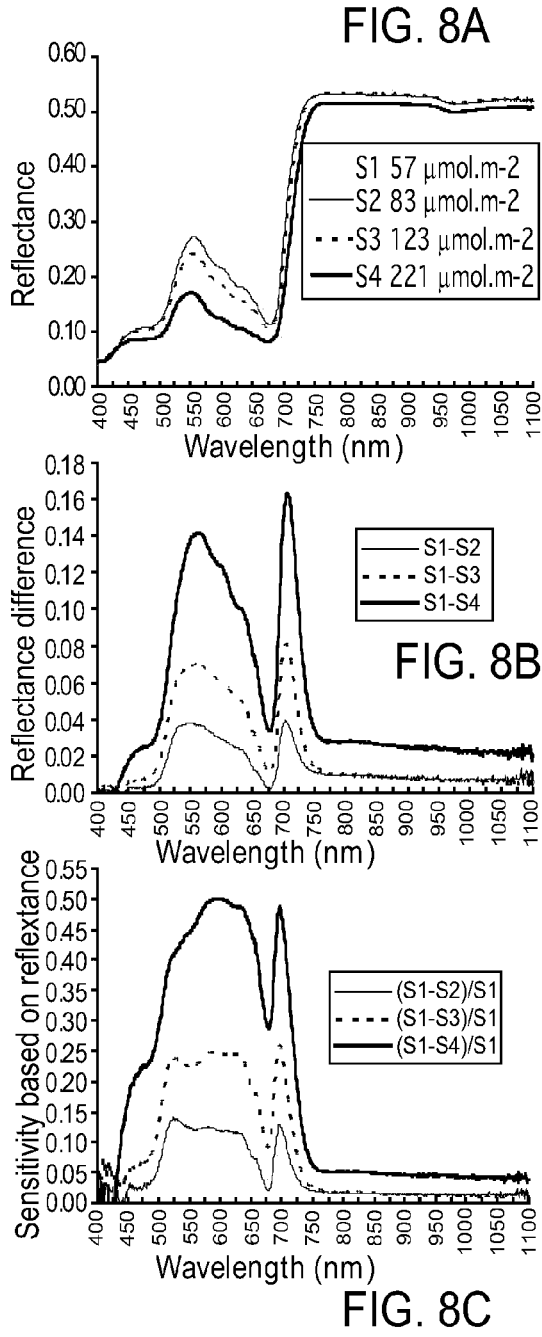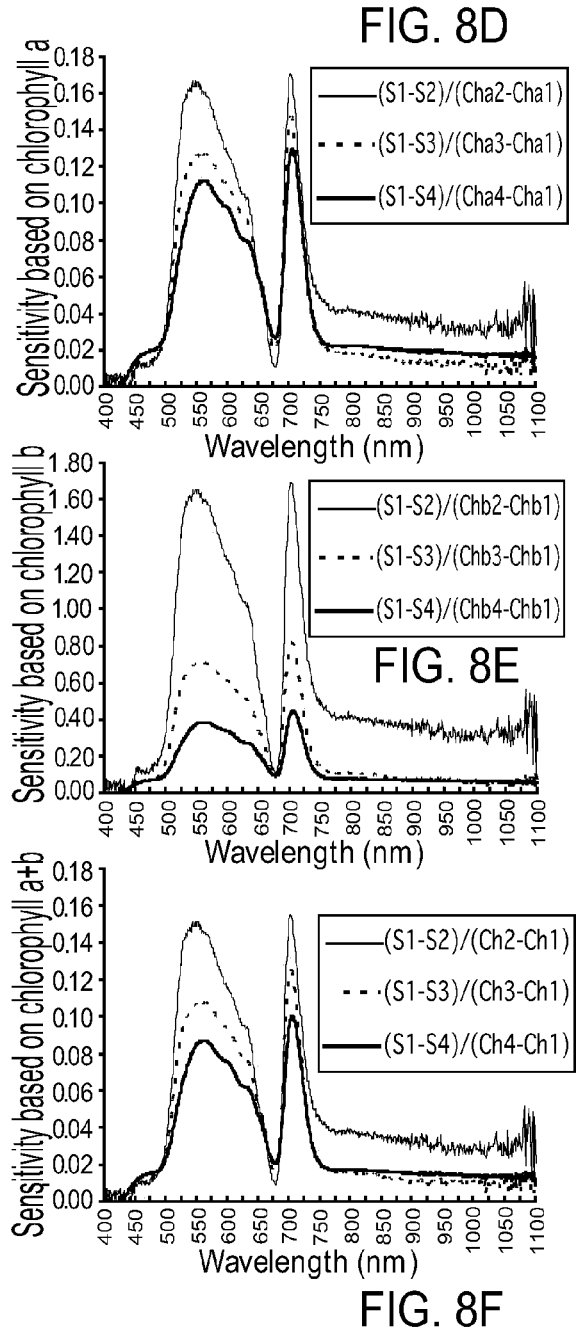
FIG. 8A, FIG. 8B, FIG. 8C, FIG. 8D, FIG. 8E, FIG. 8F

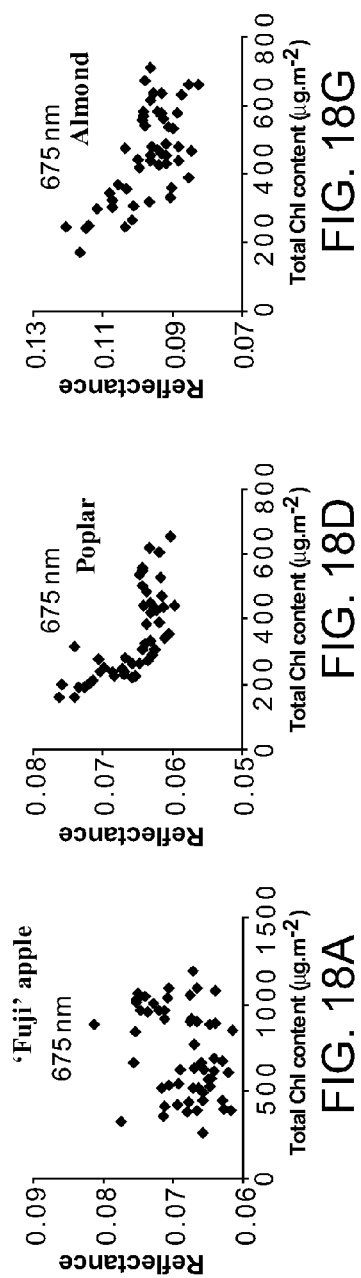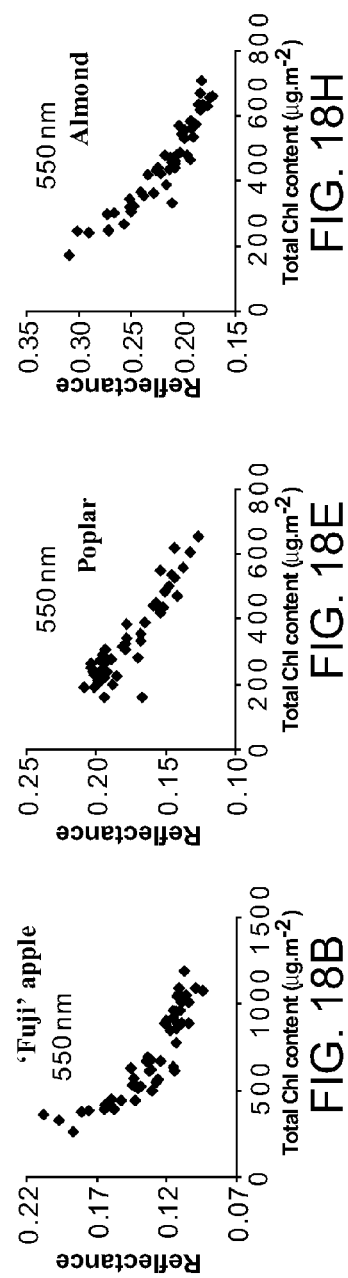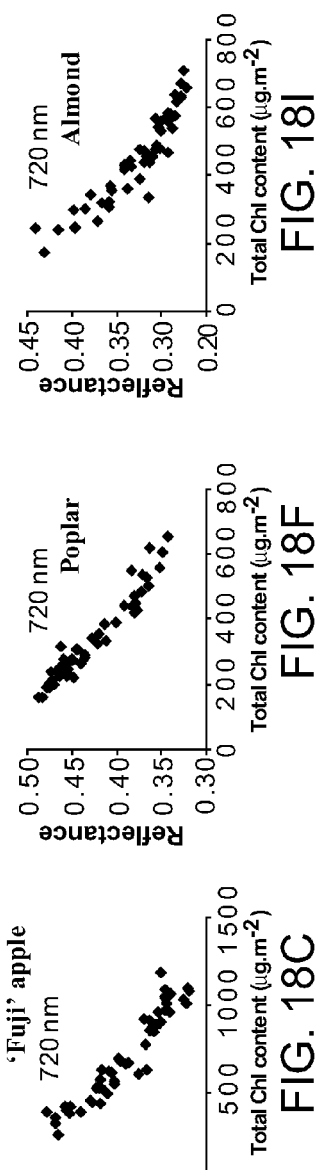
FIG. 18A – FIG. 18I

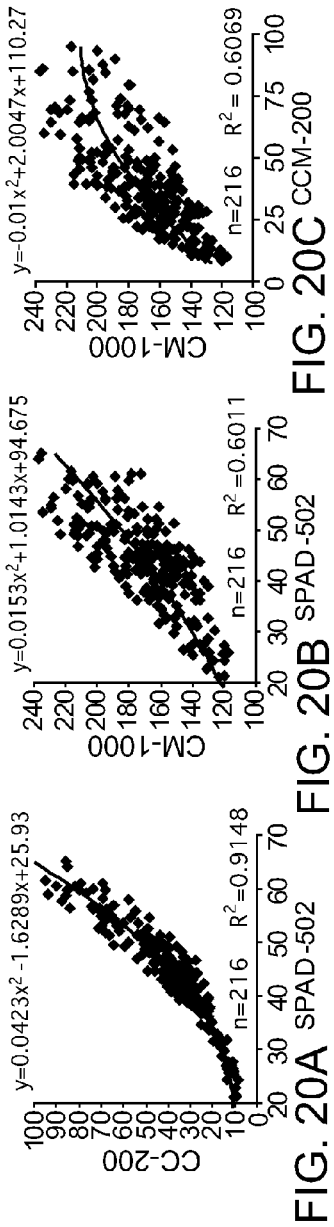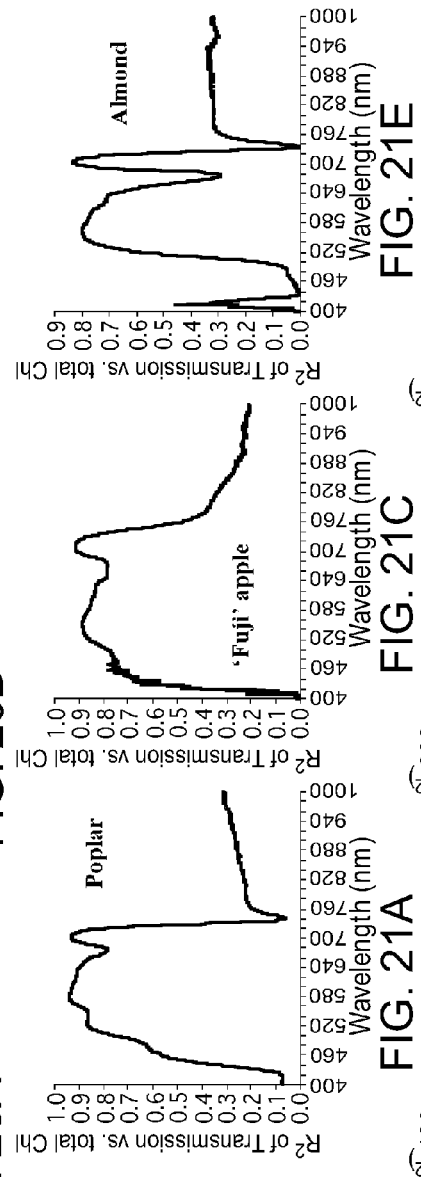
FIG. 20A  FIG. 20B  FIG. 20C
FIG. 21A  FIG. 21B  FIG. 21C  FIG. 21D  FIG. 21E  FIG. 21F

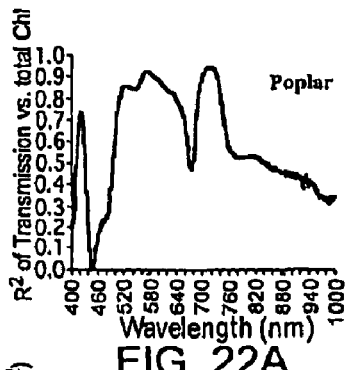
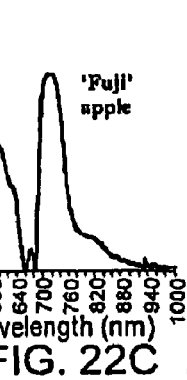
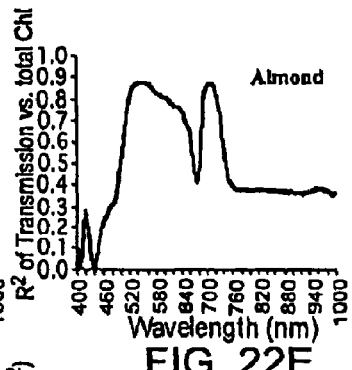
FIG. 22A  FIG. 22C  FIG. 22E
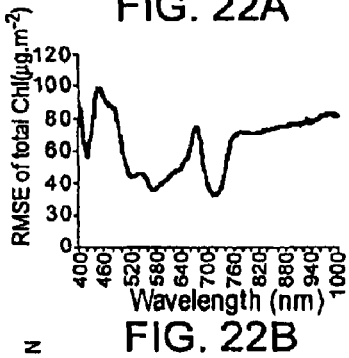
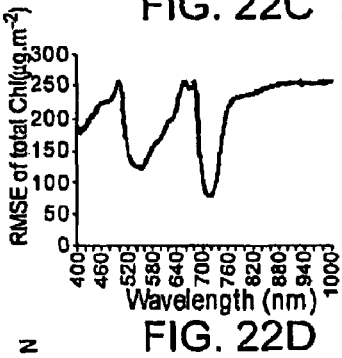
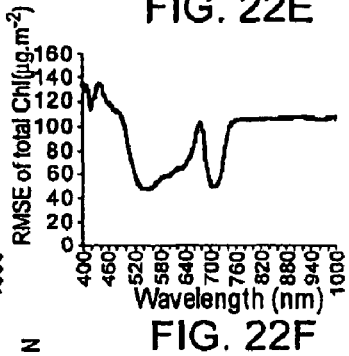
FIG. 22B  FIG. 22D  FIG. 22F
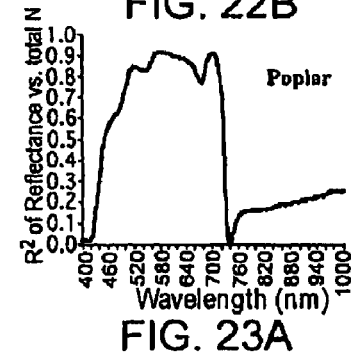
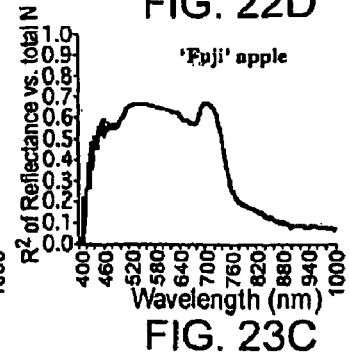
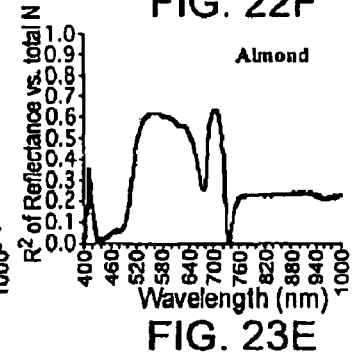
FIG. 23A  FIG. 23C  FIG. 23E
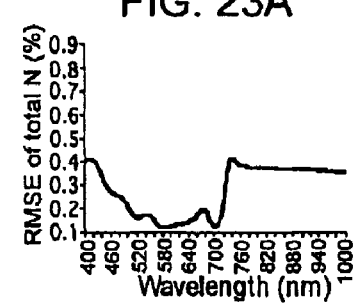
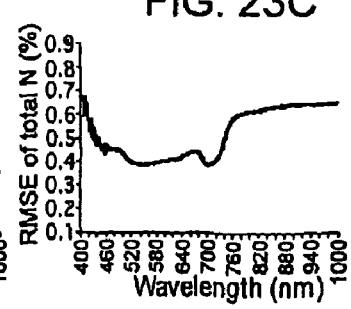
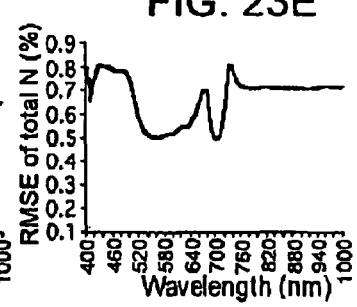
FIG. 23B  FIG. 23D  FIG. 23F

PORTABLE METER TO MEASURE CHLOROPHYLL, NITROGEN AND WATER AND METHODS

Cross Reference to Related Applications

This is the U.S. National Stage of International Application No. PCT/US2006/045350, filed Nov. 21, 2006, which was published in English under PCT Article 21(2), which in turn claims the benefit of U.S. Provisional Application No. 60/738,752, filed Nov. 21, 2005 and U.S. Provisional Application No. 60/742,217, filed Dec. 2, 2005. These prior applications are incorporated herein in their entirety.

BACKGROUND

Measuring chlorophyll and plant samples, such as leaves of fruit plants is important in determining that the plant has proper conditions (e.g., habitat, nutrients, lighting, etc.) for optimum growth.

It is known to conduct laboratory chemical analysis of plant samples to determine chlorophyll content. Such analysis involves the steps of collecting samples, drying and grinding the samples, performing chemical analysis of the samples and interpreting the results. Chemical analysis, however, is time consuming, expensive and requires professional expertise. In addition, such analysis is usually not available in time to adjust growing conditions (e.g., fertilization) for a current year's crop.

Some efforts have been made to provide portable devices or meters to provide an indication of chlorophyll content in a sample. The SPAD meter (produced by Minolta of Japan) is widely used by growers and researchers throughout the world. The SPAD meter has a cost of about $1,500. The SPAD-502 weighs 225 grams, has a 0.06 $cm^2$ measurement area and calculates an index in SPAD units based on absorbance at 650 nm and 950 nm. The claimed accuracy of the SPAD-502 is +/−1.0 SPAD units.

The Chlorophyll Content Meter-200 (CCM-200, produced by Optiscience) costs about $1,000, weighs 180 grams, has a 0.71 $cm^2$ measurement area and calculates a chlorophyll content index (CCI) based on absorbance measurements at 660 nm and 940 nm. The claimed accuracy of the CCM-200 is +/−1.0 CCI units.

The Chlorophyll Meter-1000 (CM-1000, produced by Spectrum Technology, Inc.) costs $2,500. The CM-1000 weighs 692 grams and calculates an index in CM-1000 units based on reflectance at 700 nm and 840 nm. The recommended sampling distance for the CM-1000 is 28.4 to 183.0 cm with a corresponding sampling scope of 1.10 to 18.8 cm in diameter outlined with the high powered lasers.

Another meter, the CL-01 Chlorophyll Content Meter, weighs 250 grams, can measure leaf samples up to a maximum of 12.7 cm wide and calculates a chlorophyll index based on absorbance at 620 nm and 940 nm.

These conventional meters, however, do not provide high accuracy results. In addition, each of these meters gives an indication of chlorophyll content based on a different index. None of these meters directly gives a chlorophyll content result or a nitrogen content result. Also, none of these meters conveys its results in connection with a real world location, such that a user surveying an entire field of a particular crop could correlate trends in chlorophyll values with particular locations of the samples, among other uses for such information.

SUMMARY

Described below are embodiments of methods for determining chlorophyll content and associated devices that overcome problems with prior art approaches.

According to one embodiment, a method for determining chlorophyll content comprises providing a sample, subjecting the sample to light at a first wavelength and detecting a first wavelength response, subjecting the sample to light at a second wavelength and detecting a second wavelength response, and calculating a chlorophyll content of the sample based on at least the first wavelength response and the second wavelength response.

The method may include subjecting the sample to light at a third wavelength and detecting a third wavelength response, and/or subjecting the sample to light at a fourth wavelength and detecting a fourth wavelength response. The calculation of chlorophyll content of the sample would then be based on the third and/or fourth wavelength responses.

The method can comprise providing a handheld device such that the steps of subjecting the sample to light at a first wavelength, subjecting the sample to light at a second wavelength and calculating a chlorophyll content of the sample are executed with the handheld device.

Subjecting the sample to light at a first wavelength can comprise subjecting the sample to light at a wavelength of about 520 nm to about 580 nm. Subjecting the sample to light at a first wavelength can comprise subjecting the sample to light at a wavelength selected to indicate chlorophyll content.

Subjecting the sample to light at a second wavelength can comprise subjecting the sample to light at a wavelength of about 690 nm to about 740 nm. Subjecting the sample to light at a second wavelength can comprise subjecting the sample to light at a far-red wavelength selected to indicate nitrogen content.

Subjecting the sample to light at a third wavelength can comprise subjecting the sample to light at a wavelength of about 800 nm to about 1100 nm. Subjecting the sample to light at a third wavelength can comprise subjecting the sample to light at an infrared wavelength selected to account for at least thickness and/or texture of the sample.

Subjecting the sample to light at a fourth wavelength can comprise subjecting the sample to light at a wavelength of about 1420 nm to about 1510 nm. Subjecting the sample to light at a fourth wavelength can comprise subjecting the sample light at an infrared wavelength selected to indicate water content.

The method can comprise storing position information regarding the sample's location. Storing position information regarding the sample's location can comprise storing GPS coordinates representing the sample's location.

Subjecting the sample to light at a first wavelength and subjecting the sample to light at a second wavelength can comprise causing light to impinge upon the sample, wherein detecting a first wavelength response and detecting a second wavelength response comprise measuring reflectance from the sample.

Subjecting the sample to light at a first wavelength and subjecting the sample to light at a second wavelength can comprise causing light to impinge upon the sample, wherein detecting a first wavelength and detecting a second wavelength response comprise measuring transmittance through the sample.

The method can comprise determining the water content of the sample, wherein the water content is a factor used in calculating a chlorophyll content of the sample. The method can comprise determining the sample's exterior characteristics, wherein the exterior characteristics are a factor in calculating a chlorophyll content of the sample.

A device for determining chlorophyll content can comprise a sample receiving area, a light source, a photodetector and a microprocessor. The sample receiving area is configured to accommodate a sample during testing. The light source is positioned adjacent the sample receiving area and is operable to subject a sample in the sample receiving area to at least two different wavelengths of light. The photodetector is operatively arranged adjacent the sample receiving area and configured to detect responses to the at least two different wavelengths of light. The microprocessor is connected to the light source and to the photodetector. The microprocessor controls the light source and the photodetector, and calculates a chlorophyll value of a sample based on at least the responses to the at least two different wavelengths of light.

The device can comprise a lens positioned to focus light from the light source on a sample in the sample receiving area. The light source can comprise at least one light emitting diode (LED). The light source can comprise at least one LED capable of generating the at least two different wavelengths of light.

In some embodiments, the light source is capable of generating light at four different wavelengths, including a first wavelength of about 520 nm to about 580 nm, a second wavelength of about 690 nm to about 740 nm, a third wavelength of about 800 nm to about 1100 nm and a fourth wavelength of about 1420 nm to about 1510 nm.

The device can comprise a lens positioned between the light source and the sample receiving area, the lens defining an optical axis extending toward the sample receiving area, wherein the light source comprising multiple LED elements, and wherein an LED element capable of generating light at the first wavelength is spaced farther from the optical axis than an LED element capable of generating light at a third wavelength.

The photodetector can be capable of sensing light at the first wavelength and at the second wavelength. The photodetector can comprise a Si/PBS photodetector.

The device can be a handheld device. The device can comprise a GPS receiver connected to the microprocessor, the GPS receiver being capable of determining a current position.

The device can comprise a personal digital assistant connected to the microcontroller, the personal digital assistant having a display, an input device and a memory in which a program for interacting with the device is stored, the display and input device being used to control the operation of the device. The device can comprise a GPS receiver connected to the microcontroller wherein the personal digital assistant is operable to display selected position information relative to a background map.

The device may comprise a biasing circuit and an amplifier. The device may be portable and include a source of DC power. The device may be configured to determine chlorophyll content without harming sample.

According to other methods, calculating the chlorophyll content comprises obtaining a baseline transmittance value for each wavelength of light to which the sample is subjected, obtaining a measured transmittance value for each wavelength of light, and computing at least one index based on the measured transmittance values and the actual transmittance values.

The method may comprise computing a polynomial equation based on the at least one index. The polynomial equation may comprise a quadratic equation. The method may comprise computing an exponential equation in which the exponent is the index. The method may comprise computing a power equation in which the index is raised to a power.

The method may comprise comparing the at least one index to corresponding stored values for a particular plant and outputting a result. The stored values may be for a particular plant variety.

The baseline and measured transmittance values may be directly proportional to voltage values.

A first transmittance ratio may be equal to the measured transmittance at the first wavelength divided by the baseline transmittance at the first wavelength and the third transmittance ratio may be equal to the measured transmittance at the third wavelength divided by the baseline transmittance at the third wavelength. Computing at least one index can include computing a first index equal to the third transmittance ratio divided by the first transmittance ratio.

A second transmittance ratio can be equal to the measured transmittance at the second wavelength divided by the baseline transmittance at the second wavelength. Computing at least one index can include computing a second index equal to the third transmittance ratio divided by the second transmittance ratio.

Computing at least one index can include computing a third index equal to a quotient of the third transmittance ratio minus the first transmittance ratio divided by the third transmittance ratio plus the first transmittance ratio.

Computing at least one index can include computing a fourth index equal to a quotient of the third transmittance ratio minus the second transmittance ratio divided by the third transmittance ratio plus the second transmittance ratio. In the method, the at least one index can be a first index, and multiple indices can be computed, further comprising comparing each of the multiple indices to corresponding stored values, selecting one of the indices based on a predetermined criterion, and output results based on the selected one of the indices.

BRIEF DESCRIPTION OF DRAWINGS

FIGS. 1A-1F show graphs at each wavelength from about 300 to about 1100 nm in poplar leaves for original reflectance (A), coefficients of determination (B), RMSE of chlorophyll estimation (C), and wavelength sensitivity of chlorophylls (Ch a, Ch b and Ch a+b)) (D, E and F, respectively).

FIGS. 8A-8F show graphs of the reflectance spectrum (A), the reflectance difference (B), sensitivity based on reflectance (C), sensitivity based on Ch a (D), sensitivity based on Ch b (E) and sensitivity based on Ch a+Ch b (F) of four almond leaves with chlorophyll contents of 57, 83, 123 and 221 mol·m$^{-2}$, respectively.

FIGS. 18A-18I show graphs of the relationships between reflectance and total Chl at wavelengths of 550, 675 and 720 nm in the leaves of 'Fuji' apple, poplar and almond, respectively.

FIGS. 20A-20C show graphs of the relationship of indices between the SPAD-502 and the CCM-200 meters, between the SPAD-502 and the CM-1000 meters, and between the CCM-200 and the CCM-1000 meters, respectively, for 216 leaf samples (including 72 each for almond, 'Fuji' apple and poplar, with each point representing the mean of 5 measurements taken on an individual leaf).

FIGS. 21A-21F show graphs of the $R^2$ and RMSE of total Chl estimated by transmission in poplar, Fuji apple and almond leaves.

FIGS. 22A-22F show graphs of the $R^2$ and RMSE of total Chl estimated by reflectance in poplar, Fuji apple and almond leaves.

FIGS. 23A-23F show graphs of the $R^2$ and RMSE of total N estimated by transmission in poplar, Fuji apple and almond leaves.

FIGS. 25A-25C shows graphs of the effect of sampling distance on the CM-1000 index in measuring poplar leaves with chlorophyll contents of 480, 574 and 655 μg·m$^2$, respectively (the different letters indicate LSD test P<5%).

DETAILED DESCRIPTION

Part I: Overview and Summary

Figure 2A:
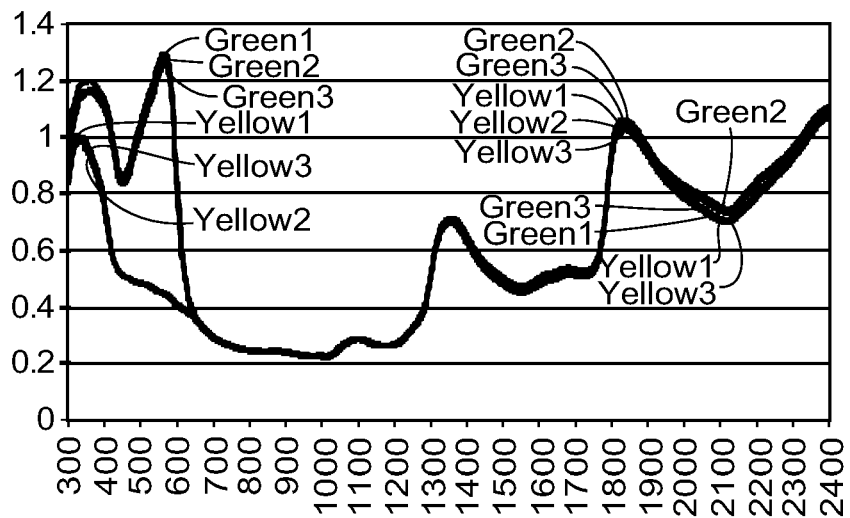
FIGS. 2A-2C show graphs of spectra of leaves with and without chlorophyll (A), and at different water contents (B and C).

This application relates to hand-held portable meters and associated methods which can accurately determine the chlorophyll, nitrogen, and water content in fresh plant leaves by measuring the optical transmission in multiple specific wavelength bands and using these transmission values in a predetermined, species-specific formula.

The spectral wavelength range for measuring chlorophyll and nitrogen is from 450 to 740 nm. However, the specific wavelengths showing high correlation to chlorophyll and nitrogen concentration are two narrow ranges from 550-570 nm and from 700-730 nm. Within these wavelengths bands the amount of light that will be transmitted (or reflected) will vary depending on the amount of chlorophyll and nitrogen present in the leaves. The spectral near-infrared (NIR) wavelength ranges for measuring water content in leaves are from 1400 nm to 1550 nm and from 1870 nm to 2100 nm. The best wavelength range for determining the water status of leaves is between 1420-1510 nm (peak 1450±30 nm) and 1900-2000 nm (peak 1940±30 nm). The amount of light transmitted (or reflected) in the two chlorophyll/nitrogen bands by the leaves also varies with the water content of the leaf.

The texture, thickness and density of the leaf also affects the transmission (or reflectance) of light. The optimum wavelength range for determining the influence of leaf texture, thickness and density is from 800 to 1120 nm where there is no spectral structure from the absorption peaks.

Methods for accurately determining chlorophyll, nitrogen and water content in plant leaves by using transmission (or reflectance) of light at these wavelengths are described.

Associated apparatus for measuring these quantities is also described. We have built two prototype hand-held instruments using light transmission and have tested these against accepted laboratory processes for determining the amounts of chlorophyll, nitrogen and water showing their high degree of accuracy. We are also testing a third prototype instrument using a Hewlett Packard personal data assistant (PDA) along with an add-on global positioning system (GPS) module for determining and recording precise sample locations in the field along with the measured data, and displaying these results in relation to each other. Such an instrument is in high demand by plant producers and researchers in the US and other parts of the world.

Part II provides some additional background and a description of some of the new aspects. Part III presents compares test results of current meters against those obtained from the new meters and software. Part IV describes the use of linear regression and wavelength sensitivity in determining the optimum wavelengths. Part V describes optimum wavelength identification and evaluation for non-destructive chlorophyll reflectance assessment. Part VI describes the effect of leaf properties on leaf chlorophyll non-destructive assessment by spectral reflectance. Part VII describes methods of transmission and reflectance in comparison with hand-held chlorophyll meters. Part VIII provides additional description of specific embodiments of exemplary meters.

Part II

Changes in chlorophyll, nitrogen, and water content of plant leaves can occur as a result of numerous biotic or abiotic factors including, but not limited to, nutrient deficiencies, temperature stresses, drought, exposure to varying amounts of light radiation, and exposure to certain herbicides, plant pests, or diseases. Chlorophyll and nitrogen content can be used to manage nutrient and pesticide optimization programs to help improve crop yield while protecting the environment from over fertilization. Observations of changes in chlorophyll, nitrogen, and water content can also benefit the plant manager by indirectly determining how efficiently the plant is photosynthesizing. Early detection of the abiotic or biotic stresses on plant development can provide a timely opportunity to correct the situation and thus help to optimize crop productivity. The nondestructive method disclosed in this patent for detecting the content of chlorophyll, nitrogen, and water provides an early and effective detection system for determining the health of the plant and provides managers the opportunity to maximize the health and productivity of the plant.

Laboratory methods for determination of chlorophyll, nitrogen, and water content are destructive, time consuming, expensive, require professional expertise, and have the potential of chemical pollution from the reagents used. Rapid, non-destructive methods have many advantages over destructive chemical methods. There are different non-destructive approaches available for determining the plant chlorophyll status:

One method is to measure leaf fluorescence. Light energy is absorbed by chlorophyll and the energy is then used in photosynthesis to produce chemical energy. Radiation at 400-700 nm is absorbed by chlorophyll and this energy is used for photosynthesis. The capacity of a plant to photosynthesize is limited and will depend upon a range of factors including stresses caused by biotic and abiotic factors. Energy in excess of that used for photosynthesis must be effectively dissipated by non-photochemical processes. Such processes include the emission of heat and re-emission of small amounts of the absorbed radiation at longer wavelengths (red/infrared light). This re-emission of light is termed chlorophyll fluorescence. Peak fluorescence occurs in the red region of the spectrum (685 nm) and extends into the infrared region (730 nm). Leaf fluorescence increases with decreasing chlorophyll content caused by physiological stress.

Another approach used to detect chlorophyll content is to measure either the transmission of the radiation at a specific wavelength through the leaf or to measure the reflectance of the radiation at a specific wavelength reflected from the surface of the leaf. Currently, there are two commercial non-destructive meters which use light transmission to measure chlorophyll [the SPAD meter (Minolta, Japan) and the Chlorophyll Content Meter 200 ["CCM-200"] (Opti-Science, USA)] and one non-destructive meter that uses light reflectance to measure chlorophyll [Chlorophyll Meter 1000 ["CM-1000"] (Spectrum Technology, Inc; USA)]. The accuracies of all three of these meters are poor, and readings are also affected by leaf water content and texture. Moreover, these meters do not measure the chlorophyll or the water content of plant leaves. Instead, these meters claim to "measure" the green color of the leaves and the values displayed by the meters are relative values that must be compared with known standards. Therefore, these meters do not "measure" chlorophyll, nitrogen, or water content. To relate the readings of these meters to actual contents of chlorophyll, nitrogen and/or water, the user must first has some known references or standards to compare these values. For example, in order to use the SPAD meter, the user should set up the reference strips of varying leaf colors with different nitrogen application, then compare the greenness of the diagnosed plants with the reference strips. The object of this invention is to develop a meter that can directly display the actual values of chlorophyll, nitrogen and water contents without necessary to setup the reference strips. This will get rid of both time consuming chemical analysis and the setup of reference strips.

Each genotype has different leaf characteristics (physical and chemical), and these differences can have a significant effect on the transmission or reflectance of light. Therefore, the accuracy of the meter will depend on calibrating the meter for each genotype. A database containing the calibration of each genotype would be helpful in improving the accuracy of the meter.

Our Approach:

Described below are simple, accurate, and virtually instantaneous methods for determining the chlorophyll, nitrogen, and water status of intact plant leaves nondestructively. The optimum wavelengths described below for determining chlorophyll, nitrogen, and water content in intact leaves were determined by scanning fresh leaves of apple (*Malus domestica* L) ('Fuji/M26, 'Gala'/M26, 'Jonagold'/M26 and 'Liberty'/M26), 'Nonpareil' almond (*Prunus communis*), Eastern Redbud (*Cercis canadensis* var. *alba*), poplar (UCC-1, a hybrid of *Populus trichocarpa×P. deltoids*, Union Camp, Princeton, N.J.), red plum (*Prunus domestica* L.), and red maple (*Acer rubrum*). Leaves from each of these trees were scanned by using a FOSS Near Infrared (NIR) System Model-6500 over the wavelength range of 400 to 2500 nm and by using Li-1800 spectroradiometer (Li-Cor Inc., Lincoln, Nebr.) from 300 nm to 1100 nm. FOSS NIR-6500 and Li-1800 spectroradiometer were used for both leaf reflectance and transmission. After scanning the leaf discs were then cut into small pieces and placed in test tube and extracted in 80% (v/v) acetone at 4° C. in the dark. Transmittance of the extract was measured with a Shimadzu UV-visible spectrophotometer UV-1601. Total chlorophyll was calculated according to Lichtenthaler and Wellburn (1983). Total nitrogen of the scanned leaves was analyzed by using standard chemical methods. Leaf water content was evaluated by oven dry at 75° C. for 48 hours and expressed as percentage of water on a fresh weight basis.

A specific software application was developed by using MS Visual Basic 6.0 to directly calculate simple linear regression and coefficient of determination ($R^2$) between the reading of each wavelength and chlorophylls (Chl a, Chl b or Ch a+b) for each wavelength. The $R^2$ curves of Chl a, Chl b and Ch a+b, the corresponding Root Mean Square Error (RMSE) at each wavelength, and the wavelength sensitivity, and the $1^{st}$ derivation of reflectance or transmission was used for optimum wavelength selection. The software was developed for converting the meter readings directly to chlorophyll, nitrogen and water contents. In order to increase the accuracy, the software has a database for each specific species and variety analyzed.

Among other discoveries, the following is a summary of some of the important new aspects:

1. The spectral wavelengths for measuring chlorophyll and nitrogen content in plant leaves by either reflectance or transmission are:
   450-740 nm are related to chlorophyll content. The optimum wavelengths for chlorophyll and nitrogen measurements are 520-580 nm (peak 560±20 nm) and 690-740 nm (peak 720±20 nm).
2. The spectral wavelength for measuring water status in plant leaves by either transmission or reflectance:
   1400~1550 nm and 1870~2100 nm are related to plant leaf water status. The optimum ranges are between 1420-1510 nm (peak 1450±30 nm) and 1900-2000 nm (peak 1940±30 nm).
3. The spectral wavelength for leaf texture, thickness and density of plant leaves by either reflectance or transmission are:
   800-1120 nm (usually use of 940 nm is satisfactory) related to leaf texture (like leaf thickness, leaf density) These wavelengths may be used as a reference for adjusting the differences in the texture, thickness and density of plant leaves which would otherwise affect the readings for determination of chlorophyll, nitrogen and water content of leaves.
4. The meter may be developed by use of: 1) either light transmission or reflectance of the 2 to 3 different wavelengths described previously to determine the chlorophyll, nitrogen, and water content of plant leaves; 2) these wavelengths may be obtained by use of different light-emitting diodes (LEDs) that generate specific wavelength of radiation which is either transmitted through the leaf or reflected from the leaf; and 3) related photodetectors to measure the specific wavelength of radiation that is either transmitted through or reflected from the leaf.
   (1) For the 520-580 nm (peak 560±20 nm), 690-740 nm (peak 720±20 nm) and 940 nm LEDs any silicon (Si) detector [PIN photodiode, phototransistor, or avalanche photodiode (APD)] could be used. We chose a Si phototransistor because it has some internal gain, inexpensive and can work with any reverse bias from 1-20 V. This is detector D1.
   (2) For the water related LED 1420-1510 nm (peak 1450±30 nm), a Si detector will not respond, so either a Ge or InGaAs detector is required. Again, this could be a PIN photodiode, a phototransistor, or an APD. We chose a Ge PIN photodiode for our prototype because it was cheaper and had a larger spectral area than the InGaAs detectors. This is detector D2.
5. An example of the light transmission procedure for measuring the amount of chlorophyll, nitrogen, and water content in plant leaves is described below:
   First, the read head (sampling head) is closed with no leaf present in order to set the baseline signals of 100% transmission (T) at each of the four LED wavelengths. Each of the four LEDs is turned on in sequence and the appropriate detector measures the signal level in Voltage (V) which is converted to a digital signal and stored in the microcontroller.
   Next, the head is opened, a fresh leaf is placed over the sampling chamber, and the head is closed which turns on a switch and begins reading in sequence the radiations emitted by the LEDs and detected by the photodetectors. LEDs with wavelengths of 520-580 nm (peak 560±20 nm), then 690-740 nm (peak 720±20 nm), then 800-1120 nm (usually we use 940 nm) are sequentially transmitted through the leaf into the first detector (D1) for detecting light transmittance (T') in Voltage (V').
   The transmittances of these corresponding LEDs are $T_{520-580\ nm\ (peak\ 560\pm20\ nm)}$, and $T_{690-740\ nm\ (peak\ 720\pm20\ nm)}$ and $T_{800-1200\ nm\ (usually\ we\ can\ use\ 940\ nm)}$, respectively. These transmittance values are closely related to their leaf light absorbance; which in turn is related to leaf chlorophyll and nitrogen content. If the original radiation of the specific LED before penetrating the leaf is 100 and the light reflectance is ignored, the light absorbance would equal 100 minus the light transmittance. If the leaf has more chlorophyll and nitrogen, more light will be absorbed and less light will be transmitted.
   The wavelengths of 520-580 nm (peak 560±20 nm), and 690-740 nm (peak 720±20 nm) are closely related to leaf chlorophyll and nitrogen, whereas the 800-1120 nm (usually we can use 940 nm) are closely related to leaf texture and not affected by leaf chlorophyll and nitrogen.
   Combining the transmittance measured at the chlorophyll and nitrogen related wavelength [520-580 nm (peak 560±20 nm), and 690-740 nm (peak 720±20 nm)] with leaf texture related wavelength [800-1120 nm (usually we can use 940 nm)] we can eliminate the effect of leaf texture on the chlorophyll and nitrogen measurements. The following equations are some useful indices (algorithms) based on transmittance (T and T') to improve the accuracy of the readings. These indices include:

$$\text{Index}(x) = \frac{T'_{800-1100nm(usually\ use\ 940nm)} / T_{800-1100nm(usually\ use\ 940nm)}}{T'_{520-580nm(optimum\ 560nm)} / T_{520-580nm(optimum\ 560nm)}} \quad (1)$$

$$\text{Index}(x) = \frac{T'_{800-1100nm(usually\ use\ 940nm)} / T_{800-1100nm(usually\ use\ 940nm)}}{T'_{690-740nm(optimum\ 720nm)} / T_{690-740nm(optimum\ 720nm)}} \quad (2)$$

$$\text{Index}(x) = \frac{\left(T'_{800-1100nm(usually\ 940nm)} / T_{800-1100nm(usually\ 940nm)}\right) - \left(T'_{520-580nm(Opt.\ 560nm)} / T_{520-580nm(Opt.\ 560nm)}\right)}{\left(T'_{800-1100nm(usually\ 940nm)} / T_{800-1100nm(usually\ 940nm)}\right) + \left(T'_{520-580nm(Opt.\ 560nm)} / T_{520-580nm(Opt.\ 560nm)}\right)} \quad (3)$$

$$\text{Index}(x) = \frac{\left(T'_{800-1100nm(usually\ 940nm)} / T_{800-1100nm(usually\ 940)}\right) - \left(T'_{690-740nm(Opt.\ 720nm)} / T_{690-740nm(Opt.\ 720nm)}\right)}{\left(T'_{800-1100nm(usually\ 940nm)} / T_{800-1100nm(usually\ 940)}\right) + \left(T'_{690-740nm(Opt.\ 720nm)} / T_{690-740nm(Opt.\ 720nm)}\right)} \quad (4)$$

$$\text{Index}(x) = \int_{690nm}^{740nm} \left(\frac{T'_\lambda / T_\lambda}{T'_{720nm} / T_{720nm}} - 1\right) d\lambda \quad (5)$$

The indices (1) and (2) are very similar, and the indices (3) and (4) are similar. The difference is the chlorophyll related wavelength either in the red range (520-580 nm, optimum 560 nm) or in the red edge (690-740 nm, optimum 720 nm). According to the algorithm, a leaf with higher Chl content will absorb more light; therefore, the photodiode will receive less light (T') that is transmitted through the leaf to produce a lower voltage V'. With a smaller denominator in the equation the meter will finally generate a larger reading. In contrast, a leaf with lower Chl content will absorb less light; therefore, the photodiode will receive more light (T') to produce a higher voltage V', resulting in a smaller reading. The index (5) is calculated by using a discrete summation approximation. The transmission from 690 to 740 nm divided by the transmission at wavelength 720 nm improved the accuracy.

Since the digital signals received by the detectors are stored in voltage, the transmission (T' and T) in the above indices can be replaced by voltage (V' and V) with and without leaf sample.

$$\text{Index}(x) = \frac{V'_{800-1100nm(usually\ use\ 940nm)} / V_{800-1100nm(usually\ use\ 940nm)}}{V'_{520-580nm(optimum\ 560nm)} / V_{520-580nm(optimum\ 560nm)}} \quad (1)$$

$$\text{Index}(x) = \frac{V'_{800-1100nm(usually\ use\ 940nm)} / V_{800-1100nm(usually\ use\ 940nm)}}{V'_{690-740nm(optimum\ 720nm)} / V_{690-740nm(optimum\ 720nm)}} \quad (2)$$

$$\text{Index}(x) = \frac{\left(V'_{800-1100nm(usually\ 940nm)} / V_{800-1100nm(usually\ 940nm)}\right) - \left(V'_{520-580nm(Opt.\ 560nm)} / V_{520-580nm(Opt.\ 560nm)}\right)}{\left(V'_{800-1100nm(usually\ 940nm)} / V_{800-1100nm(usually\ 940nm)}\right) + \left(V'_{520-580nm(Opt.\ 560nm)} / V_{520-580nm(Opt.\ 560nm)}\right)} \quad (3)$$

$$\text{Index}(x) = \frac{\left(V'_{800-1100nm(usually\ 940nm)} / V_{800-1100nm(usually\ 940)}\right) - \left(V'_{690-740nm(Opt.\ 720nm)} / V_{690-740nm(Opt.\ 720nm)}\right)}{\left(V'_{800-1100nm(usually\ 940nm)} / V_{800-1100nm(usually\ 940)}\right) + \left(V'_{690-740nm(Opt.\ 720nm)} / V_{690-740nm(Opt.\ 720nm)}\right)} \quad (4)$$

$$\text{Index}(x) = \int_{690nm}^{740nm} \left(\frac{V'_\lambda / V_\lambda}{V'_{720nm} / V_{720nm}} - 1\right) d\lambda \quad (5)$$

The above indices formulas produce relative indices rather than the actual values of chlorophyll or nitrogen. In order to directly obtain the actual content of chlorophyll and nitrogen we need to first know the relationship between the above indices and the chlorophyll or nitrogen contents. We developed databases for each of the plant species/varieties tested and these databases and the relationships to chlorophyll and nitrogen are stored in the computer. The most common equations we used include the following three:

$$Y_{Chlorophyll\ or\ Nitrogen} = A \times \text{Index}(x)^2 + B \times \text{Index}(x) + C \quad (1)$$

$$Y_{Chlorophyll\ or\ Nitrogen} = A \times e^{\text{Index}(x)} \quad (2)$$

$$Y_{Chlorophyll\ or\ Nitrogen} = A \times \text{Index}(x)^B \quad (3)$$

A, B and C are constants, and Index(x) is the results of the indices. Among the 3 equations, equation (1) can be used in most of the conditions.

The next sequence of readings is the 1450 nm LED which transmits light through the leaf to the second photo detector (D2). At this wavelength ($A_{1450}$) the light intensity is not affected by the amount of chlorophyll or nitrogen content of the leaf as this wavelength is specific to the water content and the texture/density of the leaf. Knowing the leaf water content is an important factor as it affects the transmission and reflectance of light at the specific wavelengths used to determine chlorophyll and nitrogen content. Therefore, to eliminate the effects of the water content in the leaf and improve the accuracy of the meter, the LED at wavelengths 1400~1550 nm or 1870~2100 nm is required to measure the light intensity to determine the water status of the leaf. The relationships to improve the meter accuracy for determining chlorophyll, nitrogen and water status are as follows:

$$\text{Index}(x)' = \frac{\text{Index}(x)}{T'_{1400-1550nm(optimum\ 1450nm)} / T_{1400-1550nm(Optimum\ 1450nm)}} \quad (6)$$

$$\text{Index}(x)' = \frac{\text{Index}(x) - \left(\frac{T'_{1400-1550nm(Optimum\ 1450nm)} /}{T_{1400-1550nm(Optimum\ 1450)}}\right)}{\text{Index}(x) + \left(\frac{T'_{1400-1550nm(optimum\ 1450nm)} /}{T_{1400-1550nm(Optimum\ 1450)}}\right)} \quad (7)$$

The index(x) is the indices we obtain from either the index (1), (2), (3), (4) or index (5). If the transmissions of radiation at the water related wavelengths (T' and T) were replaced by the corresponding detector voltages, we obtain the following indices:

$$\text{Index}(x)' = \frac{\text{Index}(x)}{V'_{1400-1550nm(optimum\ 1450nm)} / V_{1400-1550nm(Optimum\ 1450nm)}} \quad (6)$$

$$\text{Index}(x)' = \frac{\text{Index}(x) - \left(\frac{V'_{1400-1550nm(Optimum\ 1450nm)} /}{V_{1400-1550nm(Optimum\ 1450)}}\right)}{\text{Index}(x) + \left(\frac{V'_{1400-1550nm(optimum\ 1450nm)} /}{V_{1400-1550nm(Optimum\ 1450)}}\right)} \quad (7)$$

Similarly, we can use the following equation to obtain the actual concentration of chlorophyll and nitrogen.

$$Y'_{Chlorophyll\ or\ Nitrogen} = A \times \text{Index}(x)'^2 + B \times \text{Index}(x)' + C \quad (1)$$

$$Y'_{Chlorophyll\ or\ Nitrogen} = A \times e^{\text{Index}(x)'} \quad (2)$$

$$Y'_{Chlorophyll\ or\ Nitrogen} = A \times \text{Index}(x)'^B \quad (3)$$

The quantity of red pigments in leaves affects the chlorophyll readings at 520-580 nm. We have found that at 690-740 nm the content of red pigment in leaves does not affect the chlorophyll readings. Therefore, we used the 690-740 nm wavelength rather than 520-580 nm as in other conventional approaches.

We discovered that the wavelengths 1400~1550 nm and 1870~2100 nm and an associated detector (for either transmittance or reflectance) could be used to determine the water status of plant leaves.

6. With the similar technique discussed above, we can obtain similar indices (relationships) and equations for determining chlorophyll, nitrogen and water based on the methods of reflectance.

Prior Patents on Fresh Leaf Chlorophyll Measurement

1. U.S. Pat. No. 6,020,587: Plant chlorophyll content meter NASA patent
   (1) Wavelengths used: 700 nm and 840 nm. The signal is from leaf reflectance.
   (2) Algorithm: The "chlorophyll index" indicates the chlorophyll relative content:

INDEX=(840 nm/840$A$)/(700 nm$R$/700 nm$A$)

Here: R=quantity of light reflected from the sample; A=quantity of ambient light 2. U.S. Pat. No. 4,295,042: Method of and device for measuring chlorophyll of living leaves, Tokyo, Japan
   (1) Spectral wavelength claimed: first LED has a spectroscopic distribution ranging from 660 nm to 690 nm (shorter wavelength); and second LED has a spectroscopic distribution ranging from 760 nm to 1100 nm (long wavelength). The shorter wavelength changed with the amount of chlorophyll content as measured by transmission; while the long wavelength did not change with varying amount of chlorophyll.
   (2) Algorithm: The difference of the two photodiode readings is the relative amount of chlorophyll contained in the leaf. The algorithm is: log ($R760_{Detector\ Reading}/R670_{Detector\ Reading}$)=log $R760_{Detector\ Reading}$−Log $R670_{Detector\ Reading}$.

Part III

Invention Development, Initial Records, and Results of First Model

1. Found why SPAD was not Accurate and Determined the Optimum Wavelength for Chlorophyll and N Assessment Used FOSS NIR-6500 and Li-1800 spectroradiometer (Li-Cor Inc., Lincoln, Nebr.) and SPAD meter to measure leaf chlorophyll and N. The leaves with different N and chlorophyll of Fuji apple, poplar and almond created by fertigation were scanned on September 14, 20 and 24, respectively, with these two NIR systems and SPAD meter. After scanning, the N and chlorophyll content of these leaves were analyzed by using standard chemical methods. We found the SPAD meter was not accurate in measuring relative chlorophyll and nitrogen content. Then we did a simple linear regression analysis for each wavelength from 300-1100 nm (LI-1800 spectroradiometer) and from 400 nm to 2500 nm (FOSS NIR-6500). We analyzed all the chlorophyll and N data and found that the SPAD meter (650 nm) was not the optimum wavelength for measuring chlorophyll and N (FIGS. 1-6, table 1-3). In our analysis we found the following two wavelength peaks that were significantly better for measuring chlorophyll for all leaves tested: 1) in the NIR range (685-730 nm), and 2) in the visible green range (560-650 nm). In addition we found that the wavelength 800-1120 nm related to leaf texture (like leaf thickness, leaf density). We also found that the readings in this range were not affected by chlorophyll content. We used these wavelengths as a reference for eliminating the effects of leaf texture, thickness and density of plant leaves.

We determined that the wavelength sensitivity method was a good way for determining the optimum wavelength selection in comparisons with simple linear regression, R2 and RMSE (FIG. 1). Use of the wavelength sensitivity, R2 and RMSE, test helped us to verify that the wavelength in the NIR range (685-730 nm) and visible range (560-650 nm) were the optimum wavelengths for chlorophyll and N analysis. We then created a software application to convert the meter reading into chlorophyll and N concentrations. We also developed a software database for different plant species and cultivars.

2. Production of the First OSU Prototype

Based on the wavelengths we selected, the first OSU prototype was developed. In order to test and verify the accuracy and reliability of the OSU prototype, apple leaf samples of 'Cameo' (sampled from Fleming's Orchard), 'Fuji', 'Jonagold', and 'Gala' (Sampled from the Lewis-Brown Horticulture Farm at OSU) were measured with the meters shown in Table 1 and 2. The data shows that the first OSU prototype was significantly more accurate than all other meters tested (e.g., had higher $R^2$ than other meters) for both chlorophyll and nitrogen content in fresh leaves (Tables 1 and 2, respectively).

TABLE 1

The relationship between chlorophyll and the readings of CNDS, SPAD meter, Observer, CCM-200

| Apple Cultivar | Instrument | Equation | $R^2$ |
|---|---|---|---|
| Cameo | OSUP | $y = 0.0044e^{0.0314x}$ | 0.9486 |
| | SPAD | $y = 0.0049e^{0.0467x}$ | 0.9073 |
| | Observer | $y = 0.0025e^{0.0146x}$ | 0.8556 |
| | CCM-200 | $y = 0.0149e^{0.032x}$ | 0.7996 |
| Jonagold | OSUP | $y = 0.0036e^{0.0342x}$ | 0.8952 |
| | SPAD | $y = 0.0047e^{0.0494x}$ | 0.8334 |
| | Observer | $y = 0.0057e^{0.0107x}$ | 0.6910 |
| | CCM-200 | $y = 0.017e^{0.0303x}$ | 0.7439 |
| Fuji | OSUP | $y = 0.0041e^{0.0334x}$ | 0.9023 |
| | SPAD | $y = 0.0041e^{0.0511x}$ | 0.8990 |
| | Observer | $y = 0.0035e^{0.0102x}$ | 0.8257 |
| Gala | OSUP | $y = 0.0489e^{0.0258x}$ | 0.9640 |
| | SPAD | $y = 0.0273e^{0.0549x}$ | 0.8922 |
| | SPAD | $y = 0.0423e^{0.0408x}$ | 0.9025 |

TABLE 2

The relationship between nitrogen and the readings of CNDS, SPAD meter, Observer, CCM-200

| Apple Cultivar | Instrument | Equation | $R^2$ |
|---|---|---|---|
| Cameo | OSUP | $y = 1.1024e^{0.0086x}$ | 0.8841 |
| | SPAD | $y = 1.1623e^{0.0124x}$ | 0.7930 |
| | Observer | $y = 0.9592e^{0.0039x}$ | 0.7616 |
| | CCM-200 | $y = 1.5919e^{0.0079x}$ | 0.6050 |
| Jonagold | OSUP | $y = 0.819e^{0.0117x}$ | 0.8922 |
| | SPAD | $y = 0.9105e^{0.0167x}$ | 0.8078 |
| | Observer | $y = 0.9949e^{0.0035x}$ | 0.6198 |
| | CCM-200 | $y = 1.3994e^{0.0104x}$ | 0.7458 |
| Fuji | CNDS | $y = 0.6037e^{0.0215x}$ | 0.8840 |
| | OSUP | $y = 0.6208e^{0.0326x}$ | 0.8478 |
| | Observer | $y = 0.5678e^{0.0064x}$ | 0.7756 |
| Gala | OSUP | $y = 1.0191e^{0.0125x}$ | 0.9185 |
| | SPAD | $y = 0.7812e^{0.026x}$ | 0.8945 |

3. Effect of Leaf Texture and Water Status on Accuracy

Figure 2B:
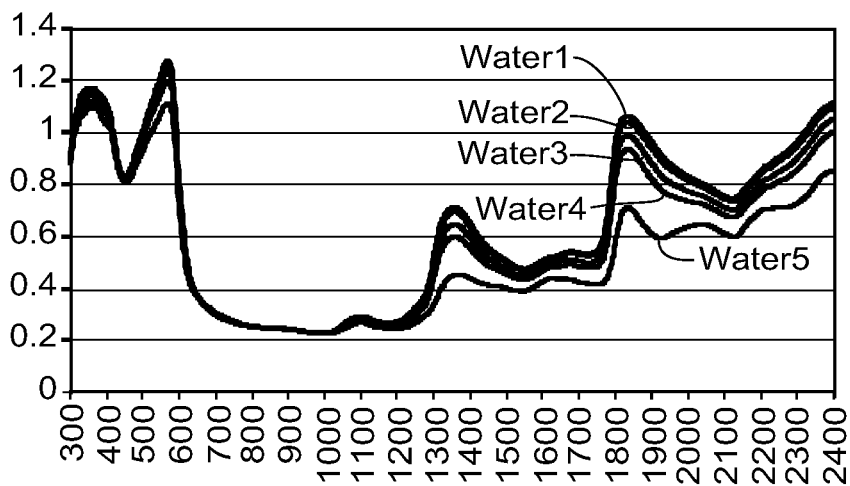
Figure 2C:
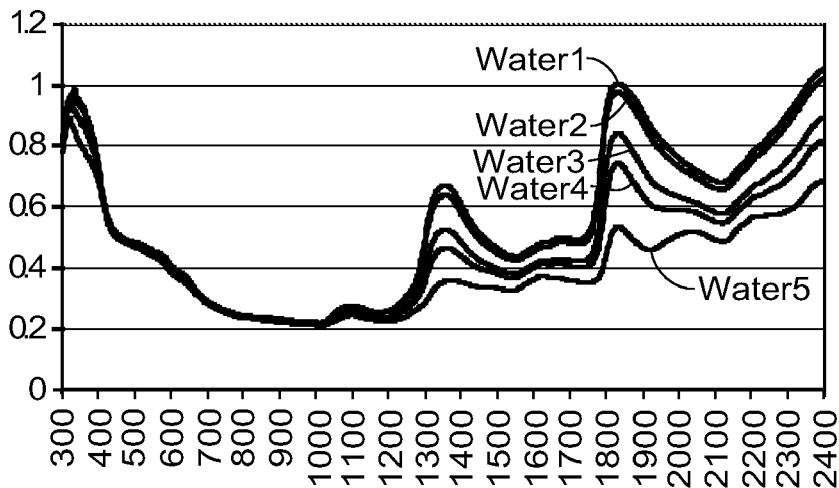

The accuracy of the readings at the optimum wavelengths we selected for chlorophyll and nitrogen determination was affected by the leaf water status (FIGS. 2A, 2B, and 2C). FIG. 2A indicated that the reading for the leaves with chlorophyll (Green1, Green2 and Green3) were different from the leaves without chlorophyll (Yellow1, Yellow2, and Yellow3). However, these leaves had similar amount of water content (Green leaf disc 0.0253 g, yellow leaf disc 0.0254 g). The peaks in the NIR range (750-1200 nm) were similar for leaves with similar texture and water content that with or without chlorophyll. When leaf disc were dehydrated to water contents of 0.0253, 0.022, 0.0161, 0.0113, or 0.0018 g/disc for green leaf (FIG. 2B) or to 0.0254, 0.0203, 0.0114, 0.0059, or 0.0001 g/disc for the yellow leaf (FIG. 2C), the readings at both the visible and NIR ranges were decreased gradually. These results verified that the leaf water status must be accounted for in order to obtain accurate leaf chlorophyll and N concentrations at the various wavelengths we had selected.

Figure 3A:
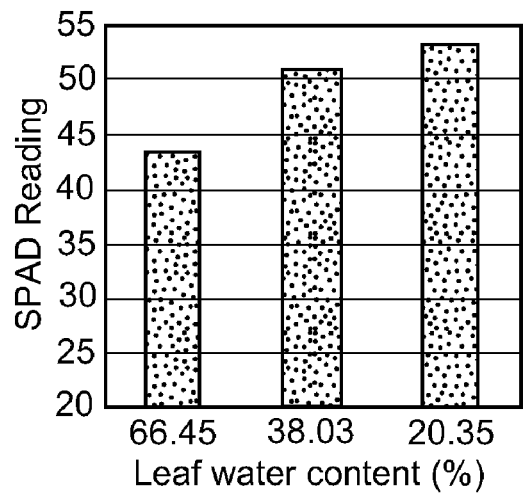
FIGS. 3A-3C show bar graphs of meter readings for leaf water status for various leaf water contents and for different meters.
Figure 3B:
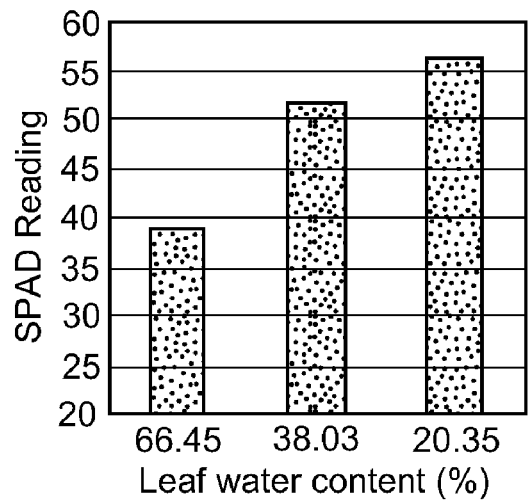
Figure 3C:
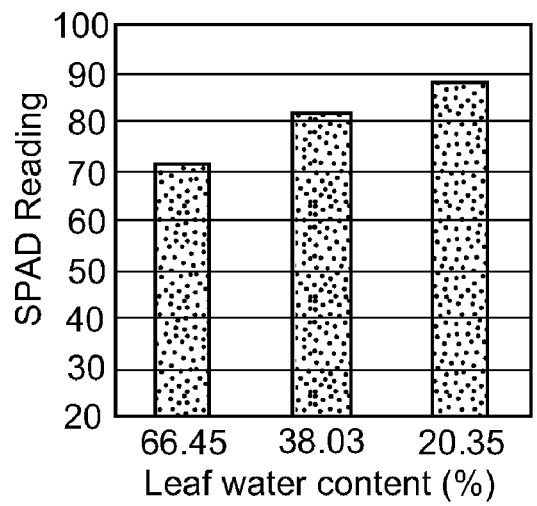
Figure 4:
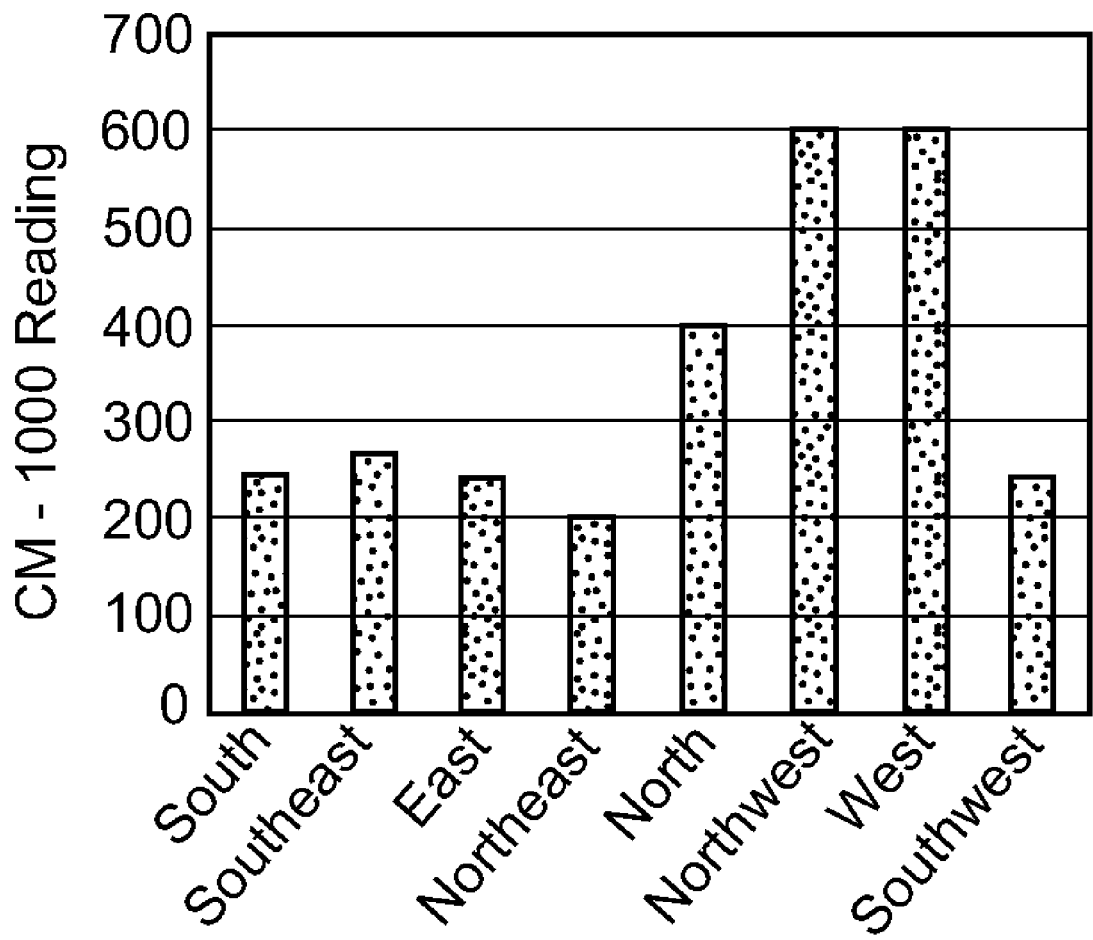
FIG. 4 shows a bar graph illustrating the effect of sampling direction on CM-1000 meter readings for a poplar leaf.
Figure 5:
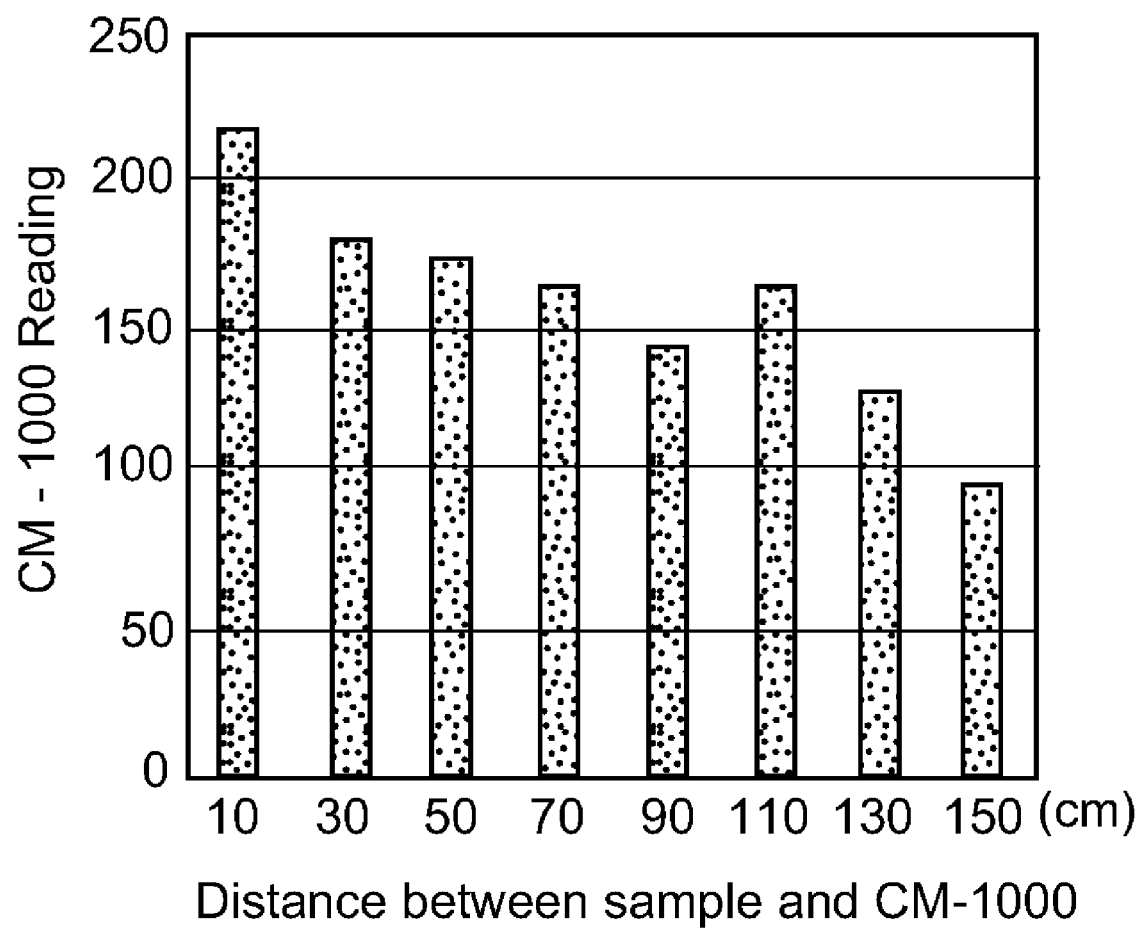
FIG. 5 shows a bar graph illustrating the effect of sampling distance on CM-1000 meter readings for a poplar leaf.

To correct this problem, we determined that the readings at the range of 750-1200 nm were only slightly affected by the leaf water status. This indicated that the wavelength between 750-1200 nm could be used as a reference to eliminate leaf thickness and texture effect on chlorophyll and N measurement. The wavelengths between 1400~1550 nm and 1870~2100 nm are related to the leaf water status. The optimum range for determining water content are between 1420-1510 nm (peak 1450±30 nm) and 1900-2000 nm (peak 1940±30 nm). By using the wavelength at 750-1200 nm as a reference, we can eliminate the effects of leaf texture on leaf water content measurements. The leaf chlorophyll and N content of leaves can be determined by use of the red edge wavelength range of 685-730 nm or visible wavelength of 560-650 nm in combination with one wavelength at 750-1200 nm to eliminate leaf texture effect and one water related wavelength 1420-1510 nm (peak 1450±30 nm) and 1900-2000 (peak 1940±30 nm) to eliminate the water effect in specific algorithm to make the chlorophyll and N diagnoses more accurate, meanwhile, we can get leaf chlorophyll, N and water contents. Leaf water status affects the reading from the commercial meters and the first OSU prototype (FIG. 3). Decreasing the leaf water content increases the reading of SPAD meter, CCM-200 meter and the OSU prototype.

4. Analysis of the Relationship Between Meter Design on Meter Accuracy

The most important factor that affected the accuracy of the meter was the wavelength (LEDs) used by the meter. In addition to the wavelength, other factors that had an effect on the accuracy of the meter were:

1) The stability of light source (LEDs): For example, the SPAD meter and CCM-200 used the inside LEDs as the light source, which was more stable than the light from natural light sources. This explains why the SPAD and CCM-200 meters were more accurate than the CM-1000.

2) The sampling distance and direction (Table 3 and FIGS. 4 and 5): The CM-1000 was the least accurate of the meters tested because the distance of the meter to the leaves had a significant effect on the accuracy of the meter. The CM-1000 meter accuracy was also affected by the heading direction when measurement was taken.

TABLE 3

Relationship between structure and meter accuracy

| Meter | SPAD Meter | CCM-200 Meter | OSU Prototype | CM-1000 Meter |
|---|---|---|---|---|
| Mechanism | Transmission | Transmission | Transmission | Reflectance |
| Light Source | Inside LEDs, Stable | Inside LEDs, Stable | Inside LEDs, Stable | Nature light, affected by direction, condition |
| Sampling Distance | Constant | Constant | Constant | Not Stable |
| Accuracy | Accurate | Accurate | Accurate | Not accurate |

5. Development of the Second OSU Prototype

A second OSU prototype (OSU-II) with 4 LEDs having the wavelengths 565 nm, 700 nm, 940 nm and 1450 nm was built. The results showed that the OSU-II prototype was significantly more accurate than OSU-I prototype and all other meters tested (higher $R^2$ than other meters) in measuring chlorophyll (Table 4)

TABLE 4

The $R^2$ between meter reading and chlorophyll content

| Cultivar/Varieties | CM-1000 | CCM-200 | SPAD | OSU-I | OSU-II |
|---|---|---|---|---|---|
| Cameo apple | 0.6790 | 0.8332 | 0.9046 | 0.9298 | 0.9231 |
| Gala apple | 0.8077 | 0.8661 | 0.9034 | 0.9080 | 0.9281 |
| Fuji apple | 0.8844 | 0.8343 | 0.9090 | 0.9295 | 0.9348 |

TABLE 4-continued

The $R^2$ between meter reading and chlorophyll content

| Cultivar/Varieties | CM-1000 | CCM-200 | SPAD | OSU-I | OSU-II |
|---|---|---|---|---|---|
| Bartlet pear | 0.3981 | 0.8835 | 0.8802 | 0.902 | 0.9109 |
| Comice pear | 0.6488 | 0.9012 | 0.8233 | 0.9115 | 0.9214 |
| Bing cherry | 0.5613 | 0.7026 | 0.7343 | 0.7474 | 0.8338 |
| Skeena cherry | 0.7609 | 0.8739 | 0.8971 | 0.8904 | 0.9053 |
| Regina cherry | 0.6237 | 0.7443 | 0.7553 | 0.8571 | 0.9028 |
| Pinot Noir Grape | 0.8866 | 0.8726 | 0.9087 | 0.9171 | 0.9293 |
| Poplar | 0.8010 | 0.8743 | 0.8862 | 0.9085 | 0.9221 |

6. Development of Software

Currently, there are three commercial meters for determining either the green color or chlorophyll content of leaves: 1) the SPAD meter; 2) The CCM-200; and 3) the CCM-1000. The accuracies of these meters are poor and the readings that are displayed by the meter are neither the chlorophyll content nor nitrogen content of the leaves. The readings are the relative greenness of the leaves only. Employing any of these meters requires the use of reference color strips which were created by different N fertilization and were used as a comparative reading with the color of the leaves These reference colors are not standardized and each user must select and calibrate reference strips and correlate these colors with the color of the leaves. This procedure is difficult and researchers and plant producers are discouraged from using these meters for measuring plant leaf colors. To be useful the researcher and/or grower are interested in converting the meter readings to chlorophyll and nitrogen content. Currently none of the commercial meters are equipped with software to make these conversions possible. Our goal are thus to develop a meter than is capable of accurately determining the chlorophyll and nitrogen content of plant leaves and develop a software for converting the readings of the meter into chlorophyll, N and water content.

This is the main reason the PING Meter (also an OSU meter) and the PINGS software were developed. The PINGS software converts the PING Meter reading into chlorophyll and nitrogen content. The software with some modification can also be used for converting the SPAD, CCM-200 and CM-1000 meters readings into chlorophyll contents.

The PINGS software is the only software available for instantly converting the meter readings into plant chlorophyll and nitrogen contents. The software was designed by incorporating statistical functions, modeling and regression, and by developing database for specific plant cultivars/varieties. The chlorophyll and nitrogen databases for the various plant cultivars/varieties are an important factor in improving the accuracy of the meter readings as the readings varies with plant cultivars/varieties.

Part IV

The Use of Simple Linear Regression $R^2$ and Wavelength Sensitivity Analysis for Determining the Optimum Wavelength for Measuring Chlorophyll Content in Leaves 'Nonpareil' almond (*Prunus dulcis* (Mill.) D. A. Webb), poplar (UCC-1, a hybrid of *Populus trichocarpa×P. deltoides*, Union Camp, Princeton, N.J.) and 'Fuji' apple (*Malus domestica* Borkh) trees grown in 7.2 L pots with a medium of 1 peat moss:2 pumice:1 sandy loam soil (v:v). These trees were fertilized twice weekly with one of the six N concentrations (0, 2.5, 5, 7.5, 10, or 20 mM) to create leaves with different chlorophyll contents from 109 to 336 $\mu m \cdot m^{-2}$ in 'Fuji' apple, 64 to 220 $\mu m \cdot m^{-2}$ in poplar, and 57 to 221 $\mu m \cdot m^2$ in almond respectively. A 2.85 $cm^2$ discs sampled from each leaf with different chlorophyll content scanned by using Li-1800 spectroradiometer from 300 nm to 1100 nm with 1 nm interval to measure the spectral reflectance. After scan the contents of chlorophyll a, b and a+b for the leaf discs were analyzed. Simple linear regression coefficient determination ($R^2$), wavelength sensitivity and $1^{st}$ derivation of reflectance spectrum were used for optimum wavelengths determination of chlorophyll content by non-destructive analysis. The results indicated that the $1^{st}$ derivative could be used to roughly determine the near infrared (NIR) spectral band for chlorophyll content determination, and the wavelength sensitivity analysis can be used roughly to determine the optimum near infrared (NIR) and visible range wavelength. However, it is difficult to use either the $1^{st}$ derivative or wavelength sensitivity for determining the optimum wavelength that relates to the leaf chlorophyll content because the optimum wavelength selected according to both methods tended to shift away from the optimum wavelength position. However, the use of the wavelength sensitivity analysis was better for selecting the optimum wavelength than $1^{st}$ derivative because wavelength sensitivity is based on the chlorophyll content (determined by chemical analysis) whereas the $1^{st}$ derivative could not be used to verify whether the spectral difference was caused by the difference in chlorophyll content. Coefficient of determination ($R^2$) is a good indicator for verifying the optimum wavelength selected for chlorophyll content determination. Higher $R^2$ is usually associated with higher wavelength sensitivity and greater accuracy in measuring leaf chlorophyll content. The wavelengths with the highest $R^2$ and highest sensitivity were therefore used to select the optimum wavelengths for chlorophyll content determination in leaves. Our results indicated that the simple linear regression $R^2$ analysis in combination with wavelength sensitivity was a reliable method for determining the optimum wavelength for chlorophyll content assessment in plant leaves.

The chlorophylls, Chl a and Chl b, are essential pigments for the conversion of light energy to stored chemical energy (Gitelson et al 2003, Richardson et al 2002). From both physiological and applied perspectives leaf chlorophylls are important for the following reasons (Richardson et al 2002): First, the amount of solar radiation absorbed by a leaf is largely a function of the foliar concentration of photosynthetic pigments, and thus chlorophyll content can directly limit photosynthetic potential and primary production (Curran et al. 1990, Filela et al 1995); Second, a large portion of leaf nitrogen is incorporated in chlorophyll; therefore chlorophyll content are often used as an indirect estimation of nutrient nitrogen status (Filella et al 1995, Moran et al 2000); and Third, leaf chlorophyll content was found to be closely related to plant stress (Carter and Knapp 2001, Hendry 1987, Peñuelas and Filella 1998).

Traditionally, leaf extraction with organic solvents and spectrophotometric determination of solutions are required for chlorophyll analysis by wet chemical methods (Arnon 1949). Recently, an alternative nondestructive method for chlorophyll assessment was developed which was based on the absorbance and/or reflectance of light by the intact leaf (Curran et al. 1990, Adams et al. 1999, Datt 1999, Gamon and Surfus 1999, Markwell et al. 1995). These nondestructive methods require no chemical analysis, are simple to use, fast, inexpensive and can be used in the field (Buschmann and Nagel 1993, Gitelson and Merzlyak 1994, Gitelson et al 1996a, 1996b, Markwell et al 1995).

Most of the previous papers were focused on either chlorophyll related indices or algorithm development and evaluation (Curran et al., 1990; Gitelson & Merzlyak, 1994, 1996; Gitelson et al., 1996a, 1996b, Blackburn 1998, Datt 1998, 1999; Adams et al., 1999; Gamon & Surfus, 1999). However, these indices have rarely been tested by using data from species other than those used in the formulation of the index (Richardson et al 2002). In some cases, the results of such tests are not presented in a way that allows meaningful comparison of the indices across different studies (Gitelson et al 2003, Richardson et al 2002).

There are many reasons why the proposed indices or algorithms are not applicable in published studies. However, the main reason is that the optimum wavelengths for measuring chlorophyll vary with the plant genotype and other characteristics of the plant leaf. Determination of the optimum wavelength is dependent on consideration of all these characteristics.

In order to select optimum spectral wavelength for chlorophyll the first or second derivative of the spectra have been used widely in wavelength selection and indices development (Curran et al 1990, Dixit and Ram 1985, Gitelson et al 1996, 2003, Morrey 1968, Richardson et al 2002). Derivative is a very useful analytical tool for characterizing an analytic band that is overlapped by other bands with different halfwidths. It can resolve or enhance smaller peaks that are incompletely resolved from larger peaks due to background and/or buried in the noise (Dixit and Ram 1985, Moran et al. 2000, Morrey 1968). However, derivatives will change the original peak form and may eliminate some important peaks.

Different substances or molecules have specific absorption or reflection spectra. Based on the changes of spectral absorption, transmission or reflectance, these specific substances or molecules can be measured at specific wavelengths. Different wavelengths have different levels of sensitivity and different coefficient of determination ($R^2$) in measuring any specific substance or molecule. Wavelength sensitivity explains how sensitive the specific wavelength is in measuring chlorophyll, whereas $R^2$ is the essential indicator and a measure of goodness-of-fit of linear regression. Theoretically, the optimum wavelength(s) for non-destructive chlorophyll measurement should have the highest wavelength sensitivity and highest $R^2$ between spectral wavelength readings and leave chlorophyll contents. Regression $R^2$ has been widely used in laboratory quantitative analysis. However, only few studies have been reported using the $R^2$ of wavelength reading versus leaf chlorophyll content in wavelength selection (Gitelson et al 2003). Sensitivity analysis has been used to identify stress-sensitive wavelengths, and is closely associated with chlorophyll concentration (Carter 1993, 1994, Moran 2000). However, none of these studies combined both $R^2$ and wavelength sensitivity to determine the optimum wavelength for chlorophyll measurement.

The purpose of this study was to evaluate the methods of regression coefficient of determination ($R^2$) and wavelength sensitivity analysis to determine the optimum wavelength chlorophyll assessment and comparing this with the widely used method of $1^{st}$ spectral derivative.

Materials and Methods

1. Plant Materials

'Nonpareil' almond (*Prunus dulcis* (Mill.) D. A. Webb), poplar (UCC-1, a hybrid of *Populus trichocarpa*×*P. deltoides*, Union Camp, Princeton, N.J.) and bench-grafted 'Fuji' apple (*Malus domestica* Borkh) trees on M.26 rootstocks were grown in 7.2 L pots with a medium of 1 peat moss:2 pumice:1 sandy loam soil (v:v) in a lathhouse from 26 March to 5 June. Beginning from budbreak in early May, they were fertilized every 2 weeks with 10.7 mM N, using Plantexâ 20N-10P2O5-20K2O water-soluble fertilizer with micronutrients (Plantex Corp., Ontario, Canada). When the new shoots were approximately 15 cm long, plants were moved to full sunlight. Thereafter, they were fertilized weekly with Plantexâ for 3 weeks. Beginning on 30 June, plants were fertilized twice weekly with one of the six N concentrations (0, 2.5, 5, 7.5, 10, or 20 mM N from NH4NO3) by applying 300 ml of a modified Hoagland's solution to each pot until the end of September in three successive years.

2. Method Used for Wavelength Selection and Verification

The range of leaf total chlorophyll content for the different N fertigation treatments were from 109 to 336 $\mu m \cdot m^{-2}$ in 'Fuji' apple, 64 to 220 $\mu m \cdot m^{-2}$ in poplar, and 57 to 221 $\mu m \cdot m^{-2}$ in almond, respectively. From August to September, 10 fresh leaves from each N fertigation treatment from the above plants were harvested and immediately placed into plastic bags for transport to the laboratory. Leaf discs taken with a 2.85 $cm^2$ cork borers were immediately scanned by using Li-1800 spectroradiometer (Li-Cor Inc., Lincoln, Nebr.) from 300 nm to 1100 nm with 1 nm interval to measure the spectral reflectance. After scanning, the leaf discs were then cut into small pieces and placed in test tube and extracted in 80% (v/v) acetone at 4° C. in the dark. Transmittance of the extract was measured with a Shimadzu UV-visible spectrophotometer UV-1601. Total chlorophyll was calculated according to Lichtenthaler and Wellburn (1983).

3. Simple Linear Regression and Coefficient Determination ($R^2$) Analyses

Specific software was developed by using MS Visual Basic 6.0 to directly calculate simple linear regression and coefficient of determination ($R^2$) between the reading of each wavelength and chlorophylls (Chl a, Chl b or Ch a+b) for each wavelength from 300 nm to 1100 nm with 1 nm interval. The $R^2$ curves of Chl a, Chl b and Ch a+b were developed at each wavelength for optimum wavelength determination. The reflectance curves of the leaves with different chlorophyll content were recorded.

4. Reflectance Difference and Wavelength Sensitivity Analyses

The reflectance curves of the leaves with different chlorophyll contents in 'Fuji' apple (109, 148, 229 or 336 $\mu m \cdot m^{-2}$), poplar (64, 78, 15 or 220 $\mu m \cdot m^{-2}$) and almond (57, 83, 123 or 221 $\mu m \cdot m^{-2}$) were developed for wavelength from 300 nm to 1100 nm. The reflectance value of leaf with different chlorophyll content was subtracted from that of the leaf with lowest chlorophyll content at each measured wavelength, to produce the reflectance difference curve. This curve was then normalized by dividing the original reflectance values of the leaf with the lowest chlorophyll content, to produce the reflectance based sensitivity curve. The reflectance difference curve was normalized by dividing the chlorophyll difference between the leaf with the lowest chlorophyll content and the other leaves to produce the Ch a, Ch b or Ch a+b based sensitivity curve for the optimum wavelength analysis.

5. $1^{st}$ Derivation of Reflectance

The $1^{st}$ derivation of reflectance spectrum is also called first-difference spectrum and calculated as $(R_n - R_{n-1})/(\lambda_n - \lambda_{n-1})$. The first-difference spectrum measures the amount of changes in the reflectance from one wavelength to the next; it is a measure of the slope of the raw reflectance spectrum (Richardson and Berlyn 2002).

Results

1. Reflectance Difference and Wavelength Sensitivity

Figure 6A:
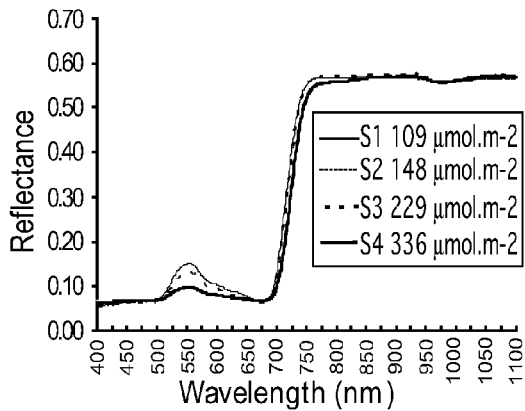
FIGS. 6A-6F show graphs of the reflectance spectrum (A), the reflectance difference (B), sensitivity based on reflectance (C), sensitivity based on Ch a (D), sensitivity based on Ch b (E) and sensitivity based on Ch a+Ch b (F) of four 'Fuji' apple leaves with chlorophyll contents of 109, 148, 229, and 336 $\mu mol \cdot m^{-2}$, respectively.
Figure 6D:
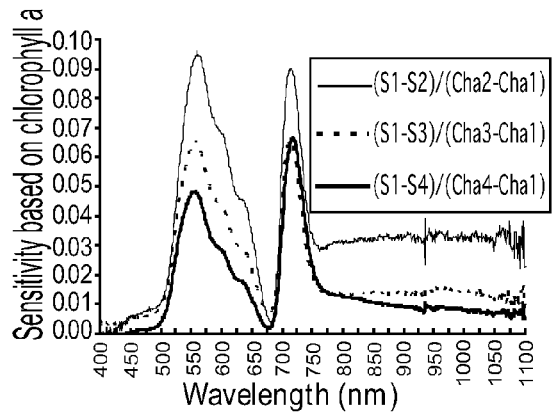
Figure 6B:
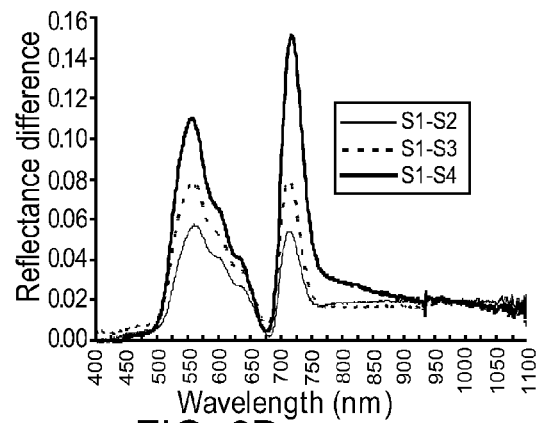
Figure 6E:
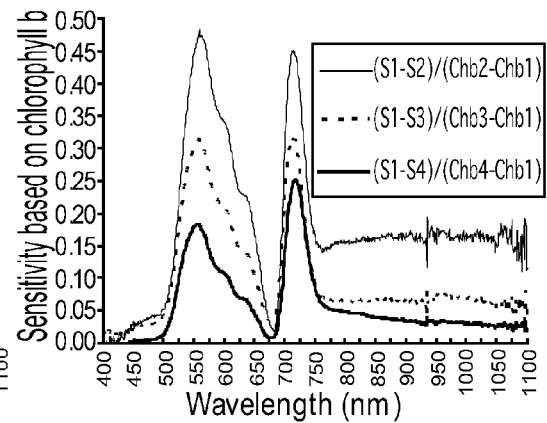
Figure 6C:
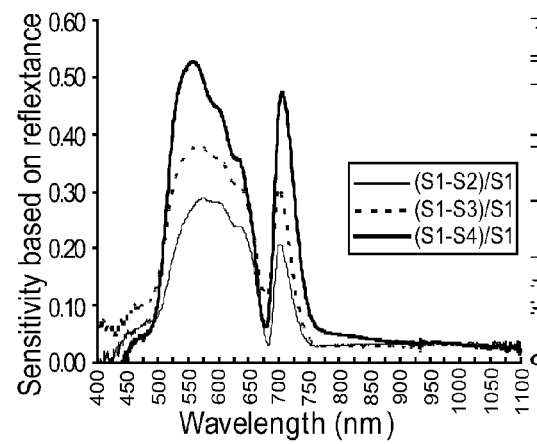
Figure 6F:
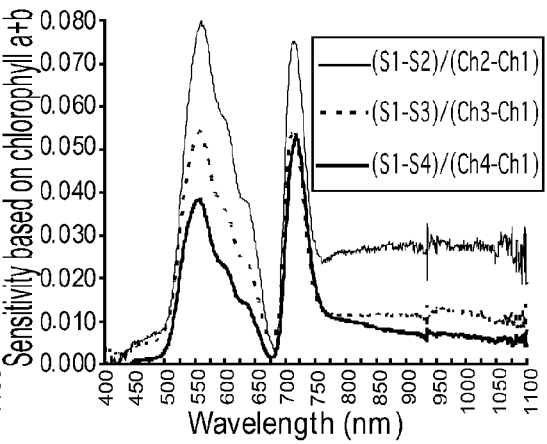
Figure 7A:
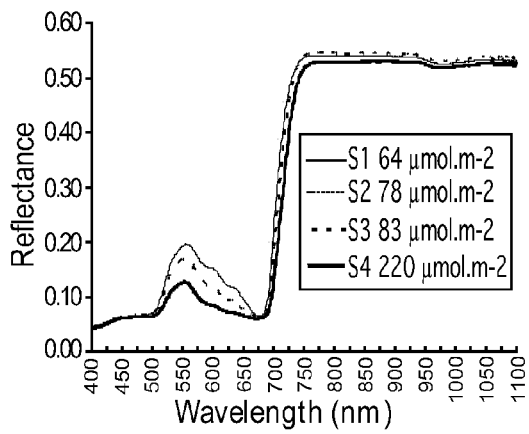
FIGS. 7A-7F show graphs of the reflectance spectrum (A), the reflectance difference (B), sensitivity based on reflectance (C), sensitivity based on Ch a (D), sensitivity based on Ch b (E) and sensitivity based on Ch a+Ch b (F) of four poplar leaves with chlorophyll contents of 64, 78, 115 and 220 μmol·m$^{-2}$, respectively.
Figure 7D:
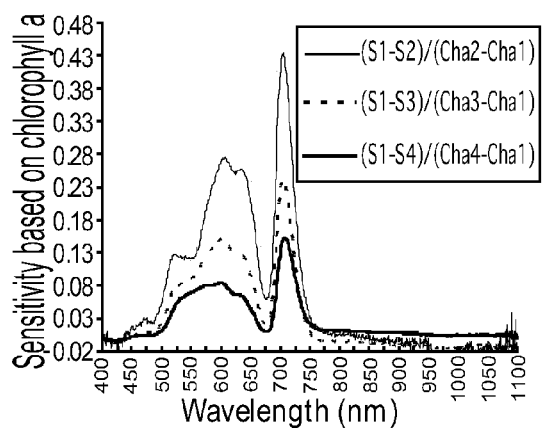
Figure 7B:
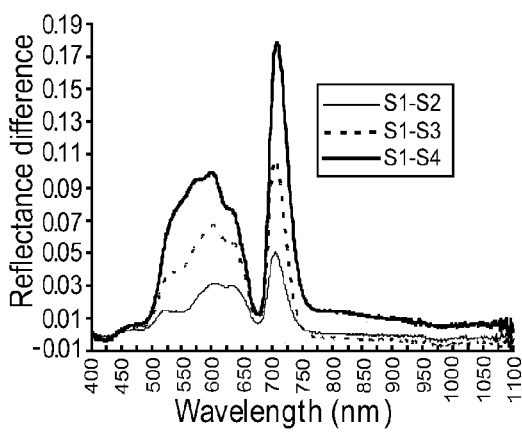
Figure 7E:
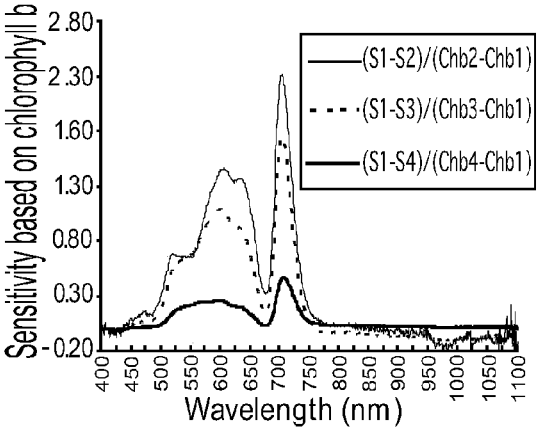
Figure 7C:
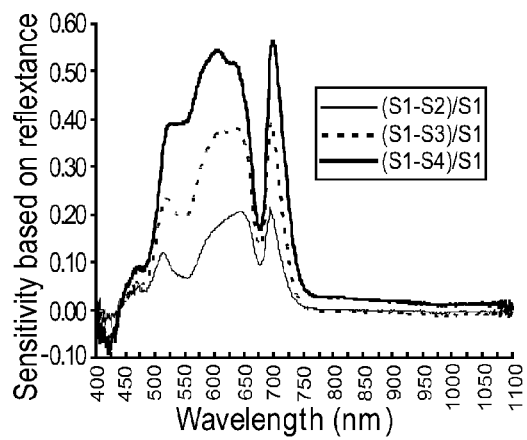
Figure 7F:
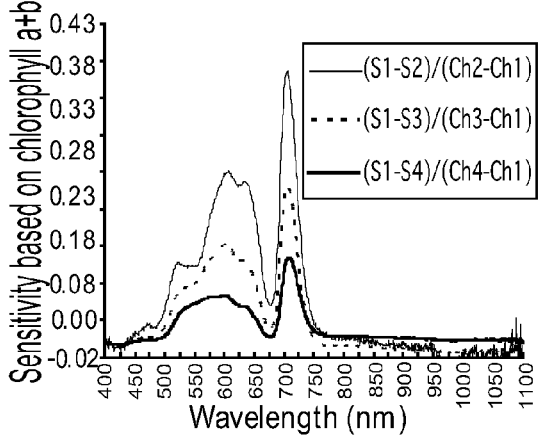

The reflectance spectra of 4 'Fuji' apple leaves (with chlorophyll contents of 109, 148, 229 or 336 μm·m$^{-2}$), 4 poplar leaves (with chlorophyll contents of 64, 78, 15 or 220 μm·m$^{-2}$) and 4 almond leaves (with chlorophyll contents of 57, 83, 123 or 221 μm·m$^{-2}$) are shown in FIGS. 6A, 7A and 8A, respectively. In the original reflectance spectral curves, there is only one peak of reflectance for leaves with different chlorophyll contents, which is in the visible wavelength range of 550-560 nm (FIGS. 6A, 7A and 8A). After the reflectance values of the leaves with different chlorophyll contents were transformed into reflectance differences, there were two peaks observed in the curve: one is in NIR range (710-720 nm) and the other is in visible range (560-600 nm). However, the peak in the NIR range was larger but much narrower than the peak in the visible range (FIGS. 6B, 7B and 8B).

After the reflectance value of leaves was transformed into wavelength sensitivity, the trends of the curves of the wavelength sensitivity based on either reflectance or 100 μm·m$^{-2}$ Ch a, Ch b or Ch a+b difference was very similar. There were two peaks in the curve that are very similar to the curve of the reflectance difference: one is in NIR range (706-716 nm) and the other is in visible range (560-600 nm). These results indicated that both spectral reflectance and wavelength differences could be used for the selection of the optimum wavelength for reflectance chlorophyll assessment in fresh leaves. However, the wavelength sensitivity based on 100 μm·m$^{-2}$ Cha, Ch b or Ch a+b difference was more meaningful for the optimum wavelength selection than the reflectance difference because the wavelength sensitivity was based on the difference of chlorophyll content, whereas the reflectance difference alone could not verify whether the difference was caused by the chlorophyll content difference.

FIGS. 6A-6F (four 'Fuji' apple leaves), FIGS. 7A-7F and FIGS. 8A-8F show graphs of the reflectance spectrum (A), the reflectance difference (B), sensitivity based on reflectance (C), sensitivity based on Ch a (D), sensitivity based on Ch b (E) and sensitivity based on Ch a+Ch b. The reflectance spectrum, reflectance difference and wavelength sensitivity were determined for four 'Fuji' apple leaves with chlorophyll content 109, 148, 229, 336 μmol·m$^{-2}$, respectively. The reflectance difference (B) was computed by subtracting the reflectance of leaves S2, S3, S4 from S1, respectively. Sensitivity based on reflectance (C) was computed by dividing the reflectance of S1 from the reflectance difference in (B). Sensitivity based on Ch a (D) was computed by dividing the Ch a difference between S2, S3, S4 and S1 from the reflectance difference in (B), then multiplying by 100. Sensitivity based on Ch b (E) was computed by dividing the Ch b difference between S2, S3, S4 and S1 from the reflectance difference in (B), then multiplying by 100. Sensitivity based on Ch a+b (F) was computed by dividing the Ch a+b difference between S2, S3, S4 and S1 from the reflectance difference in (B), then multiplying by 100.

Although the wavelengths for the peaks of reflectance (FIGS. 6A, 7A and 8A), reflectance difference (FIGS. 6B, 7B and 8B) and wavelength sensitivity (FIGS. 6C-6F, 7C-7F, and 8C-8F) were different for the plants or genotypes analyzed, however within the same genotype, e.g., either 'Fuji' apple, poplar or almond, the peak corresponding wavelengths in either the visible or NIR range for either the curve of reflectance, reflectance difference or wavelength sensitivity for the leaves with different chlorophyll contents are the same. These results indicate that, within the same genotype, the optimum wavelengths used for measuring chlorophyll contents were the same.

2. $R^2$ Between the Reading of Reflectance and Chlorophyll Contents at Each Wavelength Simple linear regressions and $R^2$ between the reflectance reading and chlorophyll contents (Chl a, Chl b and Ch a+b) were determined by using linear-least-squares-fit for each wavelength from 300 nm to 1100 nm with 1 nm interval. The $R^2$ curves indicate the relationship between reflectance values and leaf chlorophyll contents at different wavelength can be used for chlorophyll assessment (FIG. 9). The accuracy for determining chlorophyll content at each corresponding wavelength is greater with increasing $R^2$ value. There are three $R^2$ peaks that fall in the range of UV (380-440 nm), visible (520-600 nm), and NIR (690-740 nm), respectively. The $R^2$ of the three peaks and the corresponding wavelengths in the UV, visible and NIR for Chl a, Chl b and Ch a+b in 'Fuji' apple, poplar and almond leaves are listed in Table 5. The coefficient of determinations in the peak of NIR range for Ch a, Ch b, and Ch a+b are much larger than that in the peak of visible and the UV ranges in the leaf of 'Fuji' apple and poplar. For almond leaf the coefficient of determinations in the peak of visible range are slightly larger than in the NIR range, however the peaks in both ranges are larger than the peak in UV range. The largest $R^2$ and the corresponding wavelength for measuring chlorophyll (Ch a, Ch b or Ch a+b) in different plant leaves are different (Table 5). The wavelength for measuring the different chlorophylls (Ch a, Ch b and Ch a+b) within the leaves of the same plant were also different. The $R^2$ and the corresponding wavelengths of Ch a+b was between the $R^2$ and the corresponding wavelength of Ch a and Ch b, but tend to be closer to the $R^2$ and the corresponding wavelength of Ch a. This is because about 80% total chlorophyll is in the form of Ch a in the plant leaves.

TABLE 5

$R^2$ peaks and the corresponding wavelength for Cha, Ch b and Ch a + b in the leaf of 'Fuji' apple, poplar and almond leaves

| Species | Chlorophylls | UV range | | Visible range | | NIR range | |
| --- | --- | --- | --- | --- | --- | --- | --- |
| | | Wavelength (nm) | $R^2$ | Wavelength (nm) | $R^2$ | Wavelength (nm) | $R^2$ |
| 'Fuji' apple | Ch a | 412 | 0.5264 | 552 | 0.7785 | 720 | 0.9198 |
| | Ch b | 390 | 0.4759 | 550 | 0.7225 | 717 | 0.8465 |
| | Ch a + b | 410 | 0.5236 | 552 | 0.7695 | 720 | 0.9072 |
| Poplar | Ch a | 422 | 0.7474 | 581 | 0.9497 | 715 | 0.9579 |
| | Ch b | 423 | 0.6134 | 563 | 0.7440 | 730 | 0.7801 |
| | Ch a + b | 422 | 0.7331 | 574 | 0.9166 | 720 | 0.9352 |

TABLE 5-continued $R^2$ peaks and the corresponding wavelength for Cha, Ch b and Ch a + b in the leaf of 'Fuji' apple, poplar and almond leaves

| | | UV range | | Visible range | | NIR range | |
|---|---|---|---|---|---|---|---|
| Species | Chlorophylls | Wavelength (nm) | $R^2$ | Wavelength (nm) | $R^2$ | Wavelength (nm) | $R^2$ |
| Almond | Ch a | 420 | 0.2632 | 549 | 0.8740 | 710 | 0.8678 |
| | Ch b | 420 | 0.3121 | 558 | 0.8256 | 710 | 0.8144 |
| | Ch a + b | 420 | 0.2757 | 549 | 0.8737 | 710 | 0.8667 |

3. $1^{st}$ Derivative of Reflectance

Figure 9A:
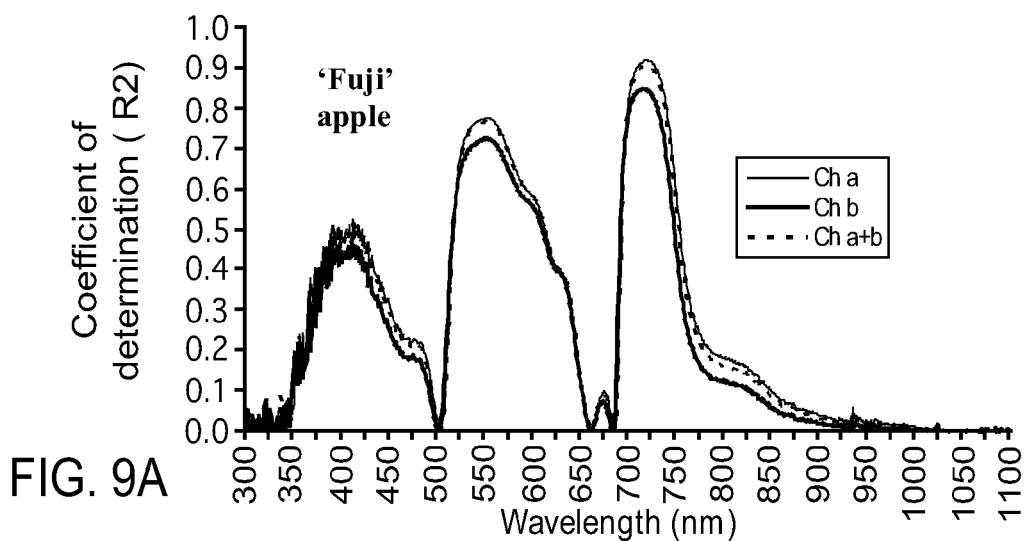
FIGS. 9A-9C show graphs of the Coefficients of determination ($R^2$) between the reading of reflectance and chlorophyll content (Ch a, Ch b and Ch a+b) at each wavelength in 60 leaves of 'Fuji' apple, poplar and almond, respectively.
Figure 9B:
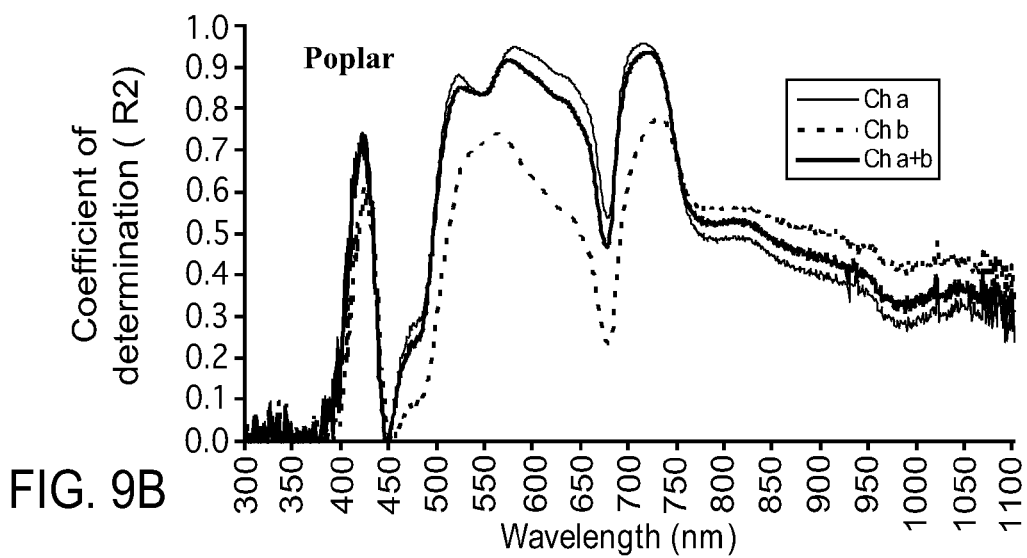
Figure 9C:
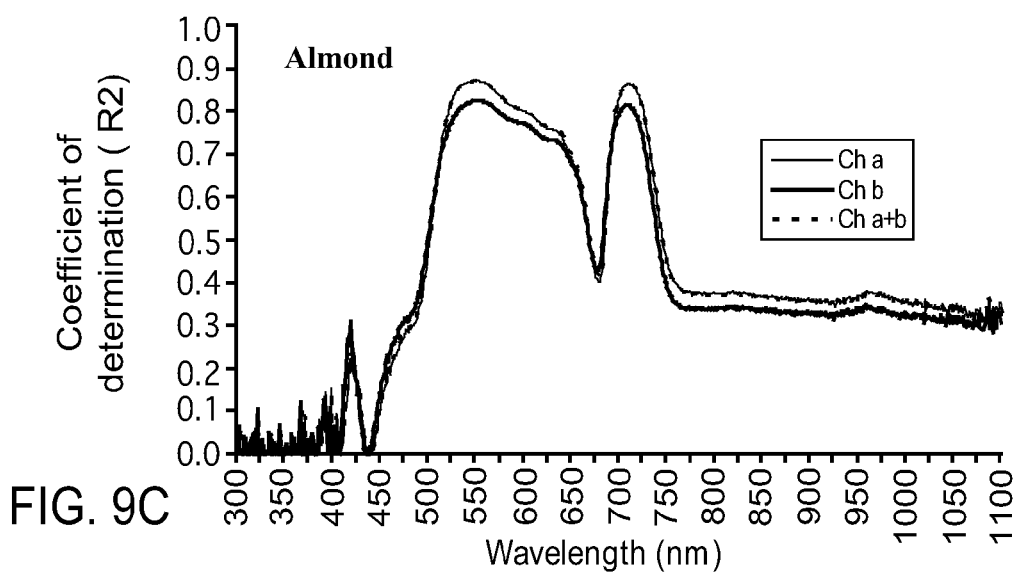
Figure 10A:
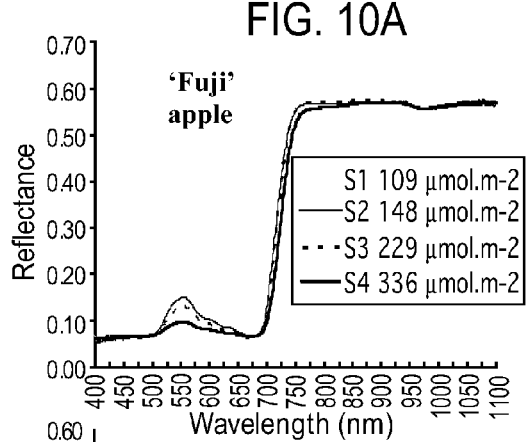
FIGS. 10A-10F show graphs of the reflectance spectrum (A-C) and their 1$^{st}$ derivatives (D-F) for leaves of 'Fuji' apple (chlorophyll contents of 109, 148, 229 and 336 μm·m$^{-2}$), poplar (chlorophyll contents of 64, 78, 15 and 220 μm·m$^{-2}$) and almond (chlorophyll contents 57, 83, 123 and 221 μm·m$^{-2}$), respectively.
Figure 10B:
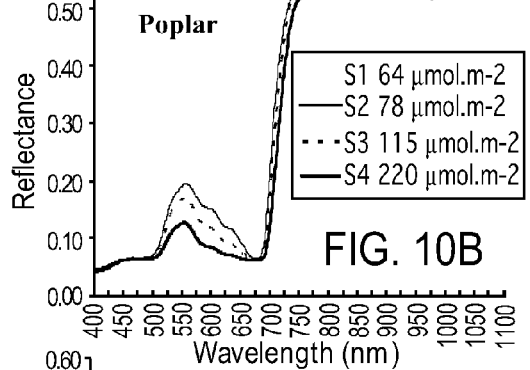
Figure 10C:
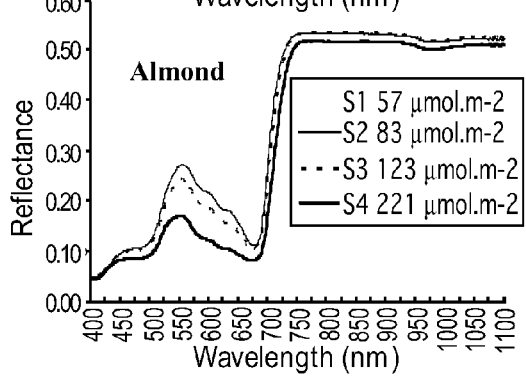
Figure 10D:
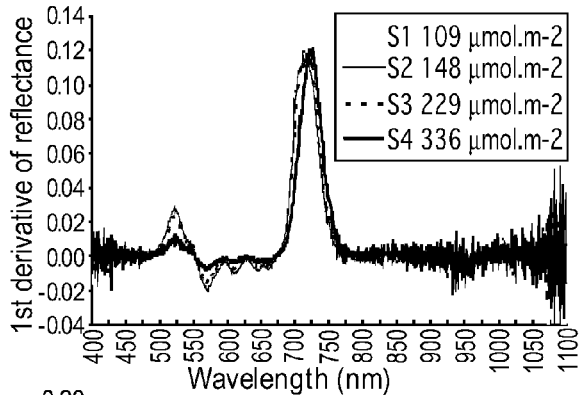
Figure 10E:
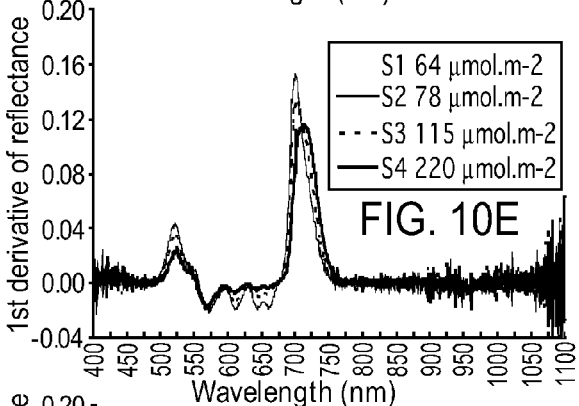
Figure 10F:
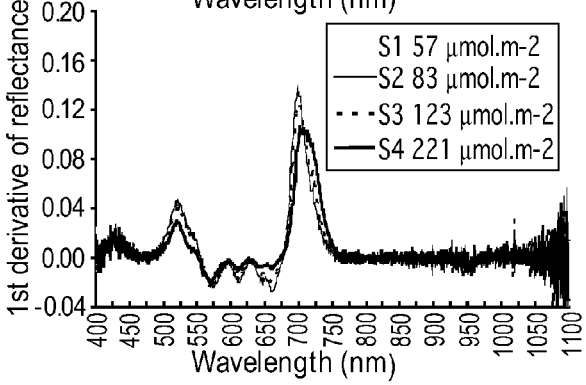

In the original spectrum there was only one reflectance peak in the visible range (550-560 nm) for apple, poplar or almond leaves with different chlorophyll contents, respectively (FIGS. 10A, 10B and 10C). After $1^{st}$ derivative transformation of reflectance, there were five peaks in the transformed spectrum (FIGS. 10D, 10E, 10F). In comparison with the curve wavelength sensitivity, however, there was only the peak in the NIR range had a similar trend in comparison with the wavelength sensitivity (FIGS. 6C-6F, 7C-7F, and 8C-8F) and $R^2$ (FIGS. 9A, 9B and 9C); whereas the other four peaks showed no relationship to the chlorophyll content of the leaves. The peak corresponding to the wavelengths of the $1^{st}$ derivative of reflectance in the NIR range within the same genotype with different chlorophyll contents was different. This differed from the curves of the reflectance difference (FIGS. 6B, 7B and 8B) and wavelength sensitivity (FIGS. 6C-6F, 7C-7F, and 8C-8F), in which the peak corresponding wavelengths were the same for chlorophyll assessment within the same genotype for the leaves that differed in chlorophyll content.

Figure 11A:
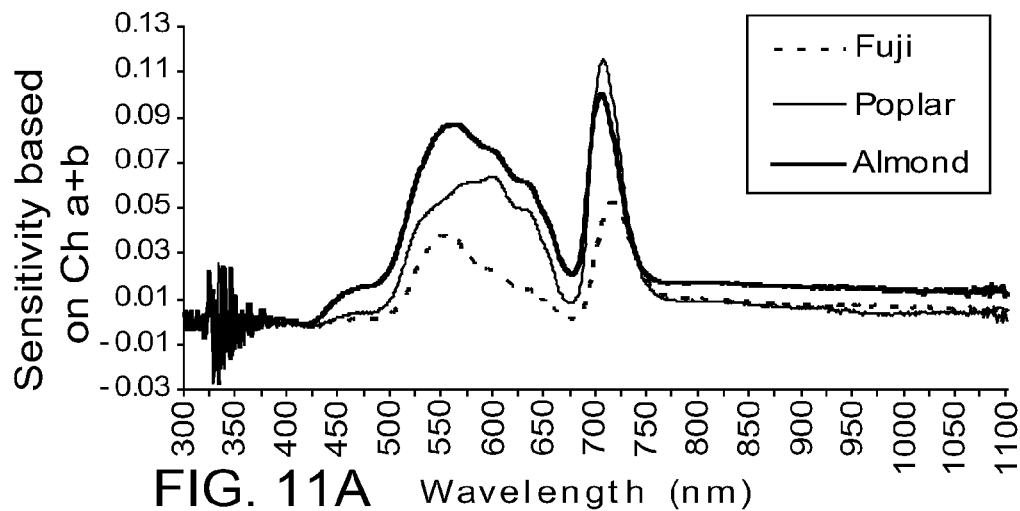
FIGS. 11A-11C show graphs of wavelength sensitivity (A), $R^2$ (B) and 1$^{st}$ derivative of spectrum (C), of 'Fuji' apple, poplar and almond leaves.
Figure 11B:
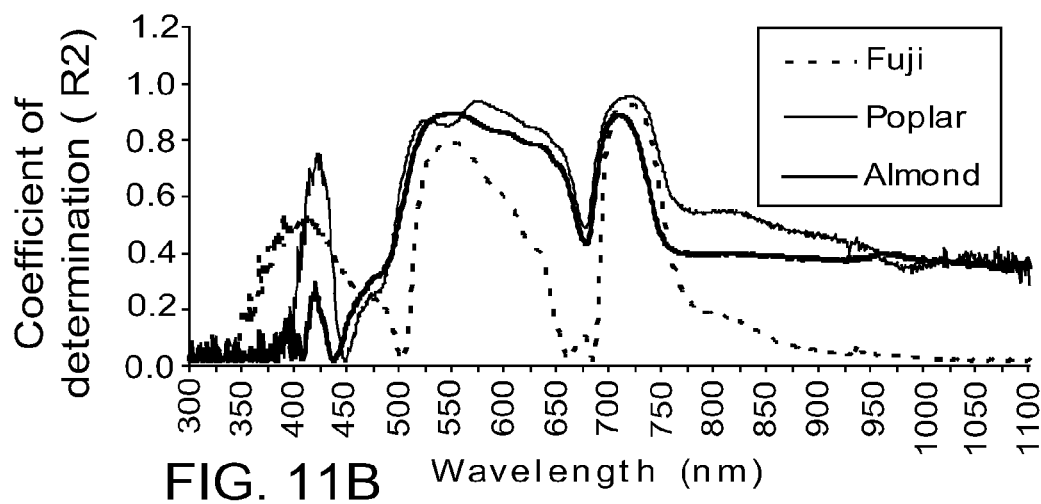
Figure 11C:
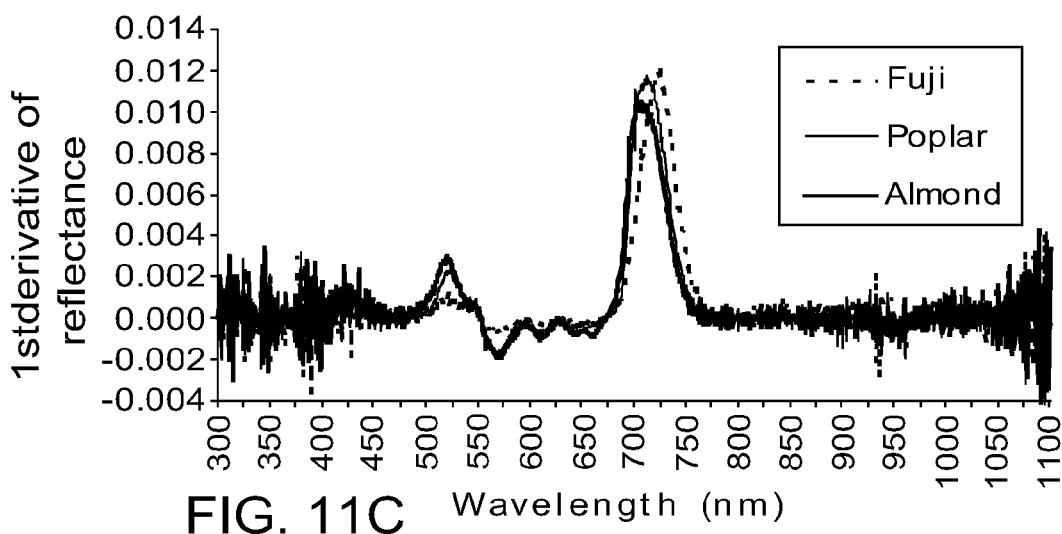

4. Comparisons of $R^2$, Wavelength Sensitivity and $1^{st}$ Derivative in Optimum Wavelength Determination The curves obtained for reflectance $1^{st}$ derivative, wavelength sensitivity and $R^2$ of total chlorophyll for 'Fuji' apple, poplar and almond at different wavelength are shown in FIG. 11. There are two peaks related to leaf chlorophyll content in the curves for $R^2$ and wavelength sensitivity, respectively. One peak was in the visible range and the other in the NIR range. In contrast the curve for the $1^{st}$ derivative showed only one peak related to leaf chlorophyll content, which was in the NIR range (FIGS. 11A, 11B and 11C). Generally the peak obtained in the NIR range determined by either $R^2$ or wavelength sensitivity was higher than the peak in the visible range. The range of the peak in the NIR region of the spectra obtained by different methods ($R^2$, wavelength sensitivity or $1^{st}$ derivative) were roughly in the same range of 690-750 nm. However, the apexes of the curves related to the optimum wavelengths obtained by different methods for measuring chlorophyll within the same plant leaves were different. In the NIR range, the peak related the optimum wavelengths identified by $R^2$ for measuring chlorophyll in 'Fuji' apple; poplar and almond are 717, 720 and 710 nm, respectively; however the optimum wavelengths identified by wavelength sensitivity for measuring chlorophyll in 'Fuji' apple, poplar and almond were 717, 708 and 705 nm, respectively; whereas the $1^{st}$ derivative identified the optimum wavelengths for the same samples were 726, 713 and 702 nm, respectively (FIGS. 11A, 11B and 11C). In the visible range the optimum wavelengths identified by $R^2$ for measuring chlorophyll in 'Fuji' apple, poplar and almond were 552, 574 and 549 nm, respectively; however the optimum wavelengths identified by wavelength sensitivity for the same samples were 558, 599 and 564 nm, respectively (FIGS. 11A and 11B).

In comparisons with the optimum wavelengths obtained by using $R^2$, the optimum wavelengths obtained by using either wavelength sensitivity or $1^{st}$ derivative shifted to either higher or lower wavelengths. Unfortunately, there was no consistent trend in the direction of the shift. The shift may cause some errors in deciphering the optimum wavelength.

Figure 12A:
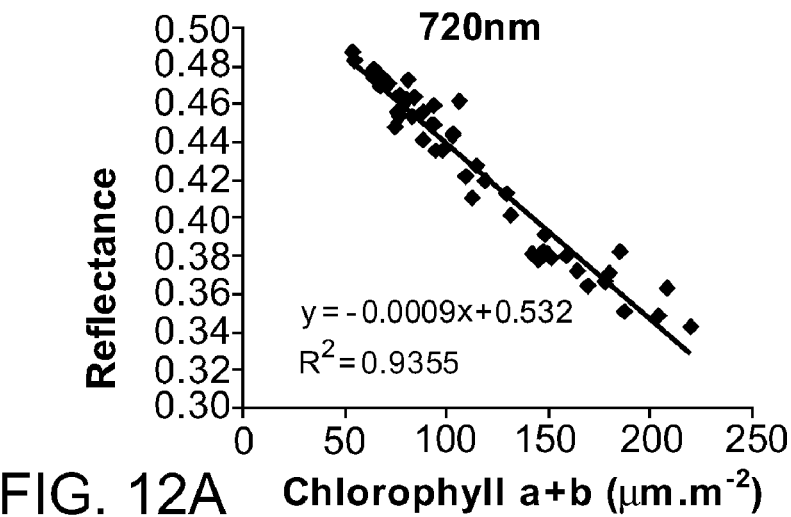
FIGS. 12A-12C show graphs of the simple-linear-regression curve fit between the wavelength reading and total chlorophyll contents in 48 poplar leaves at the optimum wavelengths identified by $R^2$ (A, 720 nm), wavelength sensitivity (B, 708 nm) and 1$^{st}$ derivative (C, 713 nm).
Figure 12B:
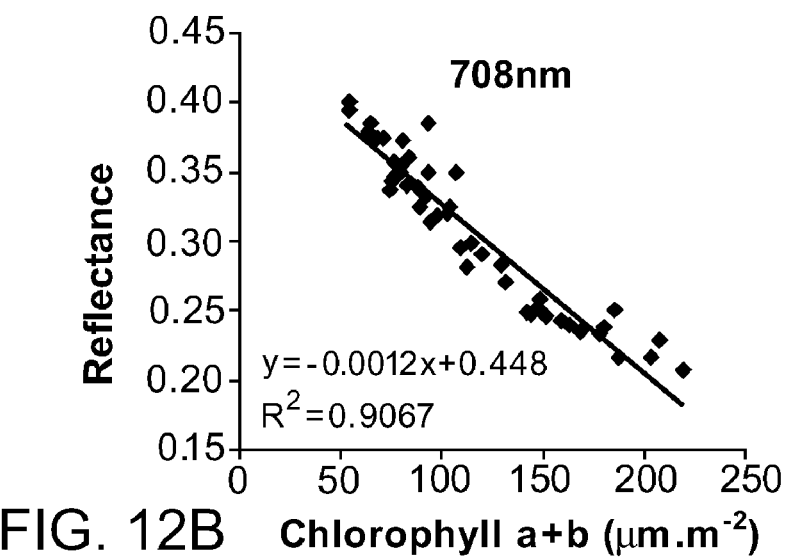
Figure 12C:
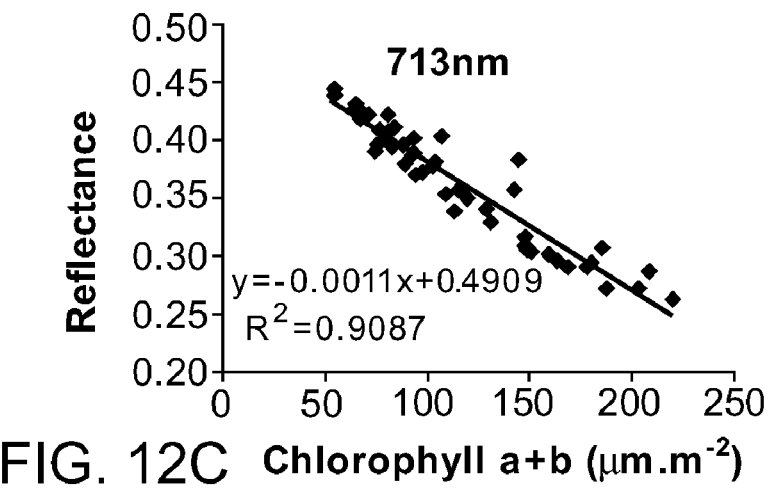

For example, the optimum wavelengths selected for measuring total chlorophyll (Ch a+b) by the methods of $R^2$, wavelength sensitivity and 1st derivative were 720, 708 and 713 nm, respectively. The fitness and $R^2$ of simple-linear-regression at the optimum wavelengths selected by different methods indicate that the wavelength 720 nm selected by using $R^2$ is better than wavelength 708 nm selected by wavelength sensitivity and 713 nm selected by using 1st derivative (FIGS. 12A, 12B and 12C). These results indicate that wavelength 708 nm selected by wavelength sensitivity and 713 nm selected by 15 derivative were not the optimum wavelengths for leaf total chlorophyll assessment.

Discussion

Chlorophylls are the dominant photosynthetic pigments in green plants and assessment of their concentration in foliage can provide an estimate of the potential photosynthetic capability of the leaves (Buschmann et al 1994, Pinar and Curran 1996, Carter 1998). There are several techniques for assessing leaf chlorophyll concentration by either reflectance or transmittance non-destructively. However the most common methods for estimating leaf chlorophyll contents are either by using chlorophyll related wavelength (i.e., 550 698, 692 or 695 nm) alone (Thomas and Gausman 1977, Jacquemoud and Baret 1990, Cater 1994, 1998, Moran and Moran 1998); or by using the chlorophyll related wavelength in combination with the chlorophyll insensitive wavelength at the form of wavelength ratio (i.e., R698/R760) or some specific algorithm like $(R_{800}-R_{445})/(R_{800}-R_{680})$ (Moran et al. 2000, Peñuelas et al 1995). Finding the optimum wavelength used for chlorophyll assessment is a challenge and there is no easy and reliable method reported in the literature that can be used for determining the optimum wavelength for measuring chlorophyll by spectral methods.

Derivatives are a very useful analytical tool for characterizing a spectral band that is overlapped by other bands with different half-widths. The $1^{st}$ derivative of the spectra have been used widely in chlorophyll related wavelength selection and indices development (Curran et al 1990, Dixit and Ram 1985, Gitelson et al 1996, 2003, Morrey 1968, Richardson et al 2002). The $1^{st}$ derivative has been successfully used for finding the red edge for chlorophyll assessment. However, derivative changed the original peak form by either creating some non-meaningful peaks or eliminating some important peaks that maybe chlorophyll related. After the $1^{st}$ derivative transformation of reflectance, there were five peaks in the transformed spectra (FIGS. 10D, 10E, 10F). However, only the peak in the NIR range had the similar trends in comparison with the peaks identified by wavelength sensitivity (FIGS. 6C-6F, 7C-7F, and 8C-8F) or $R^2$ (FIGS. 9A, 9B and 9C). The other four peaks showed no relationship to the chlorophyll contents. Furthermore, the optimum wavelengths selected by using $1^{st}$ derivative shifted either to higher or lower wavelengths than the optimum wavelength. Although the $1^{st}$ derivative can be used to roughly determine the red edge spectral band for chlorophyll assessment (Dixit and Ram 1985), the $1^{st}$ derivative alone is difficult to use for determining the optimum wavelength for chlorophyll assessment in our result (FIG. 11C and FIG. 12).

Wavelength sensitivity explains how sensitive the specific wavelength is in measuring chlorophyll. Although the optimum wavelength selected according to wavelength sensitivity shifted away from the optimum wavelength position (FIGS. 11A and 11B), however the results from wavelength sensitivity is much more meaningful for optimum wavelength selection than $1^{st}$ derivative because wavelength sensitivity is based on chlorophyll content and the sensitivity difference based on the difference of chlorophyll content, whereas the $1^{st}$ derivative could not verify whether the spectral difference was caused by difference of chlorophyll content (FIGS. 6D-6F, 7D-7F and 8D-8F). Within the same genotype (i.e., 'Fuji' apple, poplar or almond) the visible or NIR peak related optimum wavelength for the leaves with different chlorophyll contents were in the same spectral band (FIGS. 6D-6F, 7D-7F and 8D-8F). Therefore the optimum wavelength for chlorophyll assessment was determined by wavelength sensitivity can be used for leaves within the same genotype that have different chlorophyll contents. Whereas the $1^{st}$ derivative shifts the overlapped peaks of the leaves with different chlorophyll contents from the same spectral band to different spectral band (FIGS. 10D, 10E and 10F). Optimum wavelength shifts give us a phantasm that the leaves with different chlorophyll contents have different optimum wavelengths (FIGS. 10D, 10E and 10F). This is inconsistent with the hypothesis that, if we ignore the inference factors, the reflectance difference is only affected by leaf chlorophyll contents. In other words, the wavelength selected for leaf chlorophyll assessment is based on the assumption that the reflectance change only affected by chlorophyll content and the same optimum spectral band can be used to assessment chlorophyll in the leaves with different chlorophyll contents.

Coefficient of determination ($R^2$) is an essential indicator and a measure of goodness-of-fit of linear regression and a measure of regression accuracy (Chatterjee et al. 2000). Theoretically, the optimum wavelength(s) selected for non-destructive chlorophyll measurement should be based on having the highest wavelength sensitivity and highest $R^2$ between spectral wavelength readings and leaf chlorophyll contents. Higher $R^2$ is usually associated with higher wavelength sensitivity in measuring leaf chlorophyll. In order to insure that the optimum wavelength identified has both higher $R^2$ and higher wavelength sensitivity, it is best to use simple linear $R^2$ in combination with wavelength sensitivity for determining the optimum wavelength. Our results indicate that the combination of $R^2$ and wavelength sensitivity was a reliable method for determination of the optimum wavelength for chlorophyll measurement as well as for other pigments assessment for both transmission (result not shown) and reflectance spectroscopy.

Part V

Optimum Wavelength Identification and Algorithm Evaluation for Non-Destructive Chlorophyll Reflectance Assessment in Poplar Fresh Leaves Poplar (UCC-1, a hybrid of *Populus trichocarpa*×*P. deltoides*, Union Camp, Princeton, N.J.) leaves with different chlorophyll (Chl) contents from 160 to 659 µmol·m$^{-2}$ created by N fertigation were scanned by using Li-1800 spectroradiometer (Li-Cor Inc., Lincoln, Nebr.) from 300 to 1100 nm with 1 nm interval to measure the spectral reflectance. After scan the contents of leaf Chl a, b and a+b were tested to analyze Chl wavelength sensitivity and to develop simple linear regression between reflectance and Chl contents. The regression coefficient determination ($R^2$), root mean square error (RMSE) and Chl wavelength sensitivity results indicated that two wavebands, NIR 700-740 nm and visible 550-615 nm, had larger $R^2$, higher wavelength sensitivity and smaller RMSE and could be used as the optimum wavelength for Chls (Chl a, Chl b and Chl a+b) assessment in poplar leaves. Among 20 proposed indices tested, the $R^2$ and the corresponding RMSE differed greatly. The main reason was that Chl related wavelength in the proposed indices was far away from the Chl related optimum wavelength (OW). Chl related OW identification is very important for indices development. When the Chl related wavelengths (675, 695, 698, 700, 705 or 710 nm) in different proposed indices were replaced by the Chl related OW 580, 563 and 574 nm in green or 715, 730 and 720 nm in NIR for Chl a, Chl b or Chl a+b, respectively, all the modified indices had larger $R^2$ and smaller RSME. The optimum indices developed for Chl assessment can be simplified into $R_{750-1000}/R_{ow}$, $(R_{750-1000}-R_{ow})/(R_{750-1000}+R_{ow})$, $R_{430-490}/R_{ow}$ and $(R_{430-490}-R_{ow})/(R_{430-490}+R_{ow})$, in which the OWs are wavelength 580, 563 and 574 nm in green or 715, 730 and 720 nm in NIR for Chl a, Chl b or Chl a+b, respectively. Although the Chl related OWs differed among species, cultivar and Chls (Chl a, Chl b and Chl a+b), our test results indicated that wavelength 700-740 nm and 540-580 nm could be used as the Chl related OW for a variety of species, respectively. The combination of the Chl related OW with the reference wavelength (RW) in either 430-490 nm or 750-1100 nm could be used as the optimum indices for Chl assessment in a variety of species, and could be simplified as $R_{rw}/R_{ow}$ and $(R_{rw}-R_{ow})/(R_{rw}+R_{ow})$.

Introduction

The chlorophylls, Chl a and Chl b, are essential pigments for the conversion of light energy to stored chemical energy (Gitelson et al. 2003, Richardson et al. 2002). From both physiological and applied perspectives leaf Chls are important on several aspects (Peñuelas and Filella 1998, Richardson et al. 2002). First, the amount of solar radiation absorbed by a leaf is largely a function of the foliar concentration of photosynthetic pigments, and thus Chl content can directly limit photosynthetic potential and primary production (Curran et al. 1990, Filela et al 1995, Peñuelas et al 1995a). Second, most of leaf nitrogen is incorporated in Chl; therefore Chl content gives an indirect estimation of nutrient status (Filella et al 1995, Moran et al. 2000). Third, leaf Chl content is closely related to plant stress (Carter and Knapp 2001, Hendry 1987, Peñuelas and Filella 1998)

Traditionally, leaf extraction with organic solvents and spectrophotometric determination in solution required for Chl analysis with wet chemical methods (Arnon 1949, Lichtenthaler 1987). Recently, the alternative nondestructive optical methods, based on the absorbance and/or reflectance of light by the intact leaf, have been developed (Curran et al. 1990, Adams et al. 1999, Datt 1999a, Gamon and Surfus 1999, Markwell et al. 1995). These optical methods are non-destructive, simple to use, fast and can be used in the field (Buschmann and Nagel 1993, Buschmann et al. 1994, Gitelson and Merzlyak 1994b, Gitelson et al. 1996a, 1996b, Markwell et al. 1995). Most of the previous papers were focus on Chl related indices development or evaluation (Curran et al., 1990; Gitelson & Merzlyak, 1994, 1996; Gitelson et al., 1996a, 1996b, Blackburn 1998, Datt 1998, 1999a; Adams et al., 1999; Gamon & Surfus, 1999). There are many indices that have been developed for Chl non-destructive assessment in a variety of plants (Curran et al., 1990; Gitelson & Merzlyak, 1994, 1996; Gitelson et al., 1996a, 1996b, Blackburn 1998, Datt 1998, 1999a, 1999b; Adams et al., 1999; Gamon & Surfus, 1999). These proposed indices were developed either by using single Chl related wavelength (i.e., 550 698, 692 or 695 nm) alone (Thomas and Gausman 1977, Jacquemoud and Baret 1990, Cater 1994, 1998, Moran and Moran 1998) or by using Chl related wavelength in combination with Chl insensitive wavelength as the form of wavelength ratio (i.e., R698/R760) or some specific algorithm like $(R_{NIR}-R_{Red})/(R_{NIR}-R_{Red})$ (Moran et al. 2000, Penuelas et al 1995b, Richardson et al. 2002). However, these indices have rarely been tested using data from species other than those used in the formulation of the index (Richardson et al 2002), and there is no any index that can be used universally among various species. There are many reasons that the proposed indices are not applicable in different studies and among different species. However, the main reason, according to our study, is that the Chl related optimum wavelengths for measuring Chl used in one study differ from the optimum wavelengths used in the other studies because the optimum wavelengths vary among species or cultivar. The purpose of this study is to evaluate the importance of optimum wavelength selection in Chl related reflectance indices development.

Materials and Methods

Plant Materials

Poplar (UCC-1, a hybrid of *Populus trichocarpa×P. deltoides*, Union Camp, Princeton, N.J.) trees were grown in 7.2 L pots with a medium of 1 peat moss:2 pumice:1 sandy loam soil (v:v) in a lathhouse from 26 March to 5 June. Beginning from budbreak in early May, they were fertilized every 2 weeks with 10.7 mM N, using Plantexâ 20N-10$P_2O_5$-20$K_2O$ water-soluble fertilizer with micronutrients (Plantex Corp., Ontario, Canada). When the new shoots were approximately 15 cm long, plants were moved to full sunlight. Thereafter, they were fertilized weekly with Plantexâ for 3 weeks. Beginning on 30 June, plants were fertilized twice weekly with one of the six N concentrations (0, 2.5, 5, 7.5, 10, or 20 mM N from $NH_4NO_3$) by applying 300 ml of a modified Hoagland's solution to each pot until the end of September in two successive years.

Leaf Reflectance Spectrum

At the end of August, 12 fresh leaves from each N fertigation treatment plants were harvested and immediately placed into plastic bags for transport to the laboratory. Leaf discs taken with a 2.85 $cm^2$ cork borers were immediately scanned by using Li-1800 spectroradiometer (Li-Cor Inc., Lincoln, Nebr.) from 300 nm to 1100 nm with 1 nm interval to measure the spectral reflectance. Two scans were made per sample and then average. The reflectance spectrum for each scan was calculated as $R_\lambda$=leaf radiance at wavelength $\lambda$/reflectance standard radiance at wavelength $\lambda$, and was averaged across the two separate scans made on each leaf disc.

Chlorophyll and Other Leaf Pigment Analysis

After scan the leaf discs were then extracted in 80% (v/v) acetone at 4° C. in the dark for Chl content assessment. Absorptance of the extract was measured with a Shimadzu UV-visible spectrophotometer UV-1601. Total Chl was calculated according to Lichtenthaler and Wellburn (1983). The ranges of leaf total Chl contents for different N fertigation treatments are from 160 to 659 $\mu m \cdot m^{-2}$.

Simple Linear Regression Coefficient Determination ($R^2$) and Root Mean Square Error (RSME)

Simple linear regression between the reading of each wavelength and Chls (Chl a, Chl b or Chl a+b) was developed for wavelength from 300 nm to 1100 nm with 1 nm interval. The regression $R^2$ and RSME curves of Chl a, Chl b and Chl a+b were developed at each wavelength for optimum wavelength identification, respectively.

Wavelength Sensitivity

The reflectance curves for the poplar leaves with different Chl contents (185, 234, 337 or 659 $\mu mol \cdot m^{-2}$) were developed for wavelength from 300 nm to 1100 nm. The reflectance value for the leaf with Chl content of 234, 337 or 65911 $mol \cdot m^{-2}$ was then subtracted by that of the leaf with lowest Chl content of 185 $\mu mol \cdot m^{-2}$ at each measured wavelength to get the reflectance difference. The reflectance difference was then normalized by dividing the difference of Chl Chl a, Chl b and Chl a+b between the leaf with lowest Chl content (185 $\mu mol \cdot m^{-2}$) and the leaf with higher Chl content (234, 337 or 659 $\mu mol \cdot m^{-2}$) to produce the Chl a, Chl b or Chl a+b based sensitivity curve for optimum wavelength determination.

Leaf Reflectance Indices Calculations

In order to select the optimum indices, the reflectance spectra were transformed by using 20 published indices that have been recommended as excellent indicator of foliar Chl assessment (Table 6). These recommended indices include simple ratio (SR), normalized difference vegetation index (NDVI), photochemical reflectance index (PRI).

(1) The SR is calculated as the ratio of two single wavelengths. The SR is also called vegetation index (VI) if the ratio is between the NIR region and red region wavelengths (Andrew et al. 2002). Some indices targeted directly at either Chl a or Chl b, therefore the SR is called pigment specific simple ratio for Chl a (PSSR b) and Chl b (PSSR b) (Blackburn, 1998).

(2) NDVI is an index strongly correlated with leaf Chl content (Gamon et al. 1995; Peñuelas & Filella 1998, Richardson et al. 2002). It is a standard index used in remote sensing (Gamon and Qiu 1999). The NDVI is calculated as $(R_{NIR}-R_{red})/(R_{NIR}+R_{red})$. The most popular NDVI is calculated as NDVI=(R750−R675)/(R750+R675). The revised version of the NDVI is called Chl Normalized difference index (Chl NDI), which is better correlated with leaf Chl content and more sensitive to a wider range of Chl contents calculated as Chl NDI=(R750−R705)/(R750+R705) (Richardson et al. 2002, Gitelson and Merzlyak 1994b).

(3) PRI is an index of xanthophyll cycle pigment activity (Gamon et al. 1997, Gamon and Surfus 1999, Peñuelas and Filella 1998). Over short time spans (e.g., diurnally), PRI is correlated with both the epoxidation state of xanthophyll cycle pigments and photosynthetic radiation use efficiency (PRUE): PRUE=(net photosynthesis)/(incident photosynthetically active radiation (PAR) (Gamon et al. 1992, Peñuelas et al. 1995, Filella et al. 1995). Over longer time spans, or across species or sites, PRI is positively correlated with photosystem (PS) II efficiency as measured by Chl fluorescence and the chl:carotenoids ratio, which may itself be an indicator of photosynthetic efficiency (Sims and Gamon 2002).

(4) SIPI=(R800−R445)/(R800−R680), which is an index associate with the ratio of total carotenoids at wavelength 445 nm to Chl a at wavelength 680 nm (Moran et al. 2000, Peñuelas et al. 1995).

between the $R^2$ and the corresponding wavelength of Chl a and Chl b, but tend to be closer to the $R^2$ and the corresponding wavelength of Chl a. This is because about 80% total chlorophyll is in the form of Chl a in the plant leaves.

Figure 13A:
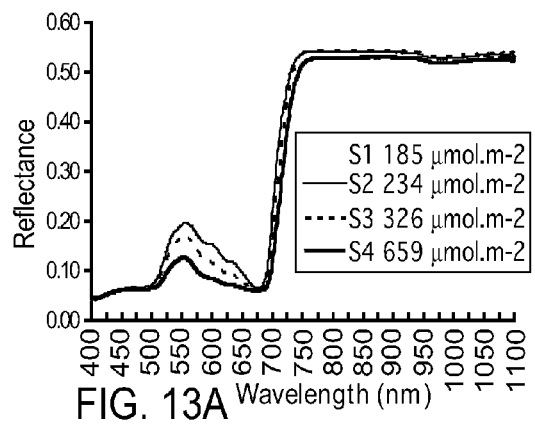
FIGS. 13A-13F show graphs of the original reflectance (A), coefficients of determination (B), RMSE (C) and wavelength sensitivity of chlorophylls (Chl a, Chl b and Chl a+b)) (D, E and F, respectively) at each wavelength from about 300 to about 1100 nm in poplar leaves.

The original reflectance spectra of 4 poplar leaves with Chl contents of 185, 234, 337 or 659 μmol·m$^{-2}$ were shown in FIG. 13A. In the original reflectance spectral curves, there

TABLE 6

Recommended indices used for on leaf level Chl assessment or canopy level in remote sensing

| No | Algorithms | Indices | Reference |
|----|------------|---------|-----------|
| 1 | $R_{750}/R_{700}$ | VI | Gitelson et al. 1996a |
| 2 | $R_{750}/R_{550}$ | VI | Gitelson et al. 1996a |
| 3 | $R_{850}/R_{710}$ | VI | Datt. 1999a |
| 4 | $R_{710}/R_{760}$ | VI | Carter 1993, 1994 |
| 5 | $R_{695}/R_{760}$ | VI | Carter 1993, 1994 |
| 6 | $R_{605}/R_{760}$ | VI | Carter 1993, 1994 |
| 7 | $R_{695}/R_{420}$ | VI | Carter 1993, 1994 |
| 8 | $R_{675}/R_{700}$ | VI | Chappelle et al 1992 |
| 9 | $R_{940}/R_{675}$ | VI | Carter 1994 |
| 10 | $R_{800}/R_{680}$ | VI | Blackburn 1999 |
| 11 | Chl a: $R_{800}/R_{675}$ | PSSR a | Blackburn, 1998 |
| 12 | Chl b: $R_{800}/R_{650}$ | PSSR b | Blackburn, 1998 |
| 13 | $(R_{800} - R_{445})/(R_{800} - R_{680})$ | SIPI | Moran et al. 2000, Peñuelas et al. 1995 |
| 14 | $(R_{850} - R_{710})/(R_{850} - R_{680})$ | NDVI | Datt, 1999 a |
| 15 | $(R_{800} - R_{700})/(R_{800} + R_{700})$ | NDVI | Gietelson and Merzlyak 1994 a and b |
| 16 | $(R_{800} - R_{680})/(R_{800} + R_{680})$ | NDVI | Blackburn 1998 |
| 17 | $(R_{750} - R_{675})/(R_{750} + R_{675})$ | NDVI | Gamon and Qiu 1999, Richardson and Berlyn 2002 |
| 18 | $(R_{531} - R_{570})/(R_{531} + R_{570})$ | PRI | Gamon et al. 1992, 1997, Peñuelas et al. 1995 |
| 19 | $(R_{750} - R_{680})/(R_{750} + R_{690})$ | NDVI | Richardson et al. 2002 |
| 20 | $(R_{750} - R_{705})/(R_{750} + R_{705})$ | Chl NDI | Gitelson and Merzlyak 1994a, Gamon and Surfus 999 |

Results

Optimum Wavelength Identification

Figure 13B:
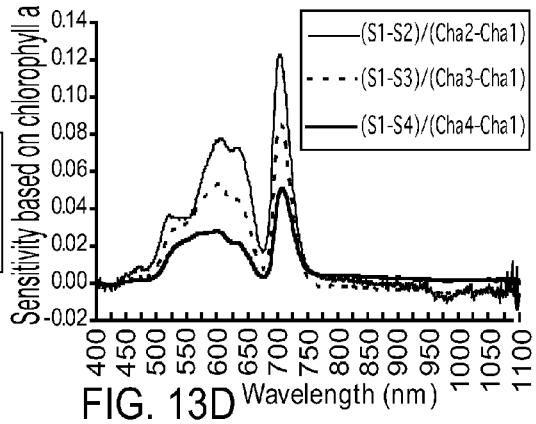
Figure 13C:
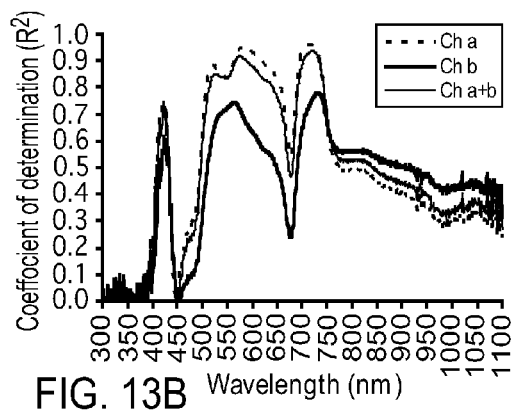
Figure 13D:
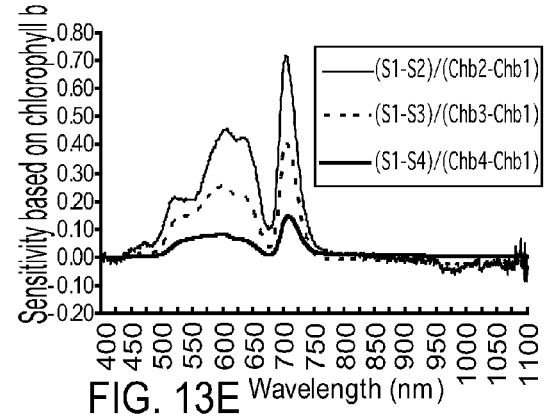
Figure 13E:
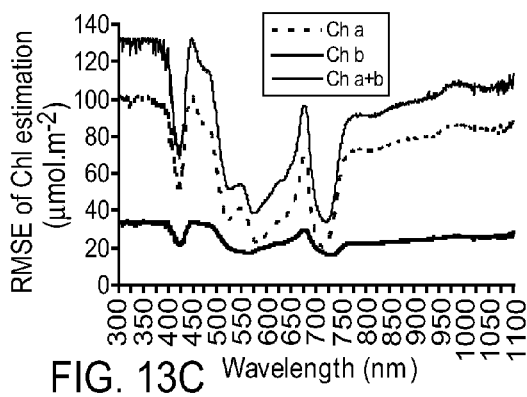
Figure 13F:
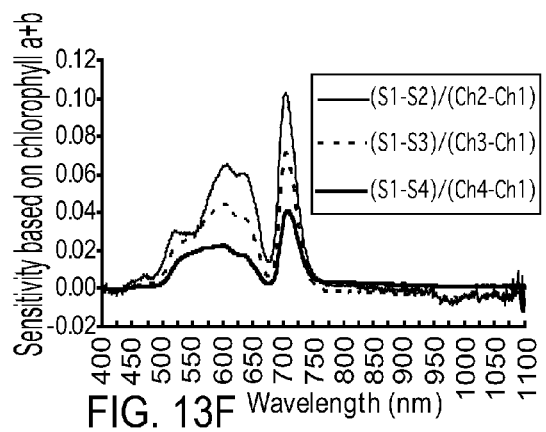
Figure 14A:
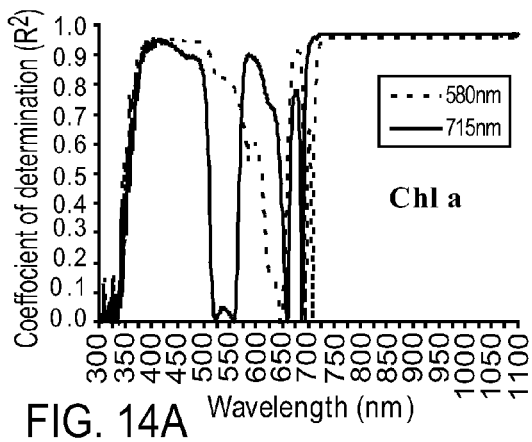
FIGS. 14A-14F show graphs of the coefficients of determination $R^2$ (A, B, and C) and RMSE (D, E, F) of Chl a, Chl b and Chl a+b estimated by $R_{300-1100}/R_{580}$, $R_{300-1100}/R_{715}$, $R_{300-1100}/R_{563}$, $R_{300-1100}/R_{730}$, $R_{300-1100}/R_{574}$ and $R_{300-1100}/R_{720}$, respectively.
Figure 14D:
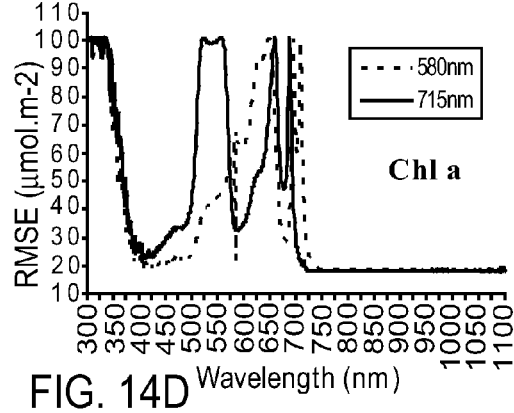
Figure 14B:
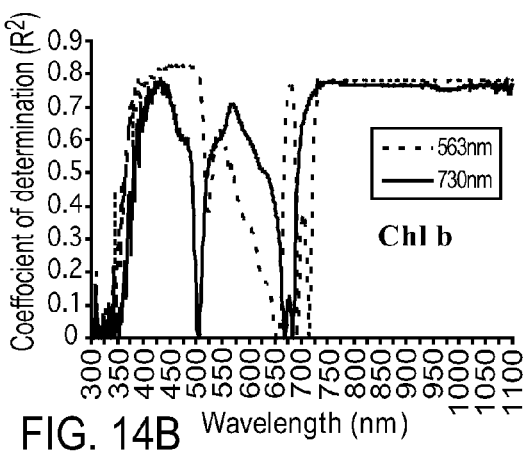
Figure 14E:
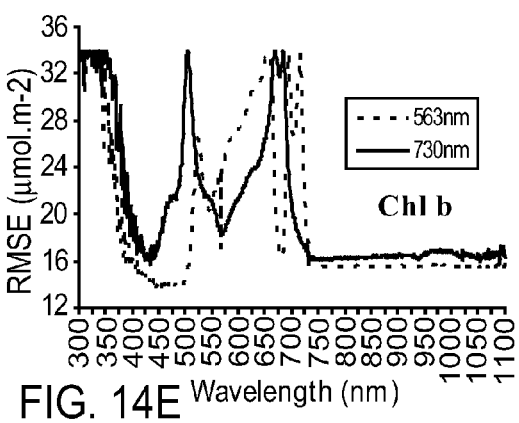
Figure 14C:
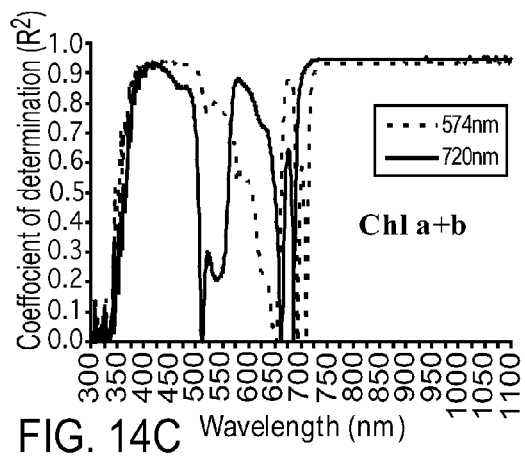
Figure 14F:
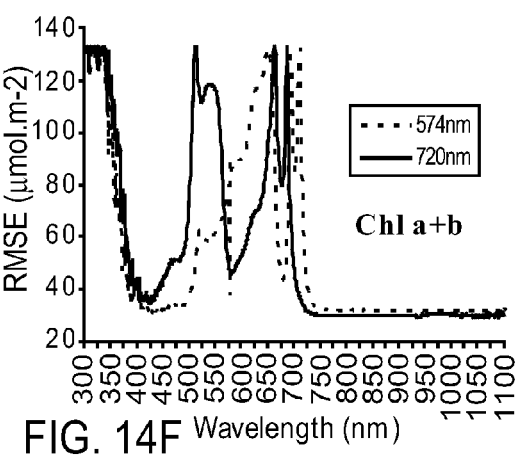
Figure 15A:
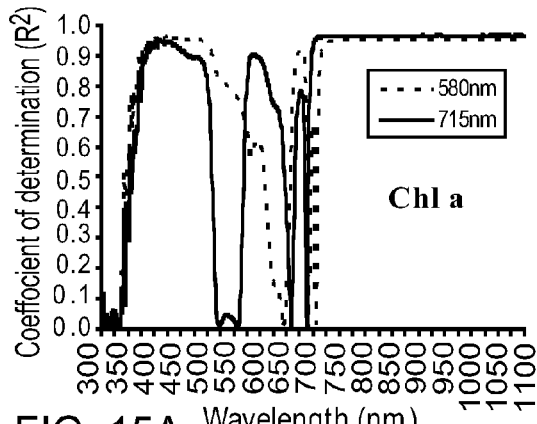
FIGS. 15A-15F show graphs of the coefficients of determination $R^2$ (A, B, and C) and RMSE (D, E and F) of Chl a, Chl b and Chl a+b estimated by $(R_{300-1100}-R_{580})/(R_{300-1100}-R_{580})$, $(R_{300-1100}-R_{563})/(R_{300-1100}-R_{563})$ and $(R_{300-1100}-R_{574})/(R_{300-1100}-R_{574})$ or by $(R_{300-1100}-R_{715})/(R_{300-1100}-R_{715})$, $(R_{300-1100}-R_{730})/(R_{300-1100}-R_{730})$ and $(R_{300-1100}-R_{720})/(R_{300-1100}-R_{720})$, respectively.
Figure 15D:
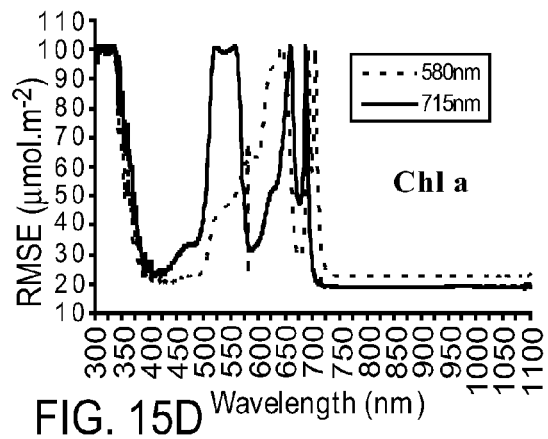
Figure 15B:
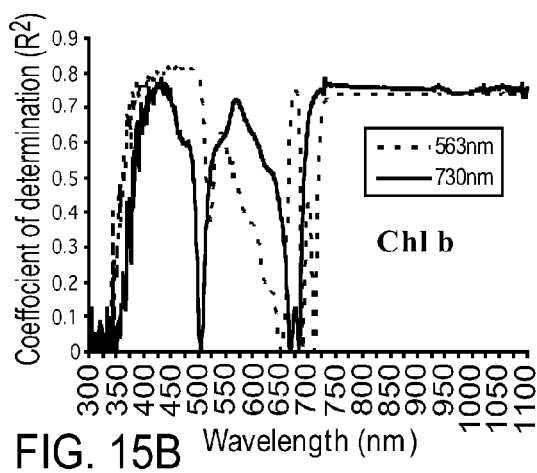
Figure 15E:
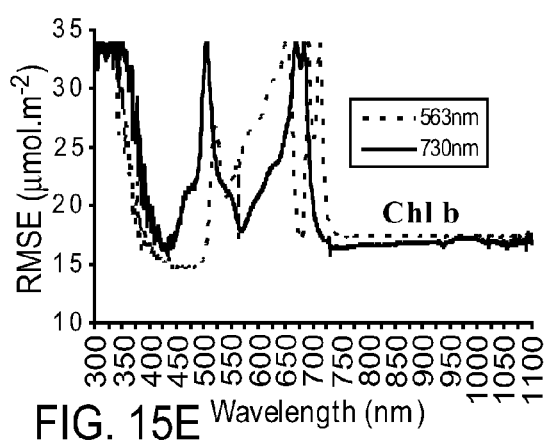
Figure 15C:
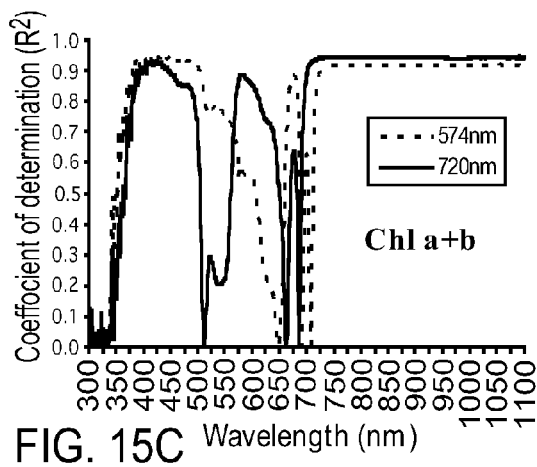
Figure 15F:
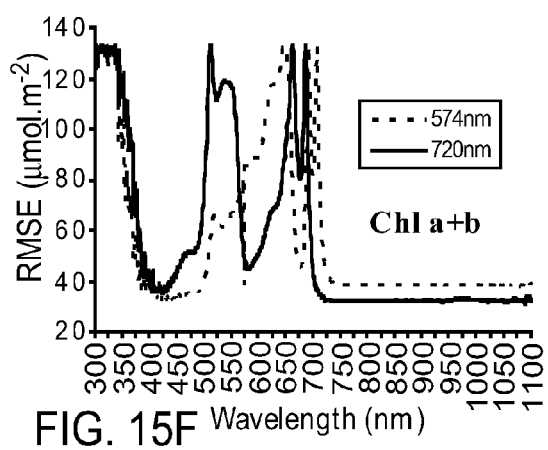

Simple linear regressions and $R^2$ between the reading of reflectance and Chl (Chl a, Chl b and Chl a+b) contents were determined by using linear-least-squares-fit for each wavelength from 300 nm to 1100 nm with 1 nm interval. There were three $R^2$ peaks (FIG. 13B) in the $R^2$ curves that fell in the range of UV (400-440 nm), visible (530-650 nm), and NIR (690-750 nm), respectively. These peaks related wavelength could be used for Chl assessment; however, higher $R^2$ related wavelength had smaller RMSE and better accuracy for Chl assessment (FIG. 13C). The coefficient of determinations in the peak of NIR and visible ranges for Chl a, Chl b, and Chl a+b were much larger than that in the peak UV range. The peak apexes corresponding wavelengths differed among Chls (Chl a, Chl b and Chl a+b) in both visible and NIR ranges. The $R^2$ and the corresponding wavelengths of Chl a+b was was only one peak in the visible range (green) of wavelength 530-580 nm. After the original reflectance transformed into wavelength sensitivity, there were two evident peaks, one in the NIR range of 685-730 nm and the other in the visible range of 560-650 nm, in the curve of Chl a, Chl b and Chl a+b, respectively (FIG. 13D-13F). The wavelength sensitivity in the peak of NIR range was much higher than that in the visible range. Larger $R^2$ with higher wavelength sensitivity indicated that the peak related wavelength in both NIR and visible ranges could be used as the optimum wavelength for Chl assessment. The range of optimum wavelengths for measuring Chl a, Chl b and Chl a+b were different in both visible and NIR; however most of the peaks for Chl a, Chl b and Chl a+b were overlapped each other (Table 7). The optimum wavelength selected from the overlapped wavelengths of 566-570 nm in the green or 710-730 nm in the NIR range could be used for accessing Chl a, Chl b and Chl a+b in poplar leave.

TABLE 7

Optimum wavelengths for Chl a, Chl b and total Chl assessment in poplar leaves

| | Visible range | | | NIR range | | |
|---|---|---|---|---|---|---|
| Chlorophylls | Wavelength (nm) | $R^2$ | RMSE | Wavelength (nm) | $R^2$ | RMSE |
| Chl a | 580 | 0.9497 | 25.82 | 715 | 0.9579 | 23.82 |
| | 565-615 | 0.9026-0.9497 | 31.46-25.82 | 700-730 | 0.9242-0.9579 | 23.82-28.91 |
| Chl b | 563 | 0.7440 | 14.72 | 730 | 0.7801 | 13.98 |
| | 550-570 | 0.7241-0.7440 | 14.72-15.13 | 710-745 | 0.7115-0.7801 | 13.98-15.38 |

TABLE 7-continued

Optimum wavelengths for Chl a,
Chl b and total Chl assessment in poplar leaves

| Chlorophylls | Visible range | | | NIR range | | |
|---|---|---|---|---|---|---|
| | Wavelength (nm) | $R^2$ | RMSE | Wavelength (nm) | $R^2$ | RMSE |
| Chl a + b | 575 | 0.9166 | 36.30 | 720 | 0.9352 | 33.48 |
| | 566-586 | 0.9010-0.9166 | 36.30-37.77 | 702-733 | 0.9002-0.9352 | 33.48-37.85 |

Comparison of Published Indices Used in Chl Assessment

Generally the published indices include one or two Chl related wavelengths and one Chl non-related wavelength. The Chl related wavelengths are usually the wavelength in red (675-710 nm), green (530-570 nm) or blue (420-445 nm). The Chl non-related wavelength is usually one wavelength in the NIR range of 750 to 940 nm; which is closely related to leaf structure but not related to leaf Chl content (Andrew et al. 2002).

Among 20 published indices tested, the indices $R_{750}/R_{700}$, $R_{850}/R_{710}$, $R_{698}/R_{760}$, $R_{710}/R_{760}$, $R_{695}/R_{760}$, $R_{695}/R_{420}$, $R_{675}/R_{700}$, $(R_{750}-R_{705})/(R_{750}+R_{705})$, $(R_{850}-R_{710})/(R_{850}-R_{680})$ and $(R_{800}-R_{700})/(R_{800}+R_{700})$ had larger $R^2$ and smaller RSME for Chl a assessment, the indices $R_{675}/R_{700}$, $R_{850}/R_{710}$, $R_{750}/R_{700}$, $R_{750}/R_{550}$, $(R_{850}-R_{710})/(R_{850}-R_{680})$ and $(R_{750}-R_{705})/(R_{750}+R_{705})$ have larger $R^2$ and smaller RSME for Chl b assessment, whereas indices $R_{850}/R_{710}$, $R_{675}/R_{700}$, $R_{750}/R_{700}$, $R_{710}/R_{760}$, $(R_{750}-R_{705})/(R_{750}+R_{705})$, $(R_{850}-R_{710})/(R_{850}-R_{680})$ and $(R_{800}-R_{700})/(R_{800}+R_{700})$ had larger $R^2$ and smaller RSME for total Chl assessment in poplar leaves (Table 7 to 9). With the same or similar wavelengths the indices of two wavelength simple ratio were better than NDVI and other indices. Moreover, all of these better indices included two wavelengths: one was Chl non-related NIR wavelength from 750 to 850 nm and the other was Chl related wavelength of 420, 675, 695, 698, 700, 705 or 710 nm. There was a tendency that the closer the Chl related wavelength to the optimum wavelength of 715, 730 or 720 nm the better the index for the assessment of Chl a, Chl b or Chl a+b, respectively. With Chl a, Chl b or Chl a+b related optimum wavelength 715, 730 or 720 nm, even the index was just a single wavelength alone, the $R^2$ and RSME were also very good. To verify the importance of the optimum wavelength for indices development, the Chl related wavelengths of 675, 695, 698, 700, 705 or 710 nm used in the published indices were replaced by the optimum wavelength of 715, 730 or 720 nm for Chl a, Chl b and Chl a+b, respectively, while keeping the Chl non-related NIR wavelength of 750 to 940 nm no change. The results indicated that all the modified indices had larger $R^2$ and smaller RSME than the corresponding published indices (Table 10). This result confirmed that using the optimum wavelength to develop the index was very importance for Chl assessment. Moreover, the Chl related optimum wavelength incorporated with Chl non-related wavelength further improved the accuracy of indices for Chl assessment (Table 10)

TABLE 8

Calibration equations for different indices of Chl a in poplar leaves

| Algorithms | indices | Calibration equation for converting algorithm result to Chl a (y) | $R^2$ | RSME ($\mu mol \cdot m^{-2}$) |
|---|---|---|---|---|
| $R_{750}/R_{700}$ | VI | $y = 1.7053x^2 + 40.872x - 33.936$ | 0.9664 | 23.77 |
| $R_{850}/R_{710}$ | VI | $y = -6.8891x^2 + 142.52x - 126.25$ | 0.9650 | 23.94 |
| $R_{698}/R_{760}$ | VI | $y = 1346.5x^2 - 1307.3x + 368.69$ | 0.9617 | 24.35 |
| $R_{710}/R_{760}$ | VI | $y = 502.89x^2 - 952.62x + 483.03$ | 0.9552 | 25.15 |
| $R_{695}/R_{760}$ | VI | $y = 2546.8x^2 - 1876.8x + 398.69$ | 0.9537 | 25.33 |
| $R_{695}/R_{420}$ | VI | $y = 13.55x^2 - 121.25x + 323.38$ | 0.9523 | 25.51 |
| $R_{675}/R_{700}$ | VI | $y = -751.33x^2 + 1012.5x - 159.87$ | 0.9478 | 26.06 |
| $R_{605}/R_{760}$ | VI | $y = 2745.3x^2 - 1927.6x + 390.64$ | 0.9132 | 30.22 |
| $R_{800}/R_{675}$ | PSSR a | $y = 6.3458x^2 - 51.623x + 157.69$ | 0.9076 | 30.89 |
| $R_{750}/R_{550}$ | VI | $y = 1.5579x^2 + 70.142x - 138.63$ | 0.8236 | 40.57 |
| $R_{940}/R_{675}$ | VI | $y = -15.16x^2 + 286.56x - 1230.1$ | 0.4208 | 77.53 |
| $R_{800}/R_{650}$ | PSSR b | $y = -12.87x^2 + 247.19x - 1058.6$ | 0.4176 | 77.77 |
| $(R_{750} - R_{705})/(R_{750} + R_{705})$ | Chl NDI | $y = 546.92x^2 + 9.3931x + 25.205$ | 0.9579 | 24.82 |
| $(R_{850} - R_{710})/(R_{850} - R_{680})$ | NDVI | $y = 353.06x^2 - 13.719x + 25.754$ | 0.9577 | 24.84 |
| $(R_{800} - R_{700})/(R_{800} + R_{700})$ | NDVI | $y = 692.07x^2 - 282.98x + 71.902$ | 0.9474 | 26.10 |
| $(R_{531} - R_{570})/(R_{531} + R_{570})$ | PRI | $y = 9131.5x^2 + 1618.1x + 125.07$ | 0.8371 | 39.00 |
| $(R_{800} - R_{445})/(R_{800} - R_{680})$ | NDVI | $y = 130858x^2 - 269038x + 138334$ | 0.8275 | 40.07 |
| $(R_{800} - R_{680})/(R_{800} + R_{680})$ | NDVI | $y = -8525.1x^2 + 14912x - 6346.1$ | 0.4145 | 77.99 |
| $(R_{750} - R_{675})/(R_{750} + R_{675})$ | NDVI | $y = -24484x^2 + 39491x - 15804$ | 0.3643 | 81.53 |
| $(R_{750} - R_{680})/(R_{750} + R_{690})$ | NDVI | $y = -24484x^2 + 39491x - 15804$ | 0.3643 | 81.53 |

TABLE 9

Calibration equations for different indices of Chl b in poplar leaves.

| Algorithms | Indices | Calibration equation for converting algorithm result to Chl b (y) | $R^2$ | RSME ($\mu mol \cdot m^{-2}$) |
|---|---|---|---|---|
| $R_{675}/R_{700}$ | VI | $y = 677.02x^2 - 348.64x + 57.178$ | 0.8292 | 12.93 |
| $R_{850}/R_{710}$ | VI | $y = 50.192x^2 - 140.89x + 111.23$ | 0.7757 | 14.07 |
| $R_{750}/R_{700}$ | VI | $y = 10.151x^2 - 44.357x + 60.758$ | 0.7549 | 14.50 |
| $R_{750}/R_{550}$ | VI | $y = 17.632x^2 - 88.406x + 122.36$ | 0.7457 | 14.69 |
| $R_{710}/R_{760}$ | VI | $y = 576.01x^2 - 791.77x + 283.67$ | 0.6990 | 15.63 |
| $R_{698}/R_{760}$ | VI | $y = 891.09x^2 - 702.81x + 149.26$ | 0.6098 | 17.33 |
| $R_{605}/R_{760}$ | VI | $y = 1804.1x^2 - 1042.2x + 161.11$ | 0.6007 | 17.50 |
| $R_{695}/R_{420}$ | VI | $y = 8.1571x^2 - 59.672x + 119.63$ | 0.5875 | 17.74 |
| $R_{695}/R_{760}$ | VI | $y = 1452.6x^2 - 911.21x + 153.15$ | 0.5683 | 18.08 |
| $R_{800}/R_{675}$ | PSSR a | $y = 3.8595x^2 - 40.967x + 119.82$ | 0.5396 | 18.59 |
| $R_{940}/R_{675}$ | VI | $y = -5.6063x^2 + 98.264x - 406.52$ | 0.1508 | 23.91 |
| $R_{800}/R_{650}$ | PSSR b | $y = -5.156x^2 + 89.886x - 367.72$ | 0.1450 | 23.96 |
| $(R_{850} - R_{710})/(R_{850} - R_{680})$ | NDVI | $y = 445.18x^2 - 317.88x + 68.406$ | 0.7085 | 15.44 |
| $(R_{750} - R_{705})/(R_{750} + R_{705})$ | Chl NDI | $y = 695.56x^2 - 368.18x + 60.419$ | 0.7076 | 15.46 |
| $(R_{800} - R_{700})/(R_{800} + R_{700})$ | NDVI | $y = 639.4x^2 - 491.88x + 105.89$ | 0.6691 | 16.21 |
| $(R_{531} - R_{570})/(R_{531} + R_{570})$ | PRI | $y = 4435.2x^2 + 586.71x + 29.785$ | 0.6260 | 17.03 |
| $(R_{800} - R_{445})/(R_{800} - R_{680})$ | NDVI | $y = 51774x^2 - 105981x + 54245$ | 0.5403 | 18.58 |
| $(R_{800} - R_{680})/(R_{800} + R_{680})$ | NDVI | $y = -5170.3x^2 + 8329.7x - 3329.9$ | 0.1403 | 23.99 |
| $(R_{750} - R_{675})/(R_{750} + R_{675})$ | NDVI | $y = -11067x^2 + 17391x - 6809.2$ | 0.1226 | 24.11 |
| $(R_{750} - R_{680})/(R_{750} + R_{690})$ | NDVI | $y = -11067x^2 + 17391x - 6809.2$ | 0.1226 | 24.11 |

TABLE 10

Calibration equations for different indices of total Chl in poplar leaves.

| Algorithms | Indices | Calibration equation for converting algorithm result to total Chl (y) | $R^2$ | RSME ($\mu mol \cdot m^{-2}$) |
|---|---|---|---|---|
| $R_{850}/R_{710}$ | VI | $y = 43.303x^2 + 1.6257x - 15.024$ | 0.9504 | 33.03 |
| $R_{675}/R_{700}$ | VI | $y = -74.309x^2 + 663.83x - 102.7$ | 0.9499 | 33.08 |
| $R_{750}/R_{700}$ | VI | $y = 11.856x^2 - 3.4853x + 26.822$ | 0.9459 | 33.47 |
| $R_{710}/R_{760}$ | VI | $y = 1078.9x^2 - 1744.4x + 766.7$ | 0.9188 | 36.09 |
| $R_{698}/R_{760}$ | VI | $y = 2237.5x^2 - 2010.1x + 517.94$ | 0.8648 | 41.10 |
| $R_{800}/R_{675}$ | PSSR a | $y = 10.205x^2 - 92.59x + 277.51$ | 0.8637 | 41.20 |
| $R_{605}/R_{760}$ | VI | $y = 4549.3x^2 - 2969.8x + 551.76$ | 0.8582 | 41.69 |
| $R_{695}/R_{420}$ | VI | $y = 21.707x^2 - 180.92x + 443.01$ | 0.8449 | 42.87 |
| $R_{750}/R_{550}$ | VI | $y = 19.19x^2 - 18.264x - 16.273$ | 0.8361 | 43.65 |
| $R_{695}/R_{760}$ | VI | $y = 3999.3x^2 - 2788x + 551.84$ | 0.8324 | 43.97 |
| $R_{940}/R_{675}$ | VI | $y = -20.766x^2 + 384.82x - 1636.6$ | 0.3512 | 76.45 |
| $R_{800}/R_{650}$ | PSSR b | $y = -18.025x^2 + 337.08x - 1426.3$ | 0.3465 | 76.67 |
| $(R_{750} - R_{705})/(R_{750} + R_{705})$ | Chl NDI | $y = 1242.5x^2 - 358.79x + 85.623$ | 0.9247 | 35.53 |
| $(R_{850} - R_{710})/(R_{850} - R_{680})$ | NDVI | $y = 798.25x^2 - 331.6x + 94.161$ | 0.9236 | 35.63 |
| $(R_{800} - R_{700})/(R_{800} + R_{700})$ | NDVI | $y = 1331.5x^2 - 774.85x + 177.79$ | 0.9041 | 37.48 |
| $(R_{800} - R_{445})/(R_{800} - R_{680})$ | NDVI | $y = 182632x^2 - 375018x + 192578$ | 0.7718 | 49.10 |
| $(R_{531} - R_{570})/(R_{531} + R_{570})$ | PRI | $y = 13567x^2 + 2204.9x + 154.86$ | 0.7652 | 49.64 |
| $(R_{800} - R_{680})/(R_{800} + R_{680})$ | NDVI | $y = -13695x^2 + 23241x - 9675.9$ | 0.3430 | 76.83 |
| $(R_{750} - R_{675})/(R_{750} + R_{675})$ | NDVI | $y = -35550x^2 + 56882x - 22613$ | 0.2989 | 78.73 |
| $(R_{750} - R_{680})/(R_{750} + R_{690})$ | NDVI | $y = -35550x^2 + 56882x - 22613$ | 0.2989 | 78.73 |

TABLE 11

Calibration equations, $R^2$ and RMSE for most commonly used Chl indices with the optimum wavelength of 715 nm, 730 nm and 720 nm in poplar leaves

| Chlorophylls | Optimum wavelength | Algorithms | Calibration equation for converting algorithm result to Chls (y) | $R^2$ | RSME ($\mu mol \cdot m^{-2}$) |
|---|---|---|---|---|---|
| Chl a | 715 nm | $R_{715}$ | $y = 851.93x^2 - 1296.8x + 462.95$ | 0.9604 | 24.51 |
| | | $R_{750}/R_{715}$ | $y = -11.525x^2 + 225.42x - 204.41$ | 0.9672 | 23.67 |
| | | $R_{800}/R_{715}$ | $y = -14.891x^2 + 225.55x - 200.13$ | 0.9674 | 23.65 |
| | | $R_{850}/R_{715}$ | $y = -13.423x^2 + 219.92x - 195.07$ | 0.9673 | 23.66 |
| | | $R_{940}/R_{715}$ | $y = -12.437x^2 + 216.13x - 189.45$ | 0.9685 | 23.51 |
| | | $R_{715}/R_{760}$ | $y = 483.84x2 - 1063.1x + 599.05$ | 0.9670 | 23.70 |
| | | $R_{715}/R_{420}$ | $y = 1.9583x^2 - 56.019x + 411.9$ | 0.9497 | 25.82 |
| | | $(R_{800} - R_{715})/(R_{800} + R_{715})$ | $y = 523.80x^2 + 358.10x + 12.244$ | 0.9673 | 23.66 |
| | | $(R_{750} - R_{715})/(R_{750} + R_{715})$ | $y = 588.06x^2 + 363.62x + 11.653$ | 0.9671 | 23.68 |
| | | $(R_{850} - R_{715})/(R_{850} + R_{715})$ | $y = 532.12x2 + 351.12x + 13.225$ | 0.9672 | 23.67 |

TABLE 11-continued

Calibration equations, $R^2$ and RMSE for most commonly used Chl
indices with the optimum wavelength of 715 nm, 730 nm and 720 nm in poplar leaves

| Chlorophylls | Optimum wavelength | Algorithms | Calibration equation for converting algorithm result to Chls (y) | $R^2$ | RSME ($\mu mol \cdot m^{-2}$) |
|---|---|---|---|---|---|
| Chl b | 730 nm | $R_{730}$ | $y = 2016.9x^2 - 1700.3x + 370.49$ | 0.8609 | 12.23 |
| | | $R_{750}/R_{730}$ | $y = 135.58x^2 - 341.74x + 227.7$ | 0.8666 | 12.10 |
| | | $R_{800}/R_{730}$ | $y = 120.13x^2 - 303.49x + 204.06$ | 0.8653 | 12.13 |
| | | $R_{850}/R_{730}$ | $y = 118.69x^2 - 299.59x + 201.43$ | 0.8645 | 12.15 |
| | | $R_{940}/R_{730}$ | $y = 117.24x^2 - 292.53x + 194.84$ | 0.8678 | 12.07 |
| | | $R_{730}/R_{760}$ | $y = 3512.4x2 - 6572.2x + 3086.7$ | 0.8657 | 12.12 |
| | | $R_{730}/R_{420}$ | $y = 5.9429x2 - 129.84x + 721.59$ | 0.8034 | 13.48 |
| | | $(R_{750} - R_{730})/(R_{750} + R_{730})$ | $y = 1438.5x^2 - 355.62x + 34.088$ | 0.8610 | 12.23 |
| | | $(R_{800} - R_{730})/(R_{800} + R_{730})$ | $y = 1326.6x^2 - 334.83x + 33.259$ | 0.8600 | 12.25 |
| | | $(R_{850} - R_{730})/(R_{850} + R_{730})$ | $y = 9607.6x2 - 605.83x + 21.928$ | 0.8572 | 12.31 |
| Chl a + b | 720 nm | $R_{720}$ | $y = 2868.8x^2 - 2997.1x + 833.44$ | 0.9484 | 33.22 |
| | | $R_{750}/R_{720}$ | $y = 124.06x^2 - 116.32x + 23.285$ | 0.9547 | 32.60 |
| | | $R_{800}/R_{720}$ | $y = 2026.5x^2 + 8.0036x + 45.741$ | 0.9540 | 32.67 |
| | | $R_{850}/R_{720}$ | $y = 105.27x^2 - 79.674x + 6.3681$ | 0.9542 | 32.65 |
| | | $R_{940}/R_{720}$ | $y = 105.24x^2 - 77.936x + 3.9312$ | 0.9544 | 32.63 |
| | | $R_{720}/R_{760}$ | $y = 1541.9x2 - 3009.4x + 1519.4$ | 0.9532 | 32.75 |
| | | $R_{720}/R_{420}$ | $y = 5.4584x2 - 131.1x + 839.39$ | 0.9280 | 35.21 |
| | | $(R_{750} - R_{720})/(R_{750} + R_{720})$ | $y = 104.80x^2 - 76.40x + 5.3944$ | 0.9559 | 32.48 |
| | | $(R_{800} - R_{720})/(R_{800} + R_{720})$ | $y = 1850.4x^2 + 23.272x + 45.503$ | 0.9537 | 32.70 |
| | | $(R_{850} - R_{720})/(R_{850} + R_{720})$ | $y = 2896.3x2 + 194.98x + 41.413$ | 0.9531 | 32.76 |

Optimum Indices Determination

Based on $R^2$ and wavelength sensitivity the optimum wavelength for Chl a, Chl b and Chl a+b were determined to be 580, 563 and 575 nm in visible green range and 715, 730 and 720 nm in NIR range, respectively (Table 6). The indices for Chl assessment were developed by incorporating the identified optimum wavelength for Chl a, Chl b and Chl a+b with each wavelength from 300 to 1100 nm as the form of simple ratio ($R_{300-1100}/R_{580}$, $R_{300-1100}/R_{563}$, $R_{300-1100}/R_{575}$, $R_{300-1100}/R_{715}$, $R_{300-1100}/R_{730}$ or $R_{300-1100}/R_{720}$) or as the form of NDVI ($(R_{300-1100}-R_{580})/(R_{300-1100}+R_{580})$, $(R_{300-1100}-R_{563})/(R_{300-1100}+R_{563})$, $(R_{300-1100}-R_{575})/(R_{300-1100}+R_{575})$, or as the form of NDVI $(R_{300-1100}-R_{715})/(R_{300-1100}+R_{715})$, $(R_{300-1100}-R_{730})/(R_{300-1100}+R_{730})$ or $(R_{300-1100}-R_{720})/(R_{300-1100}+R_{720})$. The $R^2$ result of these indices indicated that there were three peaks in the $R^2$ curves of Chl a, Chl b or Chl a+b for both simple ratio and NDVI: one was in the NIR range (750-1100 nm), one was in blue (350-550 nm) and the other was in green to red range (550-650 nm) (FIGS. 14 and 15). However, the $R^2$ peaks in the ranges of NIR and blue were much larger than that in the range of green to red.

The curve trend of RMSE was reversely correlated to the curve trend of $R^2$, and showed the lager the $R^2$ the smaller the RMSE (FIGS. 14 and 15). Statistically, the indices having larger $R^2$ and smaller RMSE can be used as optimum indices for Chl assessment. Therefore, the indices of simple ratio or NDVI incorporated one Chl non-related NIR wavelength among 750 to 1000 nm or incorporated one blue range wavelength among 400 to 490 nm with the optimum Chl related wavelengths in NIR (715, 730 or 720 nm) or in green (580, 563 or 574 nm) that had larger R2 and smaller RMSE could be used as the optimum indices for Chl a Chl b or Chl a+b assessment. In contrast to the indices that incorporated one blue range wavelength with one Chl related optimum wavelength, the $R^2$ peak of the indices incorporated one Chl non-related NIR wavelength with one Chl related optimum wavelength was wider and more stable (FIGS. 14 and 15).

The optimum indices for different Chls were different. For Chl a or Chl a+b the indices of one NIR wavelength among 750 to 1000 nm incorporated with the Chl a or Chl a+b related optimum wavelength of 715 or 720 nm were better than the other wavelength involved in the indices; whereas for Chl b the indices of one blue wavelength among 400 to 490 nm incorporated with the Chl b related optimum wavelength 563 nm were better than the other wavelength involved in indices (FIGS. 14 and 15). Chl related optimum wavelength was very important for indices development. The indices even just with the single optimum wavelength alone either in the green or in the NIR range also had a large $R^2$ and small RMSE, although the $R^2$ and RMSE of the indices could be further improved by incorporating the Chl related optimum wavelength with one wavelength either from 400-490 nm or 750 to 1000 nm as the form of simple ratio or NDVI (FIG. 14 and Table 11).

TABLE 12

The optimum wavelength and indices selected for the assessment of Chl a,
Chl b snd Chl a + b based on the $R^2$ that was larger than 0.9400,
0.7400 and 0.9300 for Chl a, Chl b and Chl a + b in poplar leaves, respectively

| | | Optimum wavelength in visible | | Optimum wavelength in NIR | |
|---|---|---|---|---|---|
| Chlorophylls | Algorithm | | R2 | Algorithm | R2 |
| Chl a | $R_{580}$ | | 0.9497 | $R_{715}$ | 0.9604 |
| Chl b | $R_{563}$ | | 0.7440 | $R_{730}$ | 0.7801 |
| Chl a + b | $R_{574}$ | | 0.9166 | $R_{720}$ | 0.9484 |

TABLE 12-continued

The optimum wavelength and indices selected for the assessment of Chl a,
Chl b snd Chl a + b based on the $R^2$ that was larger than 0.9400,
0.7400 and 0.9300 for Chl a, Chl b and Chl a + b in poplar leaves, respectively

| Chlorophylls | Optimum wavelength in visible | | Optimum wavelength in NIR | |
|---|---|---|---|---|
| | Algorithm | R2 | Algorithm | R2 |
| Chl a | $R_{368-466}/R_{580}$ | 0.9498-0.9610 | $R_{750-1100}/R_{715}$ | 0.9644-0.9697 |
| | $R_{750-1100}/R_{580}$ | 0.9621-0.9655 | | |
| Chl b | $R_{380-681}/R_{563}$ | 0.7458-0.8335 | $R_{750-1100}/R_{730}$ | 0.7400-0.7819 |
| | $R_{750-1100}/R_{563}$ | 0.7788-0.7907 | $R_{409-448}/R_{730}$ | 0.7412-0.7854 |
| Chl a + b | $R_{386-489}/R_{574}$ | 0.9306-0.9460 | $R_{423-425}/R_{720}$ | 0.9308-0.9316 |
| | $R_{750-1100}/R_{574}$ | 0.9370-0.9421 | $R_{750-1100}/R_{720}$ | 0.9425-0.9535 |
| Chl a | $(R_{386-489} - R_{580})/(R_{386-489} - R_{580})$ | 0.9499-0.9619 | $(R_{750-1100} - R_{715})/(R_{750-1100} - R_{715})$ | 0.9644-0.9680 |
| | $(R_{750-1100} - R_{580})/(R_{750-1100} - R_{580})$ | 0.9499-0.9526 | | |
| Chl b | $(R_{380-679} - R_{563})/(R_{380-679} + R_{563})$ | 0.7462-0.8176 | $(R_{409-448} - R_{730})/(R_{409-448} + R_{730})$ | 0.7401-0.7707 |
| | | | $(R_{750-1100} - R_{730})/(R_{750-1100} + R_{730})$ | 0.7436-0.7824 |
| Chl a+b | $(R_{386-489} - R_{574})/(R_{386-489} + R_{574})$ | 0.9300-0.9426 | $(R_{423-425} - R_{720})/(R_{423-425} + R_{720})$ | 0.9301-0.9308 |
| | | | $(R_{750-1100} - R_{720})/(R_{750-1100} + R_{720})$ | 0.9347-0.9463 |

Discussion

Chls are the sensitive indicator of plant potential photosynthetic capability (Curran et al. 1990, Filela et al 1995, Gitelson et al 2003, Jonathan et al. 2000, Richardson et al 2002), nitrogen status (Filella et al 1995, Moran et al 2000), and various stresses (Carter and Knapp 2001, Hendry 1987, Peñuelas and Filella 1998). Leaf Chl can be assessed non-destructively either by using the indices of Chl related single wavelength (i.e., 550 698, 692 or 695 nm) alone (Thomas and Gausman 1977, Jacquemoud and Baret 1990, Cater 1994, 1998, Moran and Moran 1998) or by using the indices of Chl related wavelength in combination with Chl insensitive wavelength as the form of wavelength ratio (i.e., R698/R760) or some specific indices like NDVI (Moran et al. 2000, Peñuelas et al 1995b). There are many indices that have been developed for Chl non-destructive assessment in a variety of plants (Curran et al., 1990; Gitelson & Merzlyak, 1994, 1996; Gitelson et al., 1996a, 1996b, Blackburn 1998, Datt 1998, 1999a, 1999b; Adams et al., 1999; Gamon & Surfus, 1999). However, these indices have rarely been tested using data from species other than those used in the formulation of the index (Richardson et al 2002), and there is no any index that can be used universally among various species. Gamon & Surfus (1999) demonstrated that the relationship between NDVI and total Chl is markedly different for the coniferous *Pseudotsuga menziesii* and the herbaceous *Helianthus annuus*; they suggest this may be due to differences in leaf morphology and structure. Differences in leaf structure and the associated effects of this on leaf reflectance appear to severely impair ability by using some indices across a wide range of vegetation types (Andrew et al 2002). In addition, such differences make it unlikely that calibration equations from one study can be directly applied to leaves with different structural attributes (Andrew et al 2002). There are many reasons that these proposed indices are not applicable in different species or different studies. However, the main reason, according to our study, is that the Chl related optimum wavelengths (OW) for measuring Chl used in one study differ from the optimum wavelengths used in the other studies because the optimum wavelengths vary among species or cultivar. The difference of leaf morphology, structure and other parameters for different species or cultivar shift the Chl related optimum wavelength either to a higher or a lower waveband and resulted in that same index could be used among species or cultivars.

Chl related optimum wavelength identification is very important for indices development. Optimum indices used for Chl assessment is the combination of Chl related optimum wavelength and the proper indices. The $R^2$ and the corresponding RMSE differed great among proposed indices in our study. For example, the proposed indices of $R_{750}/R_{700}$ (Gitelson et al. 1996a) and $(R_{750}-R_{705})/(R_{750}+R_{705})$ (Gitelson and Merzlyak 1994b, Gitelson 1994a, Gamon and Surfus 1999) had much larger $R^2$ and smaller RMSE for Chl a, Chl b and Chl a+b assessment; in contrast, the proposed indices of $R_{800}/R_{650}$ (Blackburn, 1998) and $(R_{750}-R_{675})/(R_{750}+R_{675})$ (Gamon and Qiu 1999, Richardson and Berlyn 2002) had smaller $R^2$ and larger RMSE (Table 9 to 11). When the Chl related wavelengths (675, 695, 698, 700, 705 or 710 nm) in different proposed indices were replaced by the optimum wavelength 580, 563 and 574 nm in green or 715, 730 and 720 nm in NIR for Chl a, Chl b or Chl a+b, respectively, all the modified indices had larger $R^2$ and smaller RSME (Table 12). Even with Chl a, Chl b or Chl a+b related single optimum wavelength 715, 730 or 720 nm alone the $R^2$ and RSME were also very good and similar to the indices of the optimum wavelength with one NIR wavelength in simple ratio or NDVI (Table 11). The results of Table 11 can be simplified into $R_{750-1000}/R_{ow}$, $(R_{750-1000}-R_{ow})/(R_{750-1000}+R_{ow})$, $R_{430-490}/R_{ow}$ and $(R_{430-490}-R_{ow})/(R_{430-490}+R_{ow})$, in which the optimum wavelengths are wavelength 580, 563 and 574 nm in green or 715, 730 and 720 nm in NIR for Chl a, Chl b or Chl a+b, respectively.

An important objective for Chl assessment is to find some indices that can be used across a wide range of species and functional groups (Andrew et al 2002). Although the Chl related optimum wavelengths differ among species, cultivar and Chls (Chl a, Chl b and Chl a+b), our test results of 'Fuji' apple, almond and other tree species indicated that there were two ranges of Chl related optimum wavelengths that hold for all species and different Chls (Chl a, Chl b and Chl a+b): one is in the NIR range of 700-740 nm, the other is green range of 540-580 nm (data not listed). In contrast to Chl related wavelengths, there were two ranges of Chl non-related reference wavelengths (RW) that hold for all species and different Chls (Chl a, Chl b and Chl a+b): one was in 430-490 nm and the other is in 750-1100 nm. To simplify, the indices that can be used across different species can be summarized into $R_{rw}/R_{ow}$, $(R_{rw}-R_{ow})/(R_{rw}+R_{ow})$, in which the Chl related optimum wavelengths are 540-580 nm in green and 700-740 nm in NIR, whereas the Chl non-related reference wavelengths are 430-490 nm in blue and 750-1100 nm in NIR.

Part VI

Effect of Leaf Properties on Leaf Chlorophyll Non-Destructive Assessment by Spectral Reflectance There were two ranges of optimum wavelengths, one in the visible of 550-636 nm, the other at red edge of 710-720 nm, that had larger $R^2$, smaller root mean square error (RMSE) and sensitive to a wide-range of chlorophyll (Chl) content from 160 to 1188 μg·m² among the genotypes tested. Using the Chl related optimum wavelength in the algorithm was very important for Chl assessment; however, the optimum wavelength differed among plant genotypes, which impaired the ability of an index or calibration equation from one genotype to be used across a wide range of genotypes. Although the optimum wavelengths in both visible (540-560 nm) and red edge (702-720 nm) among cultivars within the apple species were narrower than that among different species, the effect of leaf morphology and structure on the optimum wavelength for Chl assessment also existed and the $R^2$ could be further improved by using the optimum wavelength in the algorithm for each specific cultivar instead of using one common wavelength in the algorithm to across different cultivars. In the leaves of anthocyanin-containing species of purple leaf plum and purple leaf flowering plum, there were two major anthocyanin $R^2$ peaks that overlapped with two Chl $R^2$ peaks in the green range of 500-600 nm and red edge of 700-750 nm, respectively. However, in the leaves of purple leaf flowering plum the Chl related $R^2$ was not affected by the existence of anthocyanin, whereas in the leaves of purple leaf plum the $R^2$ was severely affected. Carotenoid content was closely and proportionally related to Chl content in all the species tested. Although two $R^2$ peaks of Chl related reflectance were overlapped by two $R^2$ peaks of carotenoid, the Chl reflectance $R^2$ was not affected by carotenoid. The variation of reflectance in the green range of 540-600 nm and red edge of 700-740 nm was related to both leaf Chl content and leaf optical properties, i.e., texture and thickness, whereas the variation of reflectance in the NIR range of 750-1100 nm was related to leaf optical properties rather than Chl content. The variation of reflectance in green and red edge caused by the variation of leaf texture or other optical properties also resulted in a reflectance variation in the same direction in the range of NIR; therefore, by referencing green or red edge wavelength that were sensitive to Chl to the NIR wavelength that was sensitive to leaf texture but insensitive to Chl, the effect of leaf texture or optical properties on Chl assessment could be eliminated by the algorithms of simple ratio $R_{540-560}/R_{750-1100}$, $R_{700-740}/R_{750-1100}$ or other algorithms. Leaf dehydration increased leaf reflectance in the ranges green (540-600 nm), red edge (710-740 nm) and NIR (1350-2500 nm). However, leaf reflectance in the wavelength of 750-1000 nm that sensitive to leaf texture was not significantly affected by dehydration. Therefore, the effect of leaf water status on reflectance may be eliminated by referencing the reflectance of Chl sensitive wavelength either in green or red edge to the water most sensitive wavelength of 1420-1510 nm. Taking into account the above circumstances, the optimum wavelengths at red edge had a narrower range, larger $R^2$, smaller RMSE, and the algorithm with the optimum wavelength as the form of $R_{700-740}/R_{750-1100}$ was more tolerant to the existence of anthocyanin, the variation of leaf water status and other interferences.

Introduction

The chlorophyll (Chl), the dominant and the essential pigments of green leaves, determines to a great extent the amount of PAR absorbed by the leaf, the photosynthetic rate, and plant productivity (Gamon and Qiu 1999, Kochubei 1990, Nichlporovich 1974, and Richardson et al 2002). As the indicator of plant N status (Filella et al 1995, Moran et al 2000) and various stress (Carter and Knapp 2001, Hendry 1987, Peñuelas and Filella 1998), Chl content undergoes directional and specific changes in the course of plant growth and development, during adaptation to unfavorable environmental conditions, and under various stresses and damages (Demmig-Adams et al. 1996, Gamon and Qiu 1999, Lichtenthaler 1996, Markstädter et al 2001, Merzlyak et al. 1999, Peñuelas and Filella 1998). Traditionally, plant Chl analysis is performed with spectrophotometry of tissue extracts with organic solvents (Arnon 1949, Merzlyak et al. 2003). The application of this methodology involves tissue destruction; it is time-consuming and is coupled with artifacts due to pigment instability, incomplete extraction, the presence of light absorbing impurities, etc. (Lichtenthaler 1987, Solovchenko et al. 2001). Recently, the alternative nondestructive optical methods for Chl assessment, based on the absorbance and/or reflectance of light by the intact leaf, have been developed (Curran et al. 1990, Adams et al. 1999, Datt 1999, Gamon and Surfus 1999, Markwell et al. 1995). These optical methods require no chemical analysis, are nondestructive, simple to use, fast, inexpensive and can be used in the field (Buschmann and Nagel 1993, Gitelson and Merzlyak 1994, Gitelson et al 1996a, 1996b, Markwell et al 1995). Most of the previous papers were focused on Chl related indices development and/or evaluation (Curran et al., 1990; Gitelson & Merzlyak, 1994, 1996; Gitelson et al., 1996a, 1996b, Blackburn 1998, Datt 1998, 1999; Adams et al., 1999; Gamon & Surfus, 1999). However, many of these indices have rarely been tested using data from species other than those used in the formulation of the index (Richardson et al 2002). There are many reasons why the proposed algorithms are not applicable for Chl assessment in different studies and among different species. However, the main reason is that the optimum wavelengths for measuring Chl used in one study differed from that used in other studies, because the optimum wavelengths vary with the plant genotype and phenotype. Essentially, it is the variation of leaf optical properties (leaf thickness, texture, density, Chl content, water status, etc.) that affected the popularity of algorithm used for Chl assessment among species, cultivars or different studies. Therefore, the purpose of this study was to analyze the effect plant species and cultivars on Chl related optimum wavelength and Chl assessment; to analyze the variation of leaf texture and leaf water status on Chl assessment, and to analyze the contents of leaf Chl and carotenoid, and the existence of anthocyanin on Chl related optimum wavelength and Chl assessment.

Materials and Methods

Plant Materials

'Nonpareil' almond (*Prunus dulcis* (Mill.) D. A. Webb), poplar (UCC-1, a hybrid of *Populus trichocarpa*×*P. deltoides*, Union Camp, Princeton, N.J.) and bench-grafted Fuji apple (*Malus domestica* Borkh) trees on M.26 rootstocks were grown in 7.2 L pots with a medium of 1 peat moss:2 pumice:1 sandy loam soil (v:v) in a lathhouse from 26 March to 5 June. Beginning from budbreak in early May, they were fertilized every 2 weeks with 10.7 mM N, using Plantexâ 20N-10P$_2$O$_5$-20K$_2$O water-soluble fertilizer with micronutrients (Plantex Corp., Ontario, Canada). When the new shoots were approximately 15 cm long, plants were moved to full sunlight. Thereafter, they were fertilized weekly with Plantexâ for 3 weeks. Beginning on 30 June, plants were fertilized twice weekly with one of the six N concentrations (0, 2.5, 5, 7.5, 10, or 20 mM N from NH$_4$NO$_3$) by applying 300 ml of a modified Hoagland's solution to each pot until the end of September, three successive years. Starting from July 10 fresh leaves with different Chl and N contents from each N fertigation treatment plants were harvested. Meanwhile, 30 to 50 leaves with different Chl and N were collected from 15 years old purple leaf plum (*Prunus cerasifera* 'Newport') and 10 years old purple leaf flowering plum (*Prunus serrolata*) growing on the campus of Oregon State University under natural conditions. All these harvested leaves were immediately placed into plastic bags and transported to the laboratory for spectral reflectance, leaf Chl and other pigments analysis.

Leaf Reflectance Spectrum

Leaf discs taken with a 2.85 cm$^2$ cork borers were immediately scanned by using Li-1800 spectroradiometer (Li-Cor Inc., Lincoln, Nebr.) from 300 nm to 1100 nm with 1 nm interval to measure the spectral reflectance. Two scans were made per sample and then average. The reflectance spectrum for each scan was calculated as $R_\lambda$=leaf radiance at wavelength $\lambda$/reflectance standard radiance at wavelength $\lambda$, and was averaged across the two separate scans made on each leaf disc. Meanwhile, the same leaf disc was analyzed by using FOSS-SYS-6500 from 400 nm to 2500 nm with 2 nm interval to measure the spectral reflectance.

Chl and Other Leaf Pigment Analysis

After scanning the leaf discs were then extracted in 80% (v/v) acetone at 4° C. in the dark for Chl and carotenoid content. Absorptance of the extract was measured with a Shimadzu UV-visible spectrophotometer UV-1601. Total Chl and was calculated according to Lichtenthaler and Wellburn (1983). Anthocyanins content was determined according to Abdel-Aal and Hucl (1999)

Effect of Leaf Texture on Reflectance

In an attempt to understand how texture affecting leaf Chl assessment, the reflectance of leaves with almost the same Chl content but different reflectance were by using FOSS-SYS-6500 from 400 nm to 2500 nm with 2 nm interval to measure the spectral reflectance.

Effect of Leaf Water Status on Leaf Reflectance

The leaves of 'Fuji' apple and purple leaf flowering plum were used in this experiment. Four leaf disks were taken from two opposite sides of the main central vein with a 2.85 cm$^2$ cork borers to measure the fresh weight and then immediately scanned by using FOSS-SYS-6500 from 400 nm to 2500 nm with 2 nm interval to measure the spectral reflectance, respectively. The scanned leaf disks were allowed to dry for one hour at room temperature. After drying the leaf disc was reweighed and rescanned to determine the weight and the spectral reflectance after dehydration. The leaves were then put into 85° C. oven for 48 hours to obtain the leaf dry weight to calculate the effect of leaf water status (e.g., leaf water content) on reflectance. Leaf disc water content was expressed as percentage of water on a fresh weight basis.

Simple Linear Regression Coefficient Determination (R2) and Root Mean Square Error (RSME)

Simple linear regression between the reading of each wavelength and Chls (Chl a, Chl b or Ch a+b) was developed for each wavelength from 300 nm to 1100 nm with 1 nm interval. The related $R^2$ and RSME curves of Chl a, Chl b and Ch a+b were developed at each wavelength for optimum wavelength selection, respectively.

Results

Effect of Plant Species on Chl Related Optimum Wavelength and $R^2$

The result of simple linear regression $R^2$ between the reading of reflectance and Chls (Chl a, Chl b or Ch a+b) for each wavelength from 300 to 1100 nm indicated that there were two Chl-related $R^2$ peaks, one in the visible green and the other in the red edge, that could be used for measuring Chl in all the species tested. The optimum wavelengths and Chl related reference $R^2$ for measuring Chl in different species were different in both the visible range and the red edge. The optimum wavelengths in the visible range were 552-630 nm for Chl a, 550-636 nm for Chl b, and 552-630 nm for total Chl; in contrast the optimum wavelength in the red edge were 710-720 nm for Chl a, 710-717 nm for Chl b, and 710-720 nm for total Chl, respectively (Table 14). The Chl related reference $R^2$ at the red edge was larger than that in the visible range in the leaf of all species except in the leaf of almond and purple leaf flowering plum, in which the $R^2$ was a little larger in the visible range. According to our result (not listed here) the Chl-related wavelength used in the algorithm was critical, even if it was just a few nanometers away from the optimum wavelength it could significantly affect the regression $R^2$ and RMSE.

Effect of Cultivar on Chl Related Optimum Wavelength and $R^2$

In an attempt to determine whether the optimum wavelength or algorithm can be used among different genotypes within the same species, the $R^2$ and RMSE in the visible green and red edge of the spectra was used on four apple cultivars. The results indicated that different apple genotypes had different optimum wavelengths for Chl assessment. For example, the optimum wavelength at red edge of Chl a, Chl b and total Chl among cultivars varied from 708 to 720 nm, 702 to 717 nm and 708 to 720 nm, respectively (Table 15). Although the difference of optimum wavelength among cultivars were only about 12-15 nm in the red edge and 20 nm in the green range, the linear regression $R^2$ and RMSE for the different genotypes were different due to the differences of their physical makeup. The results indicated that the optimum wavelength and related algorithm developed for one genotype may vary for the other genotypes.

TABLE 14

$R^2$ peaks, RMSE and the corresponding wavelength of Chl a, Chl b and Chl a + b in the leaf of Fuji apple, poplar and almond leaves

| | | Visible range | | | NIR range | | |
|---|---|---|---|---|---|---|---|
| Species | Chls | WL (nm) | $R^2$ | RMSE ($\mu g \cdot m^{-2}$) | WL (nm) | $R^2$ | RMSE ($\mu g \cdot m^{-2}$) |
| 'Fuji' apple | Ch a | 552 ± 25$^z$ | 0.7785 | 96.61 | 720 ± 20$^z$ | 0.9198 | 57.69 |
| | Ch b | 550 ± 25 | 0.7225 | 26.94 | 717 ± 20 | 0.8465 | 19.59 |
| | Ch a + b | 552 ± 25 | 0.7695 | 122.07 | 720 ± 20 | 0.9072 | 75.76 |
| Poplar | Ch a | 581 | 0.9497 | 7.59 | 715 | 0.9579 | 6.93 |
| | Ch b | 563 | 0.7440 | 5.72 | 730 | 0.7801 | 5.30 |
| | Ch a + b | 575 | 0.9166 | 25.54 | 720 | 0.9355 | 38.67 |

TABLE 14-continued

R² peaks, RMSE and the corresponding wavelength of Chl
a, Chl b and Chl a + b in the leaf of Fuji apple, poplar and almond leaves

| | | Visible range | | | NIR range | | |
|---|---|---|---|---|---|---|---|
| Species | Chls | WL (nm) | $R^2$ | RMSE ($\mu g \cdot m^{-2}$) | WL (nm) | $R^2$ | RMSE ($\mu g \cdot m^{-2}$) |
| Almond | Ch a | 550 | 0.8740 | 12.78 | 710 | 0.8678 | 13.09 |
| | Ch b | 558 | 0.8256 | 3.75 | 710 | 0.8144 | 3.87 |
| | Ch a + b | 550 | 0.8737 | 47.55 | 710 | 0.8667 | 48.83 |
| Purple leaf flowering plum | Ch a | 592 | 0.9388 | 26.64 | 716 | 0.9291 | 28.68 |
| | Ch b | 580 | 0.9207 | 11.14 | 714 | 0.8750 | 13.99 |
| | Ch a + b | 590 | 0.9339 | 37.79 | 714 | 0.9170 | 42.37 |
| Purple leaf plum | Ch a | 630 | 0.5392 | 39.82 | 712 | 0.6020 | 37.01 |
| | Ch b | 636 | 0.5105 | 16.29 | 714 | 0.5870 | 14.96 |
| | Ch a + b | 636 | 0.5354 | 55.62 | 714 | 0.6027 | 51.43 |

TABLE 15

The optimum wavelength (OW), linear regression R2 and RMSE in
the red edge for assessing chlorophylls (Chls) in different apple cultivars

| | | Visible range | | | Red edge | | |
|---|---|---|---|---|---|---|---|
| Apple Cultivars | Chls | OW (nm) | R2 | RMSE ($\mu g \cdot m^{-2}$) | OW (nm) | R2 | RMSE ($\mu g \cdot m^{-2}$) |
| Fuji | Chl a | 552 | 0.7785 | 96.61 | 720 | 0.9198 | 57.69 |
| | Chl b | 550 | 0.7225 | 26.94 | 717 | 0.8465 | 19.59 |
| | Chl a + b | 552 | 0.7695 | 122.07 | 720 | 0.9072 | 75.76 |
| Jonagold | Chl a | 558 | 0.9527 | 55.59 | 710 | 0.9659 | 47.22 |
| | Chl b | 560 | 0.9168 | 28.54 | 702 | 0.9139 | 29.04 |
| | Chl a + b | 558 | 0.9505 | 84.13 | 708 | 0.9581 | 76.26 |
| Gala | Chl a | 540 | 0.8492 | 80.12 | 708 | 0.8773 | 72.26 |
| | Chl b | 552 | 0.8294 | 34.95 | 710 | 0.8637 | 31.24 |
| | Chl a + b | 540 | 0.8453 | 115.05 | 708 | 0.8755 | 103.5 |
| Cameo | Chl a | 560 | 0.8804 | 92.32 | 716 | 0.9175 | 62.57 |
| | Chl b | 550 | 0.8095 | 26.78 | 708 | 0.8612 | 23.45 |
| | Chl a + b | 560 | 0.8643 | 119.11 | 714 | 0.9023 | 85.23 |

Influence of Leaf Texture

Figure 16A:
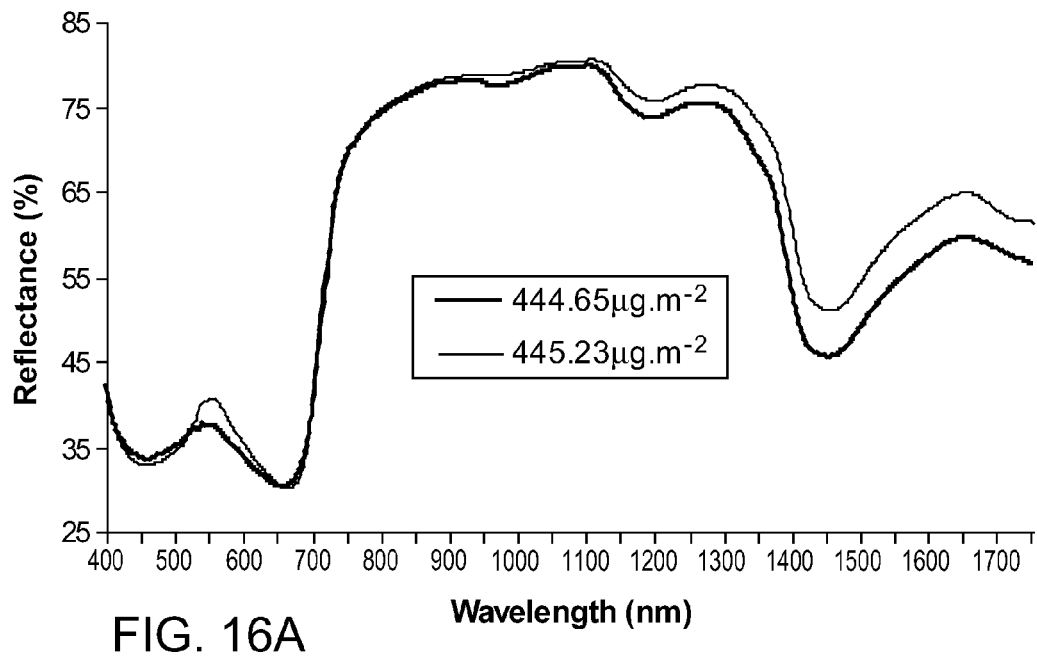
FIGS. 16A and 16B show graphs of reflectance spectra of leaves with almost the same total Chl content and different NIR reflectance (the higher NIR reflectance values correspond to higher reflectance in green).
Figure 16B:
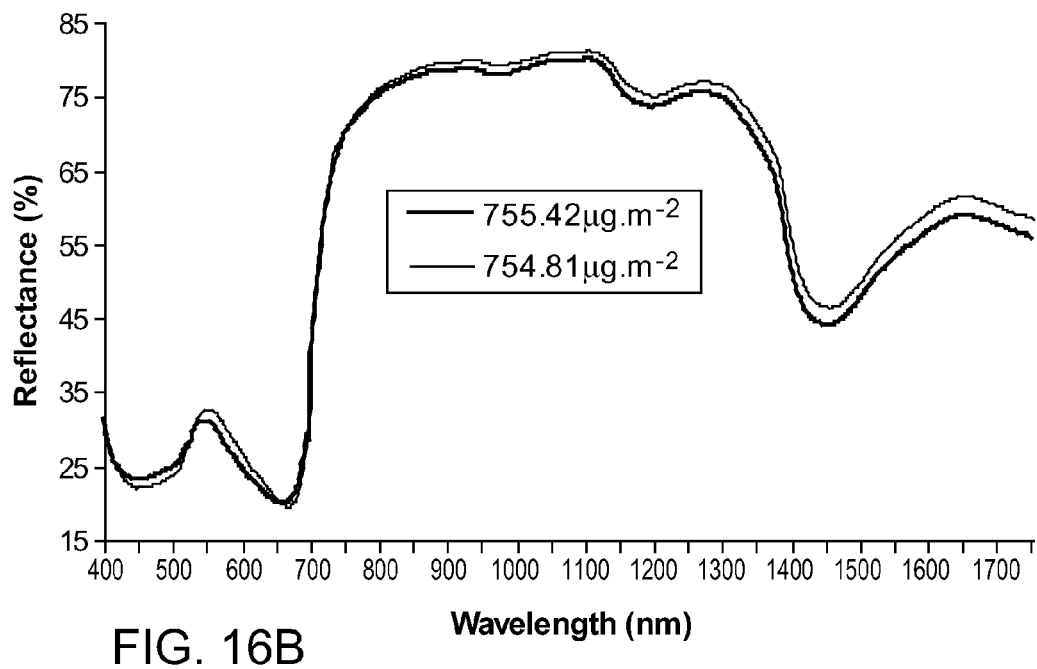

In an attempt to understand how texture (thickness and/or density) affecting leaf Chl assessment, the reflectance spectra of leaves with almost the same Chl content but different reflectance were compared (FIG. 16). The results indicated that the higher the reflectance in the range of green (540-600 nm) and red edge (710-740 nm), the higher the reflectance in the NIR range (750-1750 nm). The factors that govern the behavior of reflectance in the range of green (540-600 nm) and red edge (710-740 nm) were very different from the factors that govern the behavior of reflectance in the range of NIR (750-1750 nm). In the NIR range, an increase in reflectance might be caused by an increase in leaf thickness or density; in the range of green and red edge, an increase in reflectance indicates a decrease in Chl or other pigment content.

In leaves with the same Chl content, an increase in leaf thickness might cause an increase in reflectance in the Chl insensitive NIR range and a relative decrease in Chl concentration on unit volume basis; which caused an increase in reflectance in green and red edge (FIG. 1). Contrarily, a decrease in leaf thickness might lead to a decrease in reflectance in NIR range and to a relative increase in Chl concentration; the latter caused a decrease in reflectance in the green and red edge.

With the variation in leaf texture, reflectance in the range of green (540-600 nm), red edge (710-740 nm), and NIR (750-1000) varied in the same direction, therefore, by referencing green or red edge wavelengths that are sensitive to Chl to the NIR wavelength that are sensitive to leaf texture but insensitive to Chl, the effect of leaf texture on Chl assessment can be eliminated by the algorithms of simple ratio $R_{540-560}/R_{750-1000}$, $R_{710-740}/R_{750-1000}$ and normalized reflectance difference $(R_{540-560}-R_{750-1000})/(R_{540-560}+R_{750-1000})$, and $(R_{710-740}-R_{750-1000})/(R_{710-740}+R_{750-1000})$. With these algorithms all regression $R^2$ and RMSE for different species were improved except that of purple leaf plum in both green and red edge (Table 3).

TABLE 16

The $R^2$ and RMSE for the algorithms of Chl related single optimum wavelength (OW) alone, simple ratio normalized reflectance difference

| | | Visible range | | | Red edge | | | |
|---|---|---|---|---|---|---|---|---|
| Species | OW (nm) | Algorithms | $R^2$ | RMSE | OW (nm) | Algorithms | $R^2$ | RMSE |
| 'Fuji' apple | 552 | $R_{720}$ | 0.7695 | 122.07 | 720 | $R_{720}$ | 0.9072 | 75.76 |
| | | $R_{850}/R_{720}$ | 0.8611 | 94.73 | | $R_{850}/R_{720}$ | 0.9371 | 63.74 |
| | | $(R_{850} - R_{720})/(R_{850} + R_{720})$ | 0.8067 | 111.80 | | $(R_{850} - R_{720})/(R_{850} + R_{720})$ | 0.9370 | 63.81 |
| Poplar | 575 | $R_{575}$ | 0.9166 | 38.23 | 720 | $R_{720}$ | 0.9352 | 33.48 |
| | | $R_{850}/R_{575}$ | 0.9390 | 32.60 | | $R_{850}/R_{720}$ | 0.9480 | 30.09 |
| | | $(R_{850} - R_{575})/(R_{850} + R_{575})$ | 0.9157 | 38.33 | | $(R_{850} - R_{720})/(R_{850} + R_{720})$ | 0.9405 | 32.21 |
| Almond | 550 | $R_{550}$ | 0.8737 | 47.55 | 710 | $R_{710}$ | 0.8667 | 48.83 |
| | | $R_{850}/R_{550}$ | 0.9346 | 34.19 | | $R_{850}/R_{710}$ | 0.9393 | 32.98 |
| | | $(R_{850} - R_{550})/(R_{850} + R_{550})$ | 0.9215 | 37.48 | | $(R_{850} - R_{710})/(R_{850} + R_{710})$ | 0.9278 | 35.95 |
| Purple leaf flowering plum | 590 | $R_{590}$ | 0.9339 | 37.79 | 714 | $R_{714}$ | 0.9170 | 42.37 |
| | | $R_{850}/R_{590}$ | 0.9431 | 35.08 | | $R_{850}/R_{714}$ | 0.9436 | 34.93 |
| | | $(R_{850} - R_{590})/(R_{850} + R_{590})$ | 0.9423 | 35.32 | | $(R_{850} - R_{714})/(R_{850} + R_{714})$ | 0.9393 | 36.23 |
| Purple leaf plum | 636 | $R_{636}$ | 0.5354 | 55.62 | 714 | $R_{714}$ | 0.6027 | 51.43 |
| | | $R_{850}/R_{636}$ | 0.3612 | 65.22 | | $R_{850}/R_{714}$ | 0.5168 | 56.72 |
| | | $(R_{850} - R_{636})/(R_{850} + R_{636})$ | 0.3610 | 65.23 | | $(R_{850} - R_{714})/(R_{850} + R_{714})$ | 0.5143 | 56.87 |

Influence of Leaf Water Status

Figure 17A:
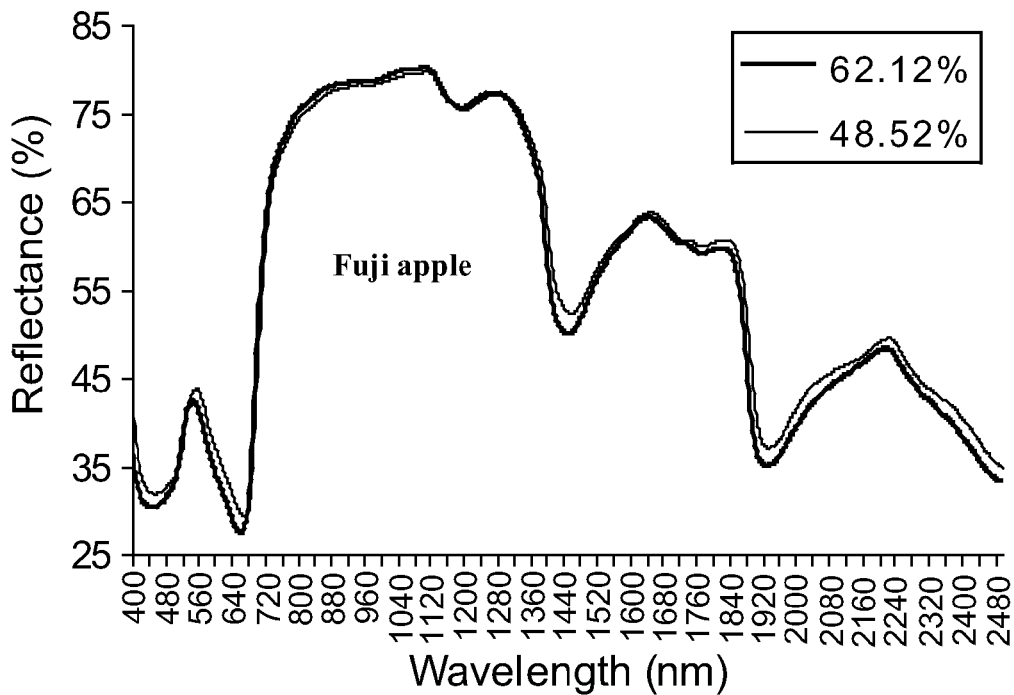
FIGS. 17A and 17B show graphs of the effect of the same species leaf with different water contents on spectral reflectance in 'Fuji' apple and purple leaf flowering plum, respectively.
Figure 17B:
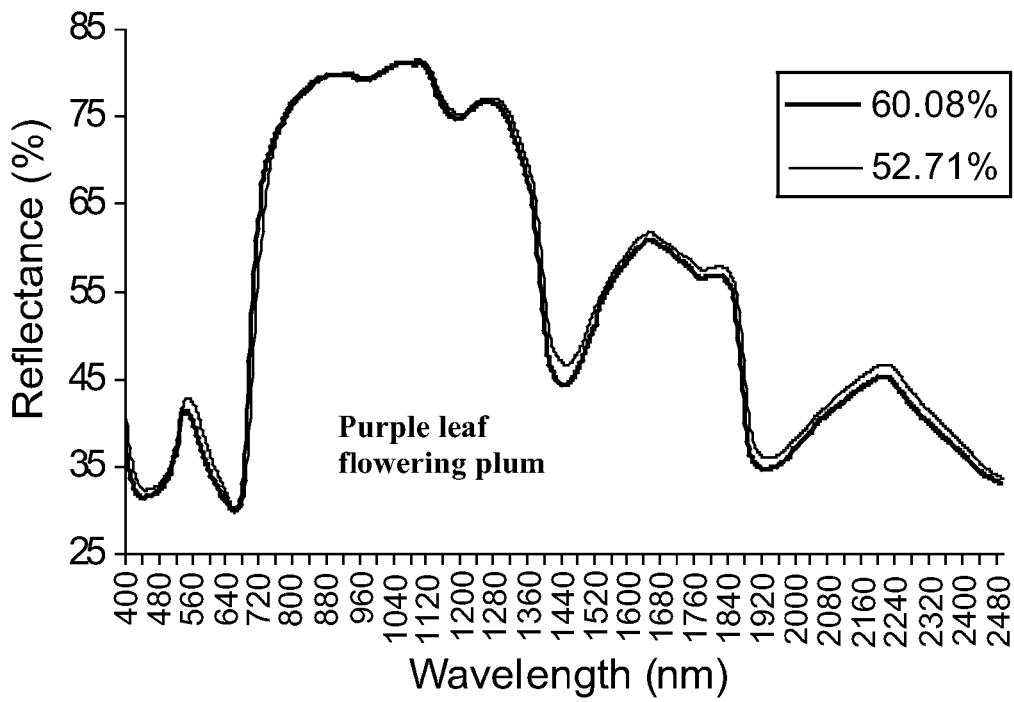
Figure 19C:
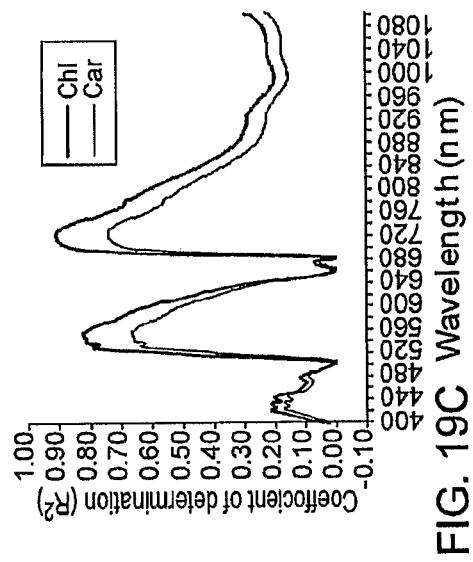
FIGS. 19A-D show graphs of the simple linear coefficient determination ($R^2$) between reflectance and Chl, Anth and Car contents in leaves of purple leaf flowering plum and purple leaf plum, and between reflectance and Chl and Car for Fuji apple and poplar.
Figure 19D:
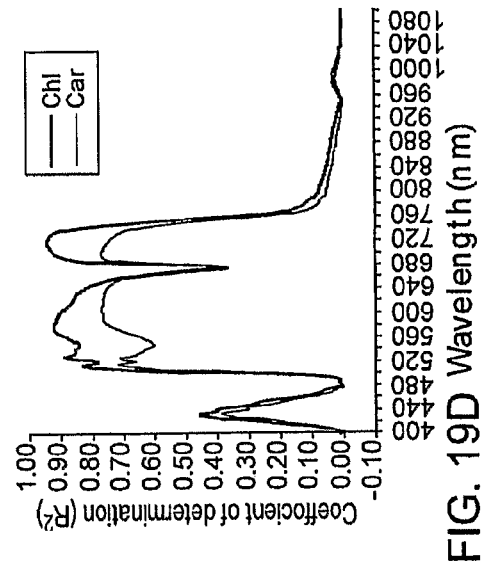
Figure 19A:
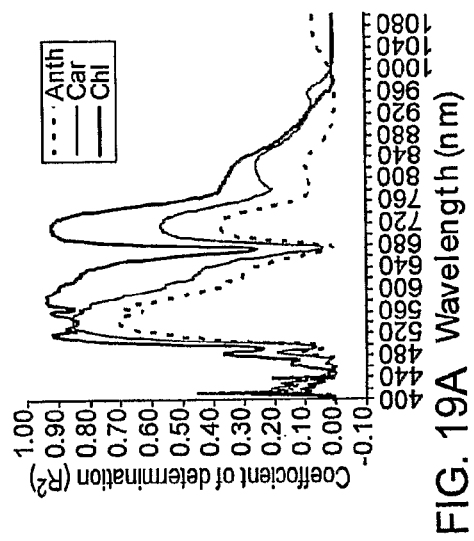
Figure 19B:
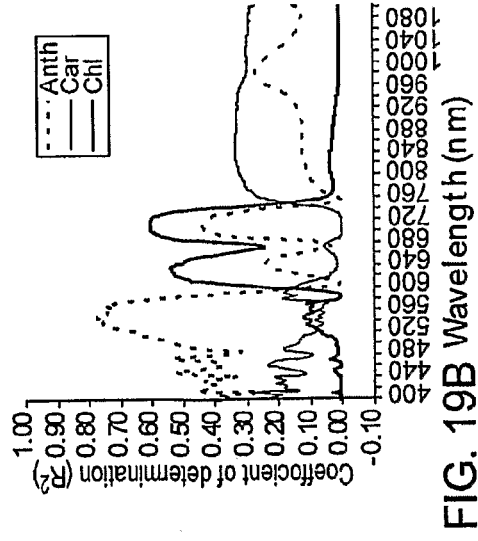

In an attempt to understand how Chl assessment was affected by leaf water status, reflectance of the same leaf was measured before and after varying degrees of dehydration. The results indicated that dehydration reduced light leaf penetration possibly due to leaf cell shrinkage and increasing density, which in turn increased leaf spectral reflectance in the ranges of green (540-600 nm), red edge (710-740 nm) and NIR (1350-2500 nm) in the leaf of 'Fuji' apple and purple leaf flowering plum (FIG. 17). However, leaf spectral reflectance in the wavelength range of 750 to 1000 nm was not significantly affected by dehydration. This was because the reflectance in range 750 to 1000 nm was not sensitive to the variation of leaf water content. Dehydration in the experiment did not significantly change leaf thickness enough to alter leaf reflectance in the range of 750 to 1000 nm; in contrast, dehydration was enough to increase visible reflectance by changing the leaf property.

Range of Leaf Chl Content and Clh a/b Ratio

Leaf Chl content is an important factor affecting algorithm adaptability for Chl assessments. In earlier investigations the reflectance minimum at wavelength 670-680 nm was employed for Chl analysis (Merzlyak et al. 2003). Our results indicated that the $R^2$ at wavelength 670-680 nm was smaller than in the wavebands of the green (540-600 nm) and red edge (700-730 nm). The wavebands in the green and red edge had larger reflectance coefficient determinations and smaller RMSE and were sensitive to a wide-range of Chl content from 160 to 1188 $\mu g \cdot m^{-2}$ (FIG. 18).

In previous literature the absorption maximum of chlorophyll a is at a wavelength that is 20 nm longer than that of chlorophyll b. Therefore, if the relative proportion of Chl a increased there would be a movement of the maximum absorption wavelength to longer wavelengths, independent of total Chl content (Guyot and Baret 1988). In our experiment, the optimum wavelength of Chl a in the green range was at a wavelength that was 2-18 nm longer than that of chlorophyll b in the leaf of 'Fuji' apple, poplar and purple leaf flowering plum that had larger $R^2$; whereas in the leaves of almond and purple leaf plum that had smaller $R^2$ the optimum wavelength of Chl a was 6-9 nm shorter than that of Chl b. Among anthocyanin-free species there was a trend that the species with higher Chl a/b ratio had a longer optimum wavelength in the green range. However, this trend did not hold in purple leaf plum and purple leaf flowering plum. In these anthocyanin-rich species, although the Chl a/b ratios were much smaller than that in anthocyanin-free species, their optimum wavelengths were much longer and shifted from green to red range in comparison to the optimum wavelength of anthocyanin-free species (Table 17). In contrast to the optimum wavelength in the green range that shifted to a longer wavelength with higher Chl a/b ratio, there was no consistent trend about the shift of optimum wavelength that affected by Chl a/b in the red edge among different species (Table 17).

TABLE 17

Contents of Chl a, Ch b, total Chl, carotenoids (Caro) and anthocyanin (Anth), ratio of Chl a/Chl b, total Chl/Caro and total Chl/Anth, the optimum wavelengths and the corresponding R and RMSE in both visible and red edge for 'Fuji' apple, poplar, almond, purple leaf flowering plum and purple leaf plum, respectively

| Species | Pigments | Pigment Range ($\mu g \cdot m^{-2}$) | Average ($\mu g \cdot m^{-2}$) | WL (nm) | $R^2$ | RMSE ($\mu g \cdot m^{-2}$) | WL (nm) | $R^2$ | RMSE ($\mu g \cdot m^{-2}$) |
|---|---|---|---|---|---|---|---|---|---|
| 'Fuji' apple | Chl a | 200.16~926.40 | 563.28 | 552 | 0.7785 | 96.61 | 720 | 0.9198 | 57.69 |
| | Chl b | 61.39~262.33 | 161.86 | 550 | 0.7225 | 26.94 | 717 | 0.8465 | 19.59 |
| | Total Chl | 261.55~1188.72 | 725.14 | 552 | 0.7695 | 122.07 | 720 | 0.9072 | 75.76 |
| | Chla/Chlb | 3.26~3.53 | 3.40 | | | | | | |

TABLE 17-continued

Contents of Chl a, Ch b, total Chl, carotenoids (Caro) and anthocyanin (Anth), ratio of Chl a/Chl b, total Chl/Caro and total Chl/Anth, the optimum wavelengths and the corresponding R and RMSE in both visible and red edge for 'Fuji' apple, poplar, almond, purple leaf flowering plum and purple leaf plum, respectively

| Species | Pigments | Pigment Range ($\mu g \cdot m^{-2}$) | Average ($\mu g \cdot m^{-2}$) | WL (nm) | $R^2$ | RMSE ($\mu g \cdot m^{-2}$) | WL (nm) | $R^2$ | RMSE ($\mu g \cdot m^{-2}$) |
|---|---|---|---|---|---|---|---|---|---|
| | Caro | 121.09~314.26 | 217.68 | | | | | | |
| | Total Chl/Caro | 2.16~3.78 | 2.97 | | | | | | |
| Poplar | Chl a | 131.22~509.58 | 320.40 | 581 | 0.9497 | 21.79 | 715 | 0.9579 | 18.97 |
| | Chl b | 24.64~149.95 | 87.30 | 563 | 0.7440 | 16.44 | 730 | 0.7801 | 14.51 |
| | Total Chl | 160.45~659.54 | 410.00 | 575 | 0.9166 | 38.23 | 720 | 0.9352 | 33.48 |
| | Chla/Chlb | 5.33~3.40 | 4.36 | | | | | | |
| | Caro | 80.22~153.80 | 117.01 | | | | | | |
| | Total Chl/Caro | 2.00~4.29 | 3.14 | | | | | | |
| Almond | Chl a | 133.35~552.90 | 343.13 | 550 | 0.8740 | 36.76 | 710 | 0.8678 | 37.69 |
| | Chl b | 39.97~157.55 | 98.76 | 558 | 0.8256 | 10.79 | 710 | 0.8144 | 11.14 |
| | Total Chl | 173.32~710.45 | 441.89 | 550 | 0.8737 | 47.55 | 710 | 0.8667 | 48.83 |
| | Chla/Chlb | 3.34~3.51 | 3.42 | | | | | | |
| | Caro | 163.01~323.34 | 243.18 | | | | | | |
| | Total Chl/Caro | 1.06~2.20 | 1.63 | | | | | | |
| Purple leaf flowering plum | Chl a | 216.48~548.78 | 450.65 | 592 | 0.9388 | 26.64 | 716 | 0.9291 | 28.68 |
| | Chl b | 80.81~201.41 | 164.59 | 580 | 0.9207 | 11.14 | 714 | 0.8750 | 13.99 |
| | Total Chl | 297.29~750.20 | 615.24 | 590 | 0.9339 | 37.79 | 714 | 0.9170 | 42.37 |
| | Chla/Chlb | 2.55~2.92 | 2.73 | | | | | | |
| | Anth | 157.17~297.25 | 232.40 | | | | | | |
| | Total Chl/Anth | 1.89~2.52 | 2.65 | | | | | | |
| | Caro | 121.31~215.97 | 187.42 | | | | | | |
| | Total Chl/Caro | 2.45~3.47 | 3.28 | | | | | | |
| Purple leaf plum | Chl a | 120.94~366.81 | 248.92 | 630 | 0.5392 | 39.82 | 712 | 0.6020 | 37.01 |
| | Chl b | 44.24~138.69 | 99.33 | 636 | 0.5105 | 16.29 | 714 | 0.5870 | 14.96 |
| | Total Chl | 165.18~505.50 | 348.25 | 636 | 0.5354 | 55.62 | 714 | 0.6027 | 51.43 |
| | Chla/Chlb | 2.27~2.73 | 2.51 | | | | | | |
| | Anth | 145.56~624.93 | 361.33 | | | | | | |
| | Total Chl/Anth | 0.81~1.13 | 0.96 | | | | | | |
| | Caro | 27.71~56.26 | 39.65 | | | | | | |
| | Total Chl/Caro | 5.96~8.99 | 8.78 | | | | | | |

Influence of Leaf Red and Other Pigments

Plant leaves contain a number of pigments, besides Chl, anthocyanins and carotenoids are major pigments that absorb radiation and could therefore affect Chl measurements. From July to August, almost no anthocyanins could be detected in the leaf of 'Fuji' apple, poplar and almond. However, in the leaf of purple leaf plum and purple leaf flowering cherry the anthocyanins content was about 145.56~624.93 $\mu g \cdot nm^2$ and 157.17~297.25 $\mu g \cdot m^{-2}$, respectively. The simple linear regression $R^2$ between reflectance reading and Chl content at each wavelength indicated that there were two evident peaks in all the plant species tested. However the Chl $R^2$ peaks in the leaf of 'Fuji' apple, poplar and purple leaf flowering cherry were significantly larger than that in purple leaf plum (FIG. 19).

The red edge optimum wavelength in the anthocyanin-free species of 'Fuji' apple, poplar and almond was 720 nm, 720 nm and 710 nm respectively, which was only a few nanometer difference from the red edge optimum wavelength (714 nm) in the anthocyanin-rich species of red edge for purple leaf plum and purple leaf flowering cherry (Table 17). In contrast to the optimum red edge wavelength, the optimum wavelength in the visible range of the anthocyanin-rich species shifted greatly from shorter (green) wavelength to the longer (red) wavelength in comparison to the optimum wavelength of the anthocyanin-free species (Table 17).

In anthocyanin-free leaves of apple, poplar and almond both green range wavelength (550-580 nm) and the red edge wavelength (700-740 nm) could be used for Chl content assessment. However the wavelengths at red edge had higher Chl sensitivity, larger $R^2$ and smaller RMSE. In anthocyanin-rich leaves of purple leaf plum and purple leaf flowering cherry there were two major anthocyanin $R^2$ peaks that overlapped with two Chl $R^2$ peaks in the range of green (500-600 nm) and red edge (700-750 nm), respectively. In purple leaf flowering cherry the Chl $R^2$ in both green and red edge were very good and not affected by the existence of anthocyanin at content of 157.17~297.2511 $g \cdot m^{-2}$ (FIG. 19 and Table 17). Our results indicated that the content of anthocyanin in the leaves of purple leaf flowering cherry was closely related and proportional to Chl content ($R^2=0.5512$). In contrast, in the leaves of purple leaf plum lack of relationship between Chl and anthocyanin content ($R^2=0.1933$) resulted in the existence of anthocyanin in the leaf of purple leaf plum significantly decreased the $R^2$ in both visible and red edge in comparison to the other species.

Carotenoid content was closely and proportionally related to Chl content. Therefore, although the two $R^2$ reflectance peaks of Chl were overlapped by two the reflectance $R^2$ peaks of carotenoid, the Chl reflectance $R^2$ was larger than the reflectance $R^2$ carotenoid peaks and had no effect on the Chl reflectance assessment.

Discussion

An important objective of investigation into the relationship between leaf optical properties is to find indices that hold across a wide range of species and functional groups (Andrew et al. 2002). However, this has proven difficult to achieve (Andrew et al. 2002). Gamon & Surfus (1999) demonstrated that the relationship between normalized difference vegetation index (NDVI) and total Chl is markedly different for the coniferous *Pseudotsuga menziesii* and the herbaceous *Helianthus annuus*; they suggest this may be due to differences in leaf morphology and structure. Andrew et al. (2002) believed the differences in leaf structure, and the associated effects severely impair our ability to use many indices across a wide range of vegetation types. In addition, such differences make it unlikely that calibration equations from one study can be directly applied to leaves with different structural attributes (Andrew et al. 2002). Our result indicated that using the Chl related optimum wavelength in the algorithm or indices was very important. There were two optimum wavebands that related to the Chl status of the species tested: one in the visible range of 552-630 nm, the other in red edge of 710-720 nm (Table 14). Although the Chl related optimum wavelengths for all the species tested were in two narrow wavebands, the difference of optimum wavelength among species was enough to impair the ability of an index to be used across a wide range of genotypes. Our results indicate that a slight variation of only a few nanometers away from the optimum wavelength could significantly affect the regression $R^2$ and RMSE. This was the reason why an index or a calibration equation from one study could not be directly applied to leaves with different structural attributes.

The effect of leaf morphology and structure also had an effect on Chl assessment among cultivars within the same species. Our results indicated that the optimum wavelength for different apple cultivars and species of plants varied. Therefore, in order to obtain accurate Chl assessments, selecting the Chl related optimum wavelength to develop an algorithm for specific cultivar is very important.

Leaf Chl content is one important factor affecting algorithm adaptability for Chl assessments. In earlier investigations reflectance minimum at wavelength 670-680 nm was employed for Chl analysis (Merzlyak et al. 2003). Although the algorithms developed for these wavelengths showed a good sensitivity and linearity at low Chl content range, they became rapidly saturated with an increase in the pigment content over 100-150 $\mu g \cdot m^{-2}$ (Gitelson et al 1996, Gitelson and Merzlyak 1994, Buschmann and Nagel 1993). Our analysis showed that spectral regions in the green (540-600 nm) and red edge (700-730 nm) had larger reflectance coefficient determinations with smaller RMSE and were sensitive to wide-range of Chl content from 160 to 1188 $\mu g \cdot m^{-2}$ (FIG. 18). It was found that reflectance in these bands were hyperbolically related to Chl content (Gitelson and Merzlyak 1994, Gitelson and Merzlyak 1996, Lichtenthaler et al. 1996). It should be noted that Chl absorption coefficients were very low in these bands. This is apparently universal feature of plant reflectance spectra was used as a basis in the development of algorithms for estimation of Chl and other pigment (Merzlyak et al. 2003).

One of the requirements for reliable algorithms of pigment analysis is their low sensitivity to morphological-anatomical traits of plant tissues (Merzlyak et al. 2003). For leaves differing in pigment content, the lowest variation of reflectance at wavelengths longer than 500 nm was found in the NIR region (Gitelson and Merzlyak 1994, Lichtenthaler et al. 1996). Our result indicated the lowest variation of reflectance was at wavelengths 750-1100 nm. Since leaf pigments possess no measurable absorption in the NIR, the tissue reflectance in this region is apparently determined by "internal" optical properties related to leaf thickness, water content, and light scattering (Merzlyak et al. 2003).

In an attempt to understand how leaf optical properties (texture, thickness and/or density) affecting Chl assessment, the reflectance spectra of leaves with almost the same Chl content but different reflectance indicated that the higher the reflectance in the range of green (540-600 nm) and red edge (710-740 nm), the higher the reflectance in the NIR range of wavelength of 750-1750 nm (FIG. 16). The factors that govern the behavior of reflectance in the range of green (540-600 nm) and red edge (700-740 nm) were very different from the factors that govern the behavior of reflectance in the range of NIR (750-1750 nm). In the NIR range, an increase in reflectance might be caused by an increase in leaf thickness or density; in the range of green and red edge, an increase in reflectance indicates a decrease in Chl or other pigment content. In leaves with the same Chl content, an increase in leaf thickness might cause an increase in reflectance in the Chl insensitive NIR range and a relative decrease in Chl concentration on unit volume basis; which caused an increase in reflectance in green and red edge (FIG. 16). With the variation in leaf texture, reflectance in the range of green (540-600 nm), red edge (700-740 nm), and NIR (750-1100) varied in the same direction, therefore, by referencing green or red edge wavelengths that were sensitive to Chl to the NIR wavelength that were sensitive to leaf texture but insensitive to Chl, the effect of leaf texture on Chl assessment could be eliminated by the algorithms of simple ratio $R_{540-560}/R_{750-1100}$, $R_{700-740}/R_{750-1100}$ and normalized reflectance difference $(R_{540-560}-R_{750-1100})/(R_{540-560}+R_{750-1100})$, and $(R_{700-740}-R_{750-1100})/(R_{700-740}+R_{750-1100})$ to improve the regression $R^2$ and RMSE (Table 14). It is noteworthy that the ratio $R_{540-560}/R_{750-1100}$, $R_{700-740}/R_{750-1100}$ ratios possessed similar sensitivity to Chl content, which was due to high correlation between reflectance coefficients at 540-600 nm and 700-740 nm characteristic of healthy anthocyanin-free leaves.

Leaf water status is another important factor affecting Chl assessment. Our results indicated that dehydration reduced light leaf penetration by leaf cell shrinking and density increasing, which in turn increased leaf spectral reflectance in the ranges green (540-600 nm), red edge (710-740 nm) and NIR (1350-2500 nm) in the leaf of 'Fuji' apple and purple leaf flowering cherry (FIG. 17). However, leaf spectral reflectance in the wavelength range of 750-1000 nm that sensitive to leaf texture was not significantly affected by dehydration. This result further verified that the effect of leaf texture on reflectance can be eliminated by referencing green (540-600 nm) or red edge (700-740 nm) wavelengths that are sensitive to Chl to the NIR wavelength of 750-1100 nm that are sensitive to leaf texture but insensitive to Chl. Leaf water most sensitive wavelengths were in the range of 1420-1510 nm (FIG. 17). Therefore, the effect of leaf water status on reflectance may be eliminated by referencing the reflectance of Chl sensitive wavelength either in green or red edge to the water most sensitive wavelength of 1420-1510 nm.

Plant leave contains a number of chemical pigments, besides Chl, anthocyanins and carotenoids are two important group pigments that absorb radiation and could therefore affect Chl nondestructive measurement. Anthocyanins (represented mainly by cyanidin derivatives) localized in vacuoles within leaf cells were reported by researcher to possess an absorption maximum near 540-550 nm (Gitelson et al. 2001, Merzlyak and Chlvkunova 2000). Our results indicated that the anthocyanins even possessed a wider absorption range of 500-560 nm (FIG. 19). Since Chl absorption was significant in this region (FIG. 19), the contribution of anthocyanins to reflectance should be taken into account while assaying Chl (Current et al 1991).

Current et al (1990) reported that the linear relationship between reflectance and Chl at red edge was severely affected by the existence of anthocyanins in *Amaranthus tricolor* even if the concentration as low as 0.01 mg·g$^{-1}$. Our result indicated that in the leaf flowering plum the simple linear regression $R^2$ in both green and red edge were very good and not affected by the existence of anthocyanins at content of 157.17~297.25 μg·m$^{-2}$, whereas the in the leaf of red leaf plum in both green and red edge were severely impaired by the existence of anthocyanins (FIG. 19 and Table 17). The regression results between anthocyanin and Chl content indicated that anthocyanin content was closely related and proportional to Chl content leaves of purple leaf flowering cherry ($R^2$=0.5512). In contrast, lack of relationship between Chl and anthocyanin content ($R^2$=0.1933) in the leaves of purple leaf plum resulted in the interference of anthocyanin on Chl assessment. The accumulation of anthocyanin led to a significant $R^2$ decrease in 540-600 nm relative to 700-740 nm (FIG. 19 and Table 17). This greatly complicated the application of the $R_{750-1100}/R_{540-600}$ index for Chl assessment in the leaves of purple leaf plum. In contrast, our studies showed that the $R_{750-1100}/R_{700-740}$ index was less impaired and could be used for Chl analysis even at high anthocyanin content. Gitelson er al (2001) also reported that in assessing Chl content in anthocyanin content in plant leaves the algorithm $R_{NIR}/R700$ was better than $R_{NIR}/R_{550}$. In our experiment carotenoid content was closely and proportionally related to Chl content. Although two $R^2$ peaks of Chl related reflectance were overlapped by two $R^2$ peaks of carotenoid, the Chl reflectance $R^2$ was not affected by carotenoid.

Part VII

Methods of Transmission and Reflectance in Comparison with Hand-Held Chlorophyll Meters in Leaf Chlorophyll and Nitrogen Nondestructive Assessment In assessing the content of leaf chlorophyll (Chl) and nitrogen (N), SPAD-502 had smaller variability and standard error than CCM-200 and CM-1000. CM-1000, if tested based on constant sampling distance, had similar variability and standard error to that of CCM-200. However, if sampling distance not constant, it significantly increased the CM-1000 variability. A variation in sampling distance altered light intensity received by the light sensor to result in an overestimation or an underestimation of Chl or N. According to our result, CCM-200 sampling distance had larger incident variation than SPAD-502; this was one reason why it was not as accurate as SPAD-502. Another reason was the wavelength 660 nm used by CCM-200 was not as good as the wavelength 650 nm used by SPAD-502; the latter had a larger $R^2$ and smaller RMSE. Among the parameters of the hand-held Chl meters, Chl sensitive wavelength used by the meter is most important. Simple linear regression $R^2$ and RMSE between transmission/reflectance and Chl or N indicated that there were two $R^2$ peaks, one in green range (540-590 nm) and the other in red edge (700-730 nm). Larger $R^2$ with smaller RMSE indicated that the green and red edge could be used as optimum wavelength for Chl and N assessment. However, the N coefficient $R^2$ peaks were much smaller than that of Chl in both green and red edge, indicating that N assessment was more difficult than Chl. By comparing Chl sensitive wavelength used by different hand-held meters, wavelength 700 nm used by CM-1000 was better than wavelength 650 nm and 660 nm, however, inconstant sampling distance and inconsistent light intensity between ambient light sensor and sample target sensor made the CM-1000 less accurate than the other two meters. Transmission or reflectance with single optimum wavelength alone either in green or in red edge was more accurate than any of the hand-held meter in measuring both Chl and N; however, optimum wavelength if incorporated with one NIR wavelength from 750 to 1000 nm as the form of simple ratio or any other superior algorithm to compensate for leaf texture difference further increased the value of $R^2$ and regression accuracy. This was especially important if the $R^2$ of single wavelength was smaller than 0.8000 for Chl or 0.6000 for N. Optimum wavelengths in both green and red edge differed among species; fortunately, the variation was relatively small. Thus, it is possible to select one optimum wavelength in green or red edge that is sensitive to Chl in combination with one NIR wavelength from 750-1000 nm that is insensitive to Chl but sensitive to leaf texture to develop a more accurate algorithm or meter than the current hand-held meter for assessing Chl and N in the leaf of different species.

Introduction

Nitrogen (N) is the major nutrient element that most frequently limits the growth and productivity of non-leguminous plants (Below 1995, Meisinger 1984). An excess of applied N may lead to contamination of ground and surface water supplies while too little N fertilizer can result in reduced yield and therefore reduce profit (Bullock and Anderson 1998). Efficient management of N fertilization to achieve an optimum productivity while preserving and enhancing the quality is an important objective in modern agricultural system and usually requires frequent plant and soil testing to ensure that neither too much nor too little N is applied. The standard methods for plant N measurement are destructive and time consuming (Handson and Shelley 1993).

Since much of leaf N is incorporated in chlorophyll (Chl), leaf N content is closely related to leaf Chl concentration and photosynthetic capacity (Evans 1983, Seemann et al. 1987, Syvertsen 1987, Uchlda et al. 1982; Yoshida and Coronel, 1976). Quantifying Chl content gives an indirect measure of nutrient status (Filella et al. 1995, Moran et al. 2000). However, as the sensitive indicator of various stresses, plant nutrition status and photosynthetic ability, Chl traditionally is quantified by time-consuming wet chemical methods in solvent extraction. More recently, noninvasive optical hand-held Chl meters, based on principles of light transmission or reflectance have been developed to estimate leaf relative Chl and N. These meters, including the most popular used SPAD-502 (Minolta Corp., Japan), CCM-200 Chl Content Meter (Opti-Science, Inc., Tyngsboro, Mass.), and CM 1000 Chl Meter (Spectrum Technologies, Inc., Plainfield, Ill.), have been found to correlated positively with leaf Chl and N content in large amount of plant species include annual, perennial and wood plants (Bullock and Anderson 1998, Costa et al. 2001, Kantety et al 1996, Nielsen et al 1995, Richardson et al 2002, Schepers et al 1992, Markwell et al 1995, Turner and Jund. 1991). The accuracy of these hand-held chlorophyll meters differed one from another although all of them use two wavelengths, one Chl sensitive wavelength and one Chl insensitive wavelength, to assess leaf Chl (Markwell et al 1995, Minolta 1989, Opti-Science 2000, Whaley 2001).

Compared to hand-held Chl meters, which just use two wavelengths and yield a single index value, the portable reflectometers can measure reflectance across the entire spectrum from ultraviolet, visible to near-infrared wavelengths (Curran et al. 1990, Adams et al 1999, Datt 1999, Gamon & Surfus 1999); and the spectroradiometer can even measure both reflectance and transmittance of the entire spectrum (Schepers et al. 1996). Thus, with the entire spectrum result, researchers can get almost infinite number of indices with different transformation and get more useful information (Richardson et al. 2002). Moreover, it gives researcher's ability to choose and evaluate the optimum wavelength and indices for Chl and other pigments assessment (Adams et al. 1999, Lichtenthaler et al. 1966, Merzlyak et al 2003).

Many researchers have studied the effect of plant leaf genotype (Bullock and Anderson 1998, Peng et al. 1993, Schepers et al 1992, Sunderman and Lamm 1991, Takebe and Yoneyama, 1989.), developmental stage (Neilsen et al 1995, Peng et al. 1993, Piekielek and Fox 1992), thickness (Campbell et al. 1990, Chlariello et al 1989, Neilsen et al 1995, Osmond et al 198, 9, Peng et al. 1993), Chl and other pigments content (Richardson et al. 2002), leaf water status (Martinez and Guiamet 2004) and other characteristics on accuracy of transmission based hand-held meter SPAD-502 (Markwell et al (1995). Two studies have discussed the effect principle of how leaf characteristics on meter accuracy by altering leaf light scatteration, reflection, absorption and transmission (Monje & Bugbee 1992; Markwell et al., 1995). However, we are not aware of any studies that attempted a comparative test on meter parameter (i.e., meter wavelength, the consistency and constancy of sampling distance and light source) among different hand-held meters to determine why one meter is better than another. Richardson et al. (2002) compared two hand-held transmission Chl meters (SPAD-502 and CCM-200) with the reflectance indices developed by remote sensing and concluded that relative Chl content was better estimated by reflectance rather than transmission. However, the wavelengths used in the reflectance indices were different from that used in hand-held Chl meters. Therefore, it might be the wavelength difference rather than the method of reflectance or transmission caused the difference. According to our test, meter wavelength, especially the chlorophyll related wavelength, is the most important parameter to meter accuracy. The results of indices developed with different wavelengths are very different. Moreover, we are not aware of any attempt made to compare the Chl related wavelength used by different hand-held Chl meter with a possible better wavelength selected from ultraviolet, visible to near-infrared of the entire spectrum. Thus, the purpose of this study is to compare the parameters used by different hand-held Chl meter to explain why one meter is better than another; and compare the wavelength used by different hand-held Chl meter other factors including leaf characteristics on meter accuracy to find is there any possible to develop a better chlorophyll meter for Ch and N noninvasive assessment.

Materials and Methods

Plant Materials

'Nonpareil' almond (*Prunus dulcis* (Mill.) D. A. Webb), poplar (UCC-1, a hybrid of *Populus trichocarpa×P. deltoides*, Union Camp, Princeton, N.J.) and bench-grafted Fuji apple (*Malus domestica* Borkh) trees on M.26 rootstocks were grown in 7.2 L pots with a medium of 1 peat moss:2 pumice:1 sandy loam soil (v:v) in a lathhouse from 26 March to 5 June. Beginning from budbreak in early May, they were fertilized every 2 weeks with 10.7 mM N, using Plantexâ 20N-10P$_2$O$_5$-20K$_2$O water-soluble fertilizer with micronutrients (Plantex Corp., Ontario, Canada). When the new shoots were approximately 15 cm long, plants were moved to full sunlight. Thereafter, they were fertilized weekly with Plantexâ for 3 weeks. Beginning on 30 June, plants were fertilized twice weekly with one of the six N concentrations (0, 2.5, 5, 7.5, 10, or 20 mM N from NH$_4$NO$_3$) by applying 300 ml of a modified Hoagland's solution to each pot until the end of September. At the end of August, 12 fresh leaves from each N fertigation treatment plants were harvested and immediately placed into plastic bags for transport to the laboratory.

Hand-Held Chl Meters and the Measurement

Three commercially available hand-held Chl meters were evaluated: the SPAD-502, the CCM-200, and the CM 1000. The SPAD-502 weighs 225 g, has a 0.06 cm$^2$ measurement area, and calculates an index in SPAD units based on absorbance at 650 and 940 nm. The claimed accuracy of the SPAD-502 is ±1.0 SPAD units. The CCM-200 weighs 180 g, has a 0.71 cm$^2$ measurement area, and calculates a Chl content index (CCI) based on absorbance measurements at 660 and 940 nm. The claimed accuracy of the CCM-200 is ±1.0 CCI units. The CM-1000 weights 692 g and calculates an index in CM-1000 units based on reflectance at 700 and 840 nm. The recommended sampling distance is from 28.4 to 183.0 cm corresponded with the sampling area of 1.10 to 18.8 cm in diameter that is outlined with the high powered lasers. All instruments were calibrated before measurements by following the procedures recommended by the manufactures. Five separate measurements with each hand-held meter were made on each leaf and the mean of these measurements was used for all subsequent analyses.

Leaf Transmittance and Reflectance Measurement

Leaf discs taken with a 2.85 cm$^2$ cork borers were immediately scanned by using Li-1800 spectroradiometer (Li-Cor Inc., Lincoln, Nebr.) from 300 nm to 1100 nm with 1 nm interval to measure the spectral reflectance. Two scans were made per sample and then average. The transmittance or reflectance spectrum for each scan was calculated as $T_\lambda$ (or $R_\lambda$)=leaf radiance at wavelength $\lambda$/transmittance (reflectance) standard radiance at wavelength $\lambda$, and was averaged across the two separate scans made on each leaf disc.

Chlorophyll and N Analysis

After scan the leaf discs were then extracted in 80% (v/v) acetone at 4° C. in the dark for Chl content assessment. Absorptance of the extract was measured with a Shimadzu UV-visible spectrophotometer UV-1601. Total Chl was calculated according to Lichtenthaler and Wellburn (1983). N content was determined by following the Kjeldahl procedure (Horneck et al., 1989).

Variation of Sampling Distance on CM-1000

In order to test the effect of sampling distance on the reading of CM-1000, 3 poplar leaves with Chl content of 480, 574 and 655 µg·m$^{-2}$ were measured, respectively, from sampling distance of 30 to 90 cm with 10 cm interval. At every 10 cm interval each leaf was measured 10 times and the mean of these measurements was used as the result of different distance.

Effect Shading and User Facing Direction on the Index of CM-1000

Effect of shading between ambient light sensors and target sample on CM-1000 index measured by using the same leaf with the methods of both ambient light sensors and target leaf exposed to sun light, ambient light sensors exposed to the sun light whereas target leaf in the shade, both ambient light sensors and target leaf in the shade, and ambient light sensors in the shade whereas target leaf exposed to the sun light. The effect of user facing direction in on CM-1000 index was measured by using the same leaf at 9:00 am with the methods facing west while the sun at the back of the user, facing south, facing north, and facing east while the sun in the front of the user. For each shading or facing method the same leaf was repeatedly measured 10 times and the mean of these measurements was used as the result.

Simple Linear Regression Coefficient Determination ($R^2$) and Root Mean Square Error (RSME)

Simple linear regression between the reading of each wavelength and Chls (Chl a, Chl b or Ch a+b) was developed for wavelength from 300 nm to 1100 nm with 1 nm interval. The related $R^2$ and RSME curves of Chl a, Chl b and Ch a+b were developed at each wavelength for optimum wavelength selection, respectively.

Leaf Transmittance Reflectance Indices Calculations

In order to compare with the commercial hand-held Chl meters, the reading of transmittance and reflectance at wavelength 650 nm, 700 nm, 840 nm, 940 nm and at the optimum wavelength selected for almond, poplar and 'Fuji' apple were selected and transformed by using published indices which have been recommended as excellent indicator of foliar Chl. These recommended indices include simple ratio (SR), normalized difference vegetation index (NDVI), and reflectance integral index (RII) (Gitelson & Merzlyak, 1994).

(1) The SR is calculated as the ratio of two single wavelengths. The SR is also called vegetation index (VI) if the ratio is between the NIR region and red region wavelengths (Andrew et al 2002). The simple ratios used here in our experiment are the ratios of optimum wavelength selected in both the visible green range (540-590 nm) and the red edge (700-740 nm) divided by the NIR wavelength 840 or 940 nm (2) NDVI is an index strongly correlated with leaf Chl content (Gamon et al. 1995; Peñuelas & Filella 1998, Richardson et al. 2002). It is a standard index used in remote sensing (Gamon and Qiu 1999). The NDVI is calculated as $(R_{NIR}-R_{red})/(R_{NIR}+R_{red})$. The most popular NDVI is calculated as NDVI=(R750−R675)/(R750+R675). The revised version of the NDVI is called Chl Normalized difference index (Chl NDI), which is better correlated with leaf Chl content and more sensitive to a wider range of Chl contents calculated as Chl NDI=(R750−R705)/(R750+R705) (Richardson et al. 2002, Gitelson and Merzlyak 1994). We use the optimum wavelength selected for different species in both the visible green range (540-590 nm) and the red edge (700-740 nm) in combination of the NIR wavelength 940 nm to develop a similar algorithm, Chl NDI=(R750−R705)/(R750+R705), to compare with the published algorithm Chl NDI for both transmission and reflectance.

(3) RII is calculated using a discrete summation approximation to the following integral:

$$RII = \int_{705}^{750} (R_\lambda / R_{705} - 1) d\lambda$$

In our experiment we calculated both reflectance integral index (RII) and transmission integral index (TII), we found transmission or reflectance from 700 to 740 nm divided by wavelength 710 nm produced a better result.

$$RII = \int_{700}^{740} (R_\lambda / R_{710} - 1) d\lambda \quad TII = \int_{700}^{740} (T_\lambda / T_{710} - 1) d\lambda$$

Results

Comparison of Different Meter Variability in Assessing Leaf Chl

Figures 24A, 24B, 24C, 24D, 24E, 24F, 25:
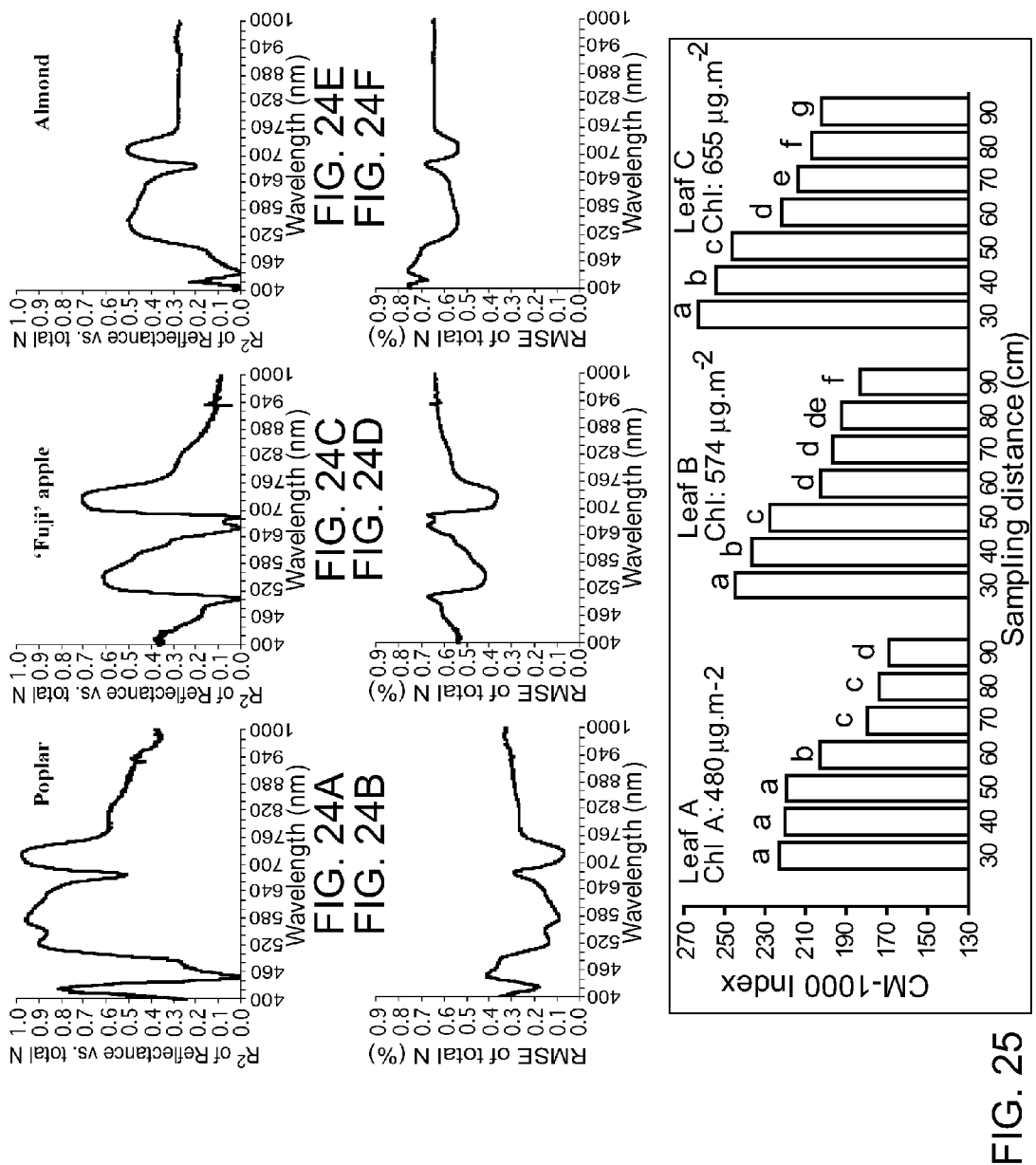
FIGS. 24A-24F show graphs of the $R^2$ and RMSE of total N estimated by reflectance in poplar, Fuji apple and almond leaves.

In order to compare the variability of different hand-held meters in Chl and N assessment, three 'Fuji' apple leaves with different Chl and N contents were selected. Each leaf was repeatedly measured 24 times with SPAD and CCM-200, respectively, by closing the sampling head with different pressure to measure the variation of sampling distance on the meter repeatability. The repeatability of CM-1000 for each leaf was also measured 24 times at a constant sampling distance of 50 cm. Unfortunately for same leaf different meter had different reading or meter index (Table 18), therefore, it is difficult to compare the accuracy among different meters according to meter original reading. However, meter reading could be transformed into Chl or N content based on unit meter index Chl content or unit meter index N content. The transformed results showed that SPAD meter had much smaller standard error indicating it was more accurate than CCM-200 and CM-1000 in assessing Chl and N (Table 19 and 20). CCM-200 and CM-1000 had similar standard error indicating their variability was similar, however, in this experiment the CM-1000 result was based on constant sampling distance, which significantly decreased the variation. If sampling distance not constant when measurement was taken, the variation was much bigger (FIG. 25).

TABLE 18

Equipment variability as meter reading in estimating Chl in 3 'Fuji' apple leaves with different Chl and N contents

| Leaf Chl ($\mu g \cdot m^{-2}$) | Leaf N (%) | Equipment | Reading Minimum | Reading Maximum | Range | Mean | Chl/unit Index | Reading SD[z] | Reading SE[y] |
|---|---|---|---|---|---|---|---|---|---|
| 378.30 | 1.5870 | SPAD | 38.60 | 39.00 | 0.40 | 38.84 | 9.74 | 0.13 | 0.04 |
| | | CM-200 | 24.50 | 29.00 | 4.50 | 26.96 | 14.03 | 1.65 | 0.41 |
| | | CCM-1000 | 172.00 | 196.00 | 24.00 | 185.23 | 2.04 | 7.68 | 2.05 |
| 515.62 | 1.9731 | SPAD | 46.00 | 47.20 | 1.20 | 46.51 | 11.09 | 0.40 | 0.10 |
| | | CM-200 | 49.60 | 55.20 | 5.60 | 52.56 | 9.81 | 2.27 | 0.57 |
| | | CCM-1000 | 192.00 | 221.00 | 29.00 | 204.64 | 2.52 | 9.42 | 3.81 |
| 708.06 | 2.3874 | SPAD | 55.70 | 57.00 | 1.30 | 56.29 | 12.58 | 0.40 | 0.13 |
| | | CM-200 | 73.10 | 85.90 | 12.80 | 81.12 | 8.73 | 4.44 | 1.28 |
| | | CCM-1000 | 211.00 | 247.00 | 36.00 | 231.25 | 3.06 | 12.78 | 3.80 |

[z]Meter index standard deviation;
[y]Meter index standard error

TABLE 19

Equipment variability in estimating
Chl in 3 'Fuji' apple leaves with different Chl contents

| Leaf Chl ($\mu g \cdot m^{-2}$) | Equipment | Chl/unit Index | Chl Minimum ($\mu g \cdot m^{-2}$) | Chl Maximum ($\mu g \cdot m^{-2}$) | Range ($\mu g \cdot m^{-2}$) | Mean ($\mu g \cdot m^{-2}$) | Chl SD$^z$ | Chl SE$^y$ |
|---|---|---|---|---|---|---|---|---|
| 378.30 | SPAD | 9.74 | 375.95 | 379.84 | 3.90 | 378.30 | 1.28 | 0.37 |
| | CM-200 | 14.03 | 343.83 | 406.98 | 63.15 | 378.30 | 23.13 | 5.78 |
| | CCM-1000 | 2.04 | 351.28 | 400.30 | 49.02 | 378.30 | 15.69 | 4.19 |
| 515.62 | SPAD | 11.09 | 509.94 | 523.25 | 13.30 | 515.62 | 4.45 | 1.11 |
| | CM-200 | 9.81 | 486.56 | 541.50 | 54.93 | 515.62 | 22.28 | 5.57 |
| | CCM-1000 | 2.52 | 483.77 | 556.84 | 73.07 | 515.62 | 23.74 | 7.33 |
| 708.06 | SPAD | 12.58 | 700.64 | 716.99 | 16.35 | 708.06 | 5.08 | 1.61 |
| | CM-200 | 8.73 | 638.09 | 749.82 | 111.73 | 708.06 | 38.72 | 11.18 |
| | CCM-1000 | 3.06 | 646.06 | 756.29 | 110.23 | 708.06 | 39.13 | 11.64 |

$^z$Meter Chl standard deviation;
$^y$Meter Chl standard error

TABLE 20

Equipment variability in estimating
N in 3 'Fuji' apple leaves with different N contents

| N (%) | Meter | N/Unit Index | N Minimum (%) | N Maximum (%) | Range (%) | Mean (%) | N SD$^z$ | N SE$^y$ |
|---|---|---|---|---|---|---|---|---|
| 1.5870 | SPAD | 0.0409 | 1.5771 | 1.5934 | 0.0163 | 1.5870 | 0.0054 | 0.0015 |
| | CM-200 | 0.0589 | 1.4424 | 1.7073 | 0.2649 | 1.5870 | 0.0970 | 0.0243 |
| | CCM-1000 | 0.0086 | 1.4736 | 1.6792 | 0.2056 | 1.5870 | 0.0658 | 0.0176 |
| 1.9731 | SPAD | 0.0424 | 1.9514 | 2.0023 | 0.0509 | 1.9731 | 0.0170 | 0.0043 |
| | CM-200 | 0.0375 | 1.8619 | 2.0721 | 0.2102 | 1.9731 | 0.0853 | 0.0213 |
| | CCM-1000 | 0.0096 | 1.8512 | 2.1308 | 0.2796 | 1.9731 | 0.0909 | 0.0280 |
| 2.3874 | SPAD | 0.0424 | 2.3624 | 2.4175 | 0.0551 | 2.3874 | 0.0171 | 0.0054 |
| | CM-200 | 0.0294 | 2.1514 | 2.5282 | 0.3767 | 2.3874 | 0.1306 | 0.0377 |
| | CCM-1000 | 0.0103 | 2.1783 | 2.5500 | 0.3717 | 2.3874 | 0.1319 | 0.0392 |

Relationship of Indices Among Different Meters

There was a close curvilinear relationship among the indices of different meters (FIG. 20). The relationship was closer between the indices of SPAD-502 and CCM-200 than that between SPAD-502 and CM-1000 and between CCM-200 and CM-1000. Furthermore, the correlation was tightest at low level of Chl and became loose soon from there up.

Optimum Wavelength for Chl and N Assessments

Chl sensitive wavelength used by the meter is the most important factor affecting meter accuracy. In order to evaluate the wavelengths that optimum for Chl and N assessment, simple linear regression $R^2$ and related RMSE between transmission/reflectance and Chl or N were analyzed for each wavelength from 300 to 1100 nm. The results indicated that there were two Chl coefficient $R^2$ peaks, one in green range (540-590 nm) the other in red edge (700-730 nm), corresponded with the lowest RMSE for both transmission and reflectance in 'Fuji' apple, poplar and almond (FIGS. 21 and 22). The difference was that the $R^2$ peak of transmission in the green range was wider than that of reflectance in all species. There were also two N coefficient $R^2$ peaks corresponding with the lowest RMSE similar to that of Chl for both transmission and reflectance (FIGS. 23 and 24). Larger $R^2$ with smaller RMSE indicated that the green and red edge could be used for both Chl and N assessment. However, the N coefficient $R^2$ peaks were much smaller than that of Chl, indicating that N assessment is more difficult than Chl.

By comparing the Chl related wavelength 650 nm, 660 nm and 700 nm used in SPAD-502, CCM-200 and CM-1000, respectively; we found, just according to the $R^2$ and RMSE of Chl related wavelength used in the meter, CM-1000 should be more accurate than SPAD-502 and CCM-200, because wavelength 700 nm used in CM-1000 has larger $R^2$ and smaller RMSE than that of wavelength 650 nm used in SPAD-502 and wavelength 660 nm used in CCM-200 (Tables 18 and 19). However, the result indicated that CM-1000 was less accurate than SPAD-502 and CCM-200, indicating that, in addition to Chl related wavelength, other factors like constant sampling distance and light source were also very important to meter accuracy. The wavelengths of two transmission based handheld Chl meters are very similar, however, the wavelength 650 nm used in SPAD-502 had a larger $R^2$ and smaller RMSE indicating that the wavelength 650 nm used in SPAD-502 is better than the wavelength 660 nm used in CCM-200 (Table 21 and 22).

TABLE 21

Comparison of optimum wavelengths related $R^2$ and RMSE to that of wavelength 650 nm used in SPAD and wavelength 660 nm used in CCM-200 and that of wavelength 700 nm used in CM-1000 for assessing Chl in the leaf of in poplar, 'Fuji' apple and almond

| | Plant Species | Visible WL (nm) | R2 | RMSE ($\mu g \cdot m^{-2}$) | Red edge WL (nm) | R2 | RMSE ($\mu g \cdot m^{-2}$) |
|---|---|---|---|---|---|---|---|
| Transmission | Poplar | 580 | 0.9357 | 30.38 | 704 | 0.9294 | 33.49 |
| | | 650 | 0.8768 | 34.26 | 700 | 0.9271 | 35.23 |
| | | 660 | 0.7921 | 40.43 | | | |
| | Fuji | 552 | 0.8844 | 87.00 | 712 | 0.9144 | 74.86 |
| | | 650 | 0.7830 | 119.18 | 700 | 0.9071 | 77.97 |
| | | 660 | 0.78601 | 118.34 | | | |
| | Almond | 567 | 0.7977 | 60.17 | 705 | 0.8309 | 55.03 |
| | | 650 | 0.6025 | 84.36 | 700 | 0.8225 | 56.37 |
| | | 660 | 0.4944 | 95.14 | | | |
| Reflectance | Poplar | 575 | 0.9166 | 38.23 | 720 | 0.9352 | 33.48 |
| | | 650 | 0.7604 | 88.81 | 700 | 0.8903 | 44.97 |
| | | 660 | 0.7001 | 93.11 | | | |
| | Fuji | 552 | 0.7696 | 122.07 | 717 | 0.9073 | 77.41 |
| | | 650 | 0.1242 | 237.96 | 700 | 0.8131 | 109.94 |
| | | 660 | 0.0048 | 253.67 | | | |
| | Almond | 550 | 0.8737 | 47.55 | 710 | 0.8668 | 48.83 |
| | | 650 | 0.6957 | 73.81 | 700 | 0.8414 | 53.28 |
| | | 660 | 0.6332 | 81.03 | | | |

TABLE 22

Comparison of optimum wavelengths related $R^2$ and RMSE to that of wavelength 650 nm used in SPAD and wavelength 660 nm used in CCM-200 and that of wavelength 700 nm used in CM-1000 for assessing N in the leaf of in poplar, 'Fuji' apple and almond

| | Plant Species | Visible WL (nm) | R2 | RMSE (%) | Red edge WL (nm) | R2 | RMSE (%) |
|---|---|---|---|---|---|---|---|
| Transmission | Poplar | 585 | 0.9133 | 0.1206 | 703 | 0.9077 | 0.1245 |
| | | 650 | 0.8633 | 0.1515 | 700 | 0.9066 | 0.1252 |
| | | 660 | 0.8414 | 0.1632 | | | |
| | Fuji | 550 | 0.6663 | 0.3871 | 700 | 0.6660 | 0.3873 |
| | | 650 | 0.5889 | 0.4296 | 700 | 0.6660 | 0.3873 |
| | | 660 | 0.5810 | 0.4339 | | | |
| | Almond | 566 | 0.4103 | 0.5800 | 705 | 0.4949 | 0.5367 |
| | | 650 | 0.3097 | 0.6275 | 700 | 0.4748 | 0.5473 |
| | | 660 | 0.2488 | 0.6545 | | | |
| Reflectance | Poplar | 576 | 0.9542 | 0.0877 | 720 | 0.9735 | 0.0667 |
| | | 650 | 0.8040 | 0.1814 | 700 | 0.9332 | 0.1059 |
| | | 660 | 0.7425 | 0.2081 | | | |
| | Fuji | 550 | 0.6117 | 0.4148 | 728 | 0.7057 | 0.3612 |
| | | 650 | 0.0948 | 0.6334 | 700 | 0.6292 | 0.4054 |
| | | 660 | 0.0029 | 0.6648 | | | |
| | Almond | 558 | 0.4963 | 0.5360 | 713 | 0.5028 | 0.5325 |
| | | 650 | 0.3807 | 0.5943 | 700 | 0.4748 | 0.5473 |
| | | 660 | 0.3380 | 0.6144 | | | |

The Variation of Sampling Distance on Meter Accuracy

Constant sampling distance is another important factor to meter accuracy. An increase in sampling distance will decrease light intensity received by the photodiode and result in an over estimation by SPAD-502 and CCM-200 or an underestimation by CM-1000. Contrarily, a decrease in sampling distance will increase light intensity received by the photodiode and result in an underestimation by SPAD-502 and CCM-200 or an over estimation by CM-1000. According to our result, SPAD meter sampling distance is more constant than CCM-200, and therefore more accurate (Table 1-3). CM-1000 recommended target distance by the meter producer is 28.4 to 183 cm. Within this recommended range, the result for the same leaf at different sampling distance should be the same or no significant difference; however our result indicated the different for different sampling distance was significant; moreover, the difference significantly increased with the increase of leaf Chl content (FIG. 25)

Effect of Light Source Constancy and Consistency on Accuracy

In addition to optimum wavelength and constant sampling distance, keeping the light source (LEDs) constant and consistent is also very important to meter accuracy. Inconstant light source or any factor that affects the consistency of light intensity between the reference sensor and sampling sensor will affect meter accuracy. For CM-1000 Chl meter, the ambient light sensor and sample target sensor are not located on the same level but far from each other; thus, it is very easy to cause light intensity inconsistent between ambient light sensors and sample target sensor.

Figure 26:
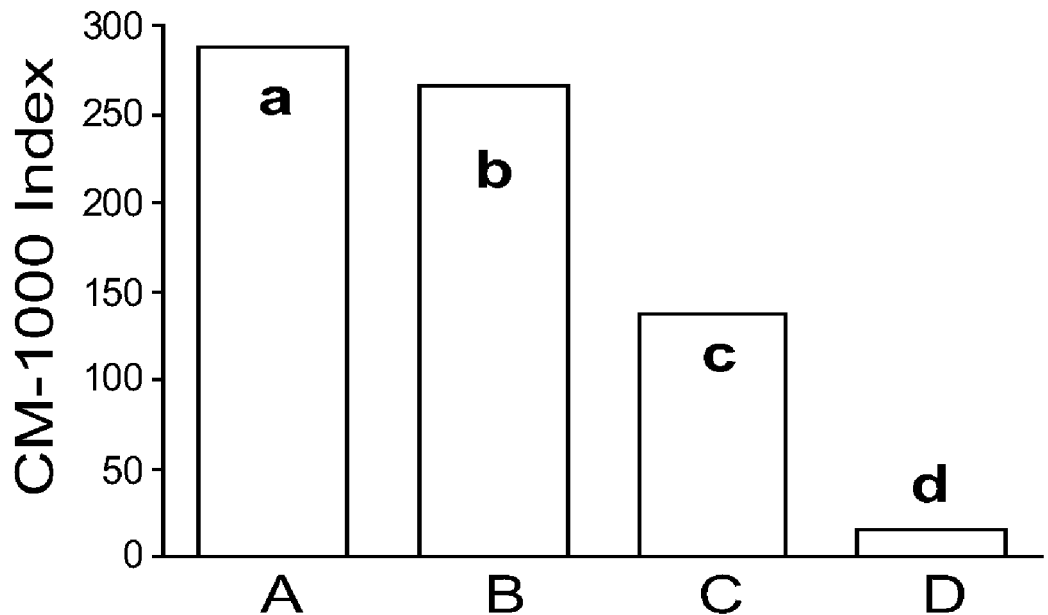
FIG. 26 is a graph of the effect of shading and different light intensity exposure between ambient light sensors and the target sample on the CM-1000 index.
Figure 27:
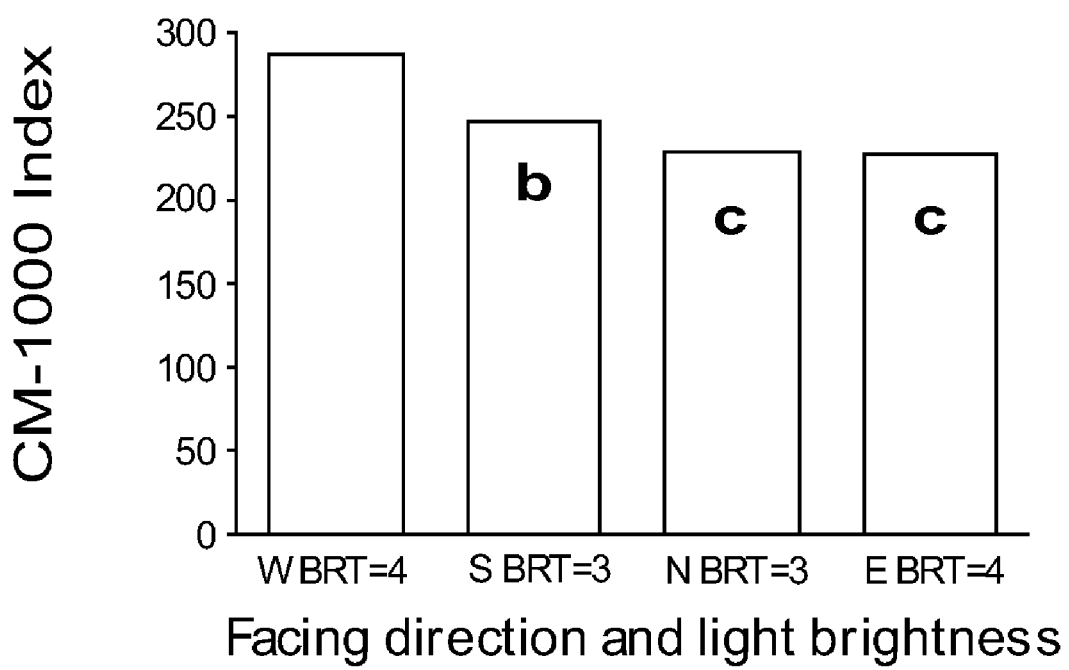
FIG. 27 is a graph of the effect of the direction faced by the user in measuring light brightness (BRT) and CM-1000 index, where "W" denotes facing west (i.e., the sun is at the back of the user), "S" denotes facing south, "N" denotes facing north, and "E" denotes facing east (i.e., the sun is in front of the user).

Compared to both ambient light sensors and target leaf exposed to sunlight, the measurement of ambient light sensors exposure to sunlight while target leaf in the shade, or ambient light sensors in the shade while target leaf exposure to sunlight, or both ambient light sensors and target leaf in the shade significantly decreased CM-1000 meter reading (FIG. 26). Furthermore, the light brightness of ambient sensor and CM-1000 meter reading was significantly affected by user facing direction (FIG. 27). In comparison to CM-1000 that using natural sunlight, both SPAD-502 and CCM-200 use inside LEDs as the light sources, which is much more constant than the natural sun light used by CM-1000 because the intensity of the sunlight varies with the existence of clouds, dust, shading and the time of the day. However the most important reason is that special attention should be paid to keep the sun at the back of the user and keep the ambient light sensors and the target leaf under same light intensity and perpendicular to the sun as the meter producer recommended; however, it is not always easy to do so. Any light intensity difference between the ambient light sensors and the target leaf will result in either an overestimation of an underestimation. On these aspect, SPAD-502 and CCM-200 are more accurate than CM-1000.

Optimum Algorithm Comparison with Hand-Held Meters in Clh and N Assessment

In order to compare the optimum wavelength and algorithm selected by using Li-1800 spectroradiometer with that used in the hand-held Chl meters, the specific wavelength related algorithm, the best fit equation, regression coefficient determination and RMSE of total Chl and N were listed in Table 23 and Table 24. $R^2$ is the essential indicator and a measure of goodness-of-fit of regression. The higher the $R^2$ with a smaller RMSE, the more accurate the regression and the regression related algorithm. Among three hand-held Chl meters SPAD had highest $R^2$ smallest RMSE in measuring Chl and N in 'Fuji' apple, poplar and almond; therefore, it is more accurate than CCM-200 and CM-1000. Under constant sampling distance, the accuracy of CM-1000 was similar to that of CCM-200 (Table 19 and Table 20). However, if we compare the wavelength and the algorithm used by the hand-held Chl meter with the algorithm developed by using the optimum wavelength selected from the whole spectrum, even single optimum wavelength either in green or in red edge alone is more accurate than any of the hand-held meter in measuring both Chl and N. The algorithm of two wavelength simple ratio ($T_{940}/T_{green}$ or $T_{940}/T_{red\ edge}$, $R_{940}/R_{green}$ or $R_{940}/R_{red\ edge}$) or any other superior algorithm with one Chl sensitive optimum wavelength either in green or red edge in combination with one NIR wavelength (i.e., 940 nm) to compensate for leaf texture difference further increased the value of $R^2$ and regression accuracy. If the regression of single wavelength alone already has a higher $R^2$ (i.e., larger than 0.9000 for Chl or larger than 0.6000 for N), the $R^2$ improvement was minor by adding the NIR wavelength. If the regression of single wavelength alone has a relative smaller $R^2$, the improvement was evident by adding the NIR wavelength. Different species has different optimum wavelength, different $R^2$ and RMSE. Fortunately, the optimum wavelength for different species tested fell in two relative narrow wavebands either in the green 540-590 nm or in red edge 700-730 nm (FIGS. 21-24, Tables 21-22 and Tables 23-24).

TABLE 23

Calibration equations for hand-held meters and the optimum wavelength related algorithms in Chl assessment in the leaf of 'Fuji' apple, poplar, and almond

| Plant leaves | Method | Calibration equation to convert index value to Chl content ($\mu g \cdot m^{-2}$) | $R^2$ | RMSE ($\mu g \cdot m^{-2}$) |
|---|---|---|---|---|
| Fuji apple | $T_{650}$ (SPAD) | $y = 0.3434x^2 + 2.3267x - 395.29$ | 0.9078 | 76.64 |
| | $R_{700}$ (CM-1000) | $y = 0.0029x^2 + 11.864x - 1726.2$ | 0.8028 | 119.17 |
| | $T_{660}$ (CCM-200) | $y = 0.0482x^2 + 11.79x - 205.71$ | 0.8232 | 110.91 |
| | $T_{552}$ | $y = 113679x^2 - 23675x + 1551$ | 0.9346 | 65.80 |
| | $T_{712}$ | $y = 14770x^2 - 11497x + 2077$ | 0.9183 | 72.39 |
| | $T_{940}/T_{552}$ | $y = -3.5x^2 + 133.13x - 189.84$ | 0.9563 | 57.00 |
| | $T_{940}/T_{712}$ | $y = -108.37x^2 + 1015.7x - 1242.7$ | 0.9511 | 59.11 |
| | $(T_{940} - T_{552})/(T_{940} + T_{552})$ | $y = 6619.9x^2 - 7209.7x + 2253.1$ | 0.9520 | 58.74 |
| | $(T_{940} - T_{712})/(T_{940} + T_{712})$ | $y = 520.3x^2 + 2328.2x - 474.51$ | 0.9474 | 60.60 |
| | Chl TNDI | $y = 1992.4x^2 + 352.14x - 210.7$ | 0.9476 | 60.52 |
| | TII | $y = -0.9591x^2 + 78.041x - 329.55$ | 0.9478 | 60.44 |
| | $R_{552}$ | $y = 98641x^2 - 37291x + 3848.5$ | 0.8630 | 94.79 |
| | $R_{717}$ | $y = 17199x^2 - 16194x + 4019.4$ | 0.9232 | 70.41 |
| | $R_{940}/R_{552}$ | $y = 32.183x^{2.0208}$ | 0.8935 | 82.43 |
| | $R_{940}/R_{717}$ | $y = 903.78x - 1038.5$ | 0.9451 | 61.54 |
| | $(R_{940} - R_{552})/(R_{940} + R_{552})$ | $y = 11.248e^{6.4587x}$ | 0.8811 | 87.46 |
| | $(R_{940} - R_{717})/(R_{940} + R_{717})$ | $y = 3847.2x - 492.86$ | 0.9433 | 62.26 |
| | Chl RNDI | $y = 5433.6x^{3.1756}$ | 0.9332 | 66.36 |
| | RII | $y = 135.77x + 124.69$ | 0.9542 | 57.85 |
| Poplar | $T_{650}$ (SPAD) | $y = 0.5785x^2 - 17.304x + 317.95$ | 0.9011 | 43.08 |
| | $R_{700}$ (CM-1000) | $y = 0.0844x^2 - 17.472x + 1064.8$ | 0.8623 | 53.83 |
| | $T_{660}$ (CCM-200) | $y = 3.6266x^2 - 137.27x + 1481.8$ | 0.8823 | 48.29 |
| | $T_{580}$ | $y = 35494x^2 - 13473x + 1479.8$ | 0.9222 | 37.23 |
| | $T_{705}$ | $y = 17088x^2 - 11307x + 2058.3$ | 0.9102 | 40.56 |
| | $T_{940}/T_{580}$ | $y = 2.2624x^2 + 116.76x - 108.02$ | 0.9356 | 33.52 |
| | $T_{940}/T_{705}$ | $y = 90.238x^2 - 12.035x + 20.876$ | 0.9477 | 30.16 |
| | $(T_{940} - T_{580})/(T_{940} + T_{580})$ | $y = 3538.8x^2 - 2486.7x + 617.55$ | 0.9338 | 34.02 |
| | $(T_{940} - T_{705})/(T_{940} + T_{705})$ | $y = 3498.3x^2 - 875.93x + 232.1$ | 0.9450 | 30.91 |
| | Chl TNDI | $y = 3923.8x^2 - 785.77x + 214.55$ | 0.9469 | 30.39 |
| | TII | $y = 0.3265x^2 + 3.9039x + 114.22$ | 0.9483 | 30.00 |
| | $R_{575}$ | $y = 36401x^2 - 15256x + 1788.4$ | 0.9420 | 31.74 |
| | $R_{720}$ | $y = 9497.3x^2 - 10926x + 3254.3$ | 0.9447 | 30.99 |
| | $R_{940}/R_{575}$ | $y = 17.295x^2 + 54.943x - 94.561$ | 0.9432 | 31.41 |
| | $R_{940}/R_{720}$ | $y = 778.71x^2 - 966.96x + 297.14$ | 0.9553 | 28.06 |
| | $(R_{940} - R_{575})/(R_{940} + R_{575})$ | $y = 7109.8x^2 - 6014.2x + 1454.2$ | 0.9420 | 31.74 |

TABLE 23-continued

Calibration equations for hand-held meters and the optimum wavelength related algorithms in Chl assessment in the leaf of 'Fuji' apple, poplar, and almond

| Plant leaves | Method | Calibration equation to convert index value to Chl content (μg · m$^{-2}$) | $R^2$ | RMSE (μg · m$^{-2}$) |
|---|---|---|---|---|
| | $(R_{940} - R_{720})/(R_{940} + R_{720})$ | $y = 8551.8x^2 + 624.63x + 129.57$ | 0.9548 | 28.20 |
| | Chl RNDI | $y = 3734.3x^2 - 1092.9x + 258.42$ | 0.9534 | 28.58 |
| | RII | $y = 0.9324x^2 + 13.81x + 102.6$ | 0.9543 | 28.33 |
| Almond | $T_{650}$ (SPAD) | $y = 0.3667x^2 + 7.9957x - 186.79$ | 0.7927 | 65.74 |
| | $R_{700}$ (CM-1000) | $y = 0.0224x^2 + 5.3628x - 767.16$ | 0.6860 | 89.25 |
| | $T_{660}$ (CCM-200) | $y = -0.3663x^2 + 62.204x - 401.02$ | 0.6842 | 89.65 |
| | $T_{567}$ | $y = 34366x^2 - 15480x + 1928.3$ | 0.8235 | 56.23 |
| | $T_{705}$ | $y = 21621x^2 - 14236x + 2508.9$ | 0.8542 | 51.08 |
| | $T_{940}/T_{580}$ | $y = -34.444x^2 + 467.98x - 715.91$ | 0.8937 | 43.48 |
| | $T_{940}/T_{705}$ | $y = -51.679x^2 + 683.67x - 764.67$ | 0.9280 | 35.93 |
| | $(T_{940} - T_{580})/(T_{940} + T_{580})$ | $y = 2736.6x^2 - 713.13x + 48.378$ | 0.8934 | 43.55 |
| | $(T_{940} - T_{705})/(T_{940} + T_{705})$ | $y = 2218.6x - 336.49$ | 0.9202 | 37.64 |
| | Chl TNDI | $y = 2888.7x^2 + 331.25x - 3.8082$ | 0.9267 | 36.21 |
| | TII | $y = 0.0825x^2 + 52.64x - 64.687$ | 0.9319 | 35.07 |
| | $R_{550}$ | $y = 22076x^2 - 14001x + 2437$ | 0.9173 | 38.95 |
| | $R_{710}$ | $y = 15276x^2 - 13438x + 3187.1$ | 0.9184 | 38.72 |
| | $R_{940}/R_{550}$ | $y = 26.283x^2 + 304.13x - 436.97$ | 0.9350 | 34.09 |
| | $R_{940}/R_{710}$ | $y = 259.76x^2 - 48.762x - 144.57$ | 0.9420 | 32.26 |
| | $(R_{940} - R_{550})/(R_{940} + R_{550})$ | $y = 4975.2x^2 - 1546.6x + 237.5$ | 0.9356 | 33.93 |
| | $(R_{940} - R_{710})/(R_{940} + R_{710})$ | $y = 2548.9x - 130.06$ | 0.9268 | 36.24 |
| | Chl RNDI | $y = 4975.2x^2 - 1546.6x + 237.5$ | 0.9356 | 33.93 |
| | RII | $y = 1.8052x^2 + 25.505x + 77.693$ | 0.9373 | 33.49 |

TABLE 24

Calibration equations for hand-held meters and the optimum wavelength related algorithms in N assessment in the leaf of 'Fuji' apple, poplar, and almond

| Plant leaves | Method | Calibration equation to convert index value to N content (%) | $R^2$ | RMSE (%) |
|---|---|---|---|---|
| Fuji apple | SPAD | $y = -0.0002x^2 + 0.1067x - 2.6816$ | 0.6637 | 0.3878 |
| | CM-1000 | $y = 9E-07x^2 + 0.0287x - 3.1969$ | 0.5716 | 0.4372 |
| | CCM-200 | $y = 5E-05x^2 + 0.0333x + 0.2203$ | 0.5736 | 0.4361 |
| | $T_{550}$ | $y = 137.14x^2 - 40.285x + 4.0386$ | 0.6765 | 0.3809 |
| | $T_{700}$ | $y = 12.928x^2 - 24.493x + 4.006$ | 0.6670 | 0.3860 |
| | $T_{940}/T_{550}$ | $y = -0.0133x^2 + 0.4149x - 0.1056$ | 0.7246 | 0.3551 |
| | $T_{940}/T_{700}$ | $y = -0.0396x^2 + 0.7988x - 0.9225$ | 0.7139 | 0.3608 |
| | $(T_{940} - T_{550})/(T_{940} + T_{550})$ | $y = 5.7044x^2 - 2.0416x + 0.5016$ | 0.6890 | 0.3742 |
| | $(T_{940} - T_{700})/(T_{940} + T_{700})$ | $y = -3.6722x^2 + 11.696x - 4.0332$ | 0.6849 | 0.3764 |
| | Chl TNDI | $y = -0.0003x^2 + 0.0525x + 1.3023$ | 0.7634 | 0.3342 |
| | TII | $y = -0.0002x^2 + 0.0569x - 1.0676$ | 0.6985 | 0.3691 |
| | $R_{550}$ | $y = 130x^2 - 39.314x + 4.0084$ | 0.6678 | 0.3856 |
| | $R_{728}$ | $y = -128.35x^2 + 52.19x - 2.1238$ | 0.6142 | 0.4143 |
| | $R_{940}/R_{550}$ | $y = 0.2082x^{1.4485}$ | 0.6533 | 0.3933 |
| | $R_{940}/R_{728}$ | $y = 2.5179x - 1.9029$ | 0.6606 | 0.3894 |
| | $(R_{940} - R_{550})/(R_{940} + R_{550})$ | $y = 0.0684e^{5.1885x}$ | 0.6495 | 0.3954 |
| | $(R_{940} - R_{728})/(R_{940} + R_{728})$ | $y = 9.4441x - 0.0294$ | 0.6776 | 0.3803 |
| | Chl RNDI | $y = 8.9077x^{1.9999}$ | 0.7511 | 0.3408 |
| | RII | $y = 0.5488x + 2.6787$ | 0.6540 | 0.3930 |
| Poplar | SPAD | $y = 0.0015x^2 - 0.0332x + 0.8075$ | 0.8902 | 0.0815 |
| | CM-1000 | $y = 0.0002x^2 - 0.0264x + 1.3505$ | 0.7598 | 0.0819 |
| | CCM-200 | $y = 0.0086x^2 - 0.2914x + 3.0171$ | 0.7703 | 0.0813 |
| | $T_{585}$ | $y = 88.265x^2 - 34.974x + 4.1534$ | 0.9485 | 0.0935 |
| | $T_{703}$ | $y = 47.367x^2 - 30.406x + 5.5399$ | 0.9439 | 0.0982 |
| | $T_{940}/T_{585}$ | $y = -0.0313x^2 + 0.6275x - 0.693$ | 0.9559 | 0.0859 |
| | $T_{940}/T_{703}$ | $y = -0.0087x^2 + 0.9319x - 0.743$ | 0.9654 | 0.0761 |
| | $(T_{940} - T_{585})/(T_{940} + T_{585})$ | $y = 7.0458x^2 - 3.6463x + 0.9637$ | 0.9564 | 0.0854 |
| | $(T_{940} - T_{703})/(T_{940} + T_{703})$ | $y = 7.3202x^2 - 0.7568x + 0.517$ | 0.9665 | 0.0750 |
| | Chl TNDI | $y = 8.2514x^2 - 0.0182x + 0.4463$ | 0.9675 | 0.0739 |
| | TII | $y = 0.0005x^2 + 0.0469x + 0.208$ | 0.9657 | 0.0758 |
| | $R_{575}$ | $y = 69.255x^2 - 34.466x + 4.7395$ | 0.9641 | 0.0774 |
| | $R_{720}$ | $y = 7.9471x^2 - 16.146x + 6.6034$ | 0.9742 | 0.0670 |
| | $R_{940}/R_{575}$ | $y = -0.0286x^2 + 0.7781x - 1.3003$ | 0.9551 | 0.0867 |
| | $R_{940}/R_{720}$ | $y = -0.1519x^2 + 3.7252x - 3.315$ | 0.9691 | 0.0723 |
| | $(R_{940} - R_{575})/(R_{940} + R_{575})$ | $y = 13.472x^2 - 9.1092x + 1.9665$ | 0.9561 | 0.0857 |
| | $(R_{940} - R_{720})/(R_{940} + R_{720})$ | $y = 10.282x^2 + 6.1685x + 0.2891$ | 0.9693 | 0.0721 |
| | Chl RNDI | $y = 8.0031x^2 - 0.8455x + 0.5033$ | 0.9685 | 0.0729 |
| | RII | $y = -0.0003x^2 + 0.1705x + 0.3198$ | 0.9667 | 0.0748 |

TABLE 24-continued

Calibration equations for hand-held meters and the optimum wavelength related algorithms in N assessment in the leaf of 'Fuji' apple, poplar, and almond

| Plant leaves | Method | Calibration equation to convert index value to N content (%) | $R^2$ | RMSE (%) |
|---|---|---|---|---|
| Almond | SPAD | $y = 0.0001x^2 + 0.1217x - 1.8737$ | 0.4206 | 0.5769 |
| | CM-1000 | $y = 2E-06x^2 + 0.0491x - 4.8862$ | 0.3864 | 0.5955 |
| | CCM-200 | $y = -0.0073x^2 + 0.4363x - 2.7337$ | 0.3867 | 0.5953 |
| | $T_{566}$ | $y = 119.26x^{2 - 57.275x + 7.8023}$ | 0.4878 | 0.5406 |
| | $T_{705}$ | $y = 59.169x^2 - 44.679x + 9.0171$ | 0.5039 | 0.5318 |
| | $T_{940}/T_{566}$ | $y = -0.1222x^2 + 1.8328x - 2.5365$ | 0.5040 | 0.5318 |
| | $T_{940}/T_{705}$ | $y = -0.1486x^2 + 2.5877x - 2.6776$ | 0.5190 | 0.5237 |
| | $(T_{940} - T_{566})/(T_{940} + T_{566})$ | $y = 17.37x^2 - 8.9443x + 1.9691$ | 0.5064 | 0.5305 |
| | $(T_{940} - T_{705})/(T_{940} + T_{705})$ | $y = 9.3391x - 1.1749$ | 0.5118 | 0.5276 |
| | Chl TNDI | $y = 20.111x^2 - 3.8469x + 1.0623$ | 0.5278 | 0.5189 |
| | TII | $y = 0.0009x^2 + 0.0807x + 0.0297$ | 0.5236 | 0.5212 |
| | $R_{558}$ | $y = 95.124x^2 - 59.477x + 10.486$ | 0.5243 | 0.5208 |
| | $R_{713}$ | $y = 67.398x^2 - 63.116x + 15.956$ | 0.5314 | 0.5169 |
| | $R_{940}/R_{558}$ | $y = -0.1512x^2 + 2.4254x - 2.8234$ | 0.5341 | 0.5155 |
| | $R_{940}/R_{713}$ | $y = 0.5318x^2 + 2.4898x - 2.6791$ | 0.5439 | 0.5102 |
| | $(R_{940} - R_{558})/(R_{940} + R_{558})$ | $y = 19.522x^2 - 5.9601x + 1.2452$ | 0.5368 | 0.5140 |
| | $(R_{940} - R_{713})/(R_{940} + R_{713})$ | $y = 12.07x - 0.1272$ | 0.5401 | 0.5122 |
| | Chl RNDI | $y = 25.018x^2 - 5.3098x + 1.3054$ | 0.5415 | 0.5115 |
| | RII | $y = 0.0076x^2 + 0.2948x + 0.555$ | 0.5507 | 0.5065 |

Discussion

Comparison of Different Meters or methods for Chl and N Assessment

When light hits a leaf, it can be reflected, scattered or re-emitted as fluorescence from, absorbed by, or transmitted through the leaf (Fukshansky 1981, Kirk 1994, Richardson et al 2002). Because the function of Chl pigments is to absorb quanta of incident light, some researchers hypothesized that instruments, like SPAD-502 and CCM-200, that estimate Chl content by directly measuring the amount of radiation absorbed by the leaf should be able to give better estimates of Chl content than those relying on reflectance measures (Richardson et al 2002). They got the opposite results showing that the relative Chl content was best estimated by reflectance rather than absorbance (Richardson et al 2002). However, the wavelengths they used in the reflectance indices were different from that used in hand-held Chl meters. Moreover, both SPAD-502 (Markwell et al 1995) and CCM-200 actually measure transmission rather than real light leaf adsorption, although both SPAD and CCM-200 producers mentioned the measurement was based on absorbance in owners' manual (Minolta, 1989; OptiScience, 2000). Our result indicated that the $R^2$ and RMSE differed significantly among wavelengths (FIGS. 21-23). With optimum wavelength the indices of transmission and reflectance both had larger $R^2$ and smaller RMSE, and there were no much difference among the indices of transmission and reflectance (FIGS. 21-23, Table 21-24).

Theory and Algorithm Used in Hand-Held Meters

To understand why one hand-held meter is more accurate than another, it is better to know how the meter works, which theory the meter is based on, and what are the main factors affecting meter accuracy. SPAD-502, CCM-200 and CM-1000 Chl meters are all based on spectral analysis by using Chl sensitive wavelength to non-destructively assess Chl content in fresh leaves. The difference is SPAD-502 and CCM-200 using transmission whereas CM-1000 using reflectance.

Both SPAD-502 and CCM-200 have two LEDs to produce red lights with the peak of 650 nm (SPAD-502) or 660 nm (CCM-200) and near infrared (NIR) lights with the peak of 940 nm, respectively. The function of the red wavelength and the NIR wavelength is different. Leaf absorbance and transmission of the red wavelength were sensitive to and changed with leaf Chl content, whereas that of the NIR wavelength were, instead of sensitive to Chl, sensitive to leaf texture. Therefore the wavelength 650 nm or 660 nm can be used to measure leaf Chl while the wavelength 940 nm serves to compensate for leaf texture differences such as tissue thickness (Minolta, 1989; OptiScience, 2000). Measurements with SPAD-502 and CCM-200 are based on leaf light transmission ratio of two wavelengths. However the algorithm used in SPAD-502 for the ratio calculation might be different from that of CCM-200. For SPAD-502, upon initial calibration by closing the sampling head without leaf sample, the built-in microprocessor received the photodiode voltage $V_{650}$ and $V_{940}$ produced by the red and NIR light beams and stores the digital values in the memory. When a leaf is subsequently measured, the microprocessor received the corresponding voltage $V'_{650}$ and $V'_{940}$ produced by the red and NIR lights transmitted through the leaf, and finally output the SPAD reading or index based on the ratio of the voltage produced by each wavelength to the corresponding values stored in the memory. The SAPD reading can be calculated by the algorithm/equation (1), in which we use the transmission related wavelength voltage instead of using current used by Markwell et al (1995).

$$SPAD\ reading = \text{Log}\frac{V'_{940}/V_{940}}{V'_{650}/V_{650}} = \text{Log}\frac{V'_{940} \cdot V_{650}}{V'_{650} \cdot V_{940}} \quad (1)$$

According to the algorithm, a leaf with higher Chl content will absorb more light; therefore, the photodiode will receive less light that transmits through the leaf to produce a lower voltage $V'_{650}$. With a smaller denominator in the equation the meter will finally generate a larger reading. Contrarily, a leaf with lower Chl content will absorb less light; therefore, the photodiode will receive more light that transmits through the leaf to produce a higher voltage $V'_{650}$, and finally the meter will generate a smaller reading.

When light hits on a leaf, light absorption (A), transmission (T), scatteration (S), reflection (R), as well as Chl fluorescence (F) will happen (Kirk 1994). Leaf transmission radiant flux varies with leaf light absorption, reflection, scatteration and Chl fluorescence; all of which will contribute to a decrease in the apparent transmission (Kirk 1994). The attenuation of radiant flux by a leaf will be an additive function of these factors (Markwell et al 1995) and can be calculated as voltage by $V'=V-(V_A+V_S+V_R+V_F)$, in which the voltage parameter of $V_A$, $V_S$, $V_R$ and $V_F$ is related to leaf specific properties. Therefore, theoretically, the algorithm for SPAD can be modified as following.

$$SPAD \text{ reading} = \text{Log} \frac{V_{650} \cdot [V_{940} - (V_A + V_S + V_R + V_F)_{940}]}{V_{940} \cdot [V_{650} - (V_A + V_S + V_R + V_F)_{650}]} \quad (2)$$

CM-1000, instead of internal LEDs, uses outside natural lights at wavelengths of 700 nm and 840 nm to estimate the quantity of Chl in plant leaves (Whaley, 2001). Chl absorbs 700 nm light and, as a result, the reflection of that wavelength from the leaf is reduced compared to the reflected 840 nm light. Light having a wavelength of 840 nm is unaffected by leaf Chl content and serves as a parameter to compensate for leaf physical difference such as the presence of a waxy or hairy leaf surface. The quantity of ambient light (840 nmA and 700 nmA) and the sample reflected light (800 nmS and 700 nmS) at each wavelength is measured and converted into corresponding voltage ($V_{840A}$, $V_{700A}$, $V_{840S}$ and $V_{700S}$) by a digital analog. The Chl index is calculated by equation (3). Similar to SPAD-502, the target sample reflectance voltage ($V_{840S}$ and $V_{700S}$) can be further decomposed into polynomial if bring the absorption, transmission, scatteration, as well as Chl fluorescence into the equation.

$$CM\text{-}1000=(V_{840S}/V_{840A})/(V_{700S}/V_{700A}) \quad (3)$$

The algorithms used by the hand-held Chl meter are based on the assumption that Chl is uniformly distributed within the leaf and light intensity within the leaf is uniform. Moreover, the hypothesis either ignores scatterance, reflectance, and Chl fluorescence when measuring transmission or assumes that light transmittance, absorptance, scatterance, reflectance, and Chl fluorescence are all proportional to leaf Chl content. However, like most biological materials, plant leaves are not perfect optical systems (Vogelmann 1993). The Chl pigments are localized within Chloroplasts, which are not uniformly distributed within the leaf, and different light may pass through microenvironments with different Chl content (Markwell et al 1995). Furthermore, the collimated light is refracted and focused by epidermal cells (Myers et al 1994), light intensity within the leaf is not uniform (Markwell et al 1995). The contribution of Chl fluorescence is about 1 to 3% of the lights absorbed by Chl (Nobel, 1991), whereas individual contributions of absorptance, scatterance and reflectance are difficult to access because the relationships among them are very complex (McClendon and Fukshansky 1990, Vogelmann 1993). If significant amount of scatterance and reflectance occur, and their value cannot be assessed, they may simultaneously decrease the transmission through the leaf (McClendon and Fukshansky 1990) and lead to an overestimation of Chl content by SPAD-502 (Markwell et al 1995).

Factors Affecting Meter Accuracy

From the algorithm of SPAD-502 and CM-1000, it is not difficult to realize any factor rather Chl that affecting the voltage parameter ($V_{650}$, $V_{940}$, $V'_{650}$ or $V'_{940}$) of SPAD-502 or the voltage parameter ($V_{840S}$, $V_{840A}$, $V_{700S}$ or $V_{700A}$) of CM-1000 will influence meter accuracy. The first and most important aspect is whether wavelengths used in the meter are optimum wavelengths used for accessing Chl and N in fresh leaves. Simple linear regression coefficient $R^2$ and RMSE results indicated that neither the wavelength 650 nm used by SPAD-502 nor the wavelength 660 nm used by CCM-200 was the optimum for Chl or N assessment (FIGS. 21-24 and Tables 21 and 22), although these wavelengths are optimum for extracted Chl assessment. Extracted Chl has two absorbance peaks, one in the blue (400-450 nm) the other in red (600-700 nm). In 80% acetone Chl solution, Ch a and Ch b can be measured by using wavelength 663.2 nm and 646.8 nm, respectively, and total Chl is the sum of Ch a and Ch b (Lichtenthaler and Wellburn 1983). Based on the fact that most Chl in plant leaves is in the form of Ch a, thus, total Chl in extracted solution can also be directly measured by using wavelength 650 nm or 660 nm (Lichtenthaler, 1987). This might be the reason why SPAD and CCM-200 use wavelength 650 nm and 660 nm to assess Chl in plant leaf, respectively. However, in fresh non-destructive leaves the optimum wavelength for Chl assessment is very different from that of extracted Chl (Gitelson et al. 2003). In fresh non-destructive leaves, the absorption coefficients of Chl in red range are very high (Lichtenthaler, 1987) and the depth of light penetration into the leaf is very low (Cui et al, 1991, Fukshansky et al 1993, Merzlyak and Gitelson 1995). As a result, even low amount of Chl are sufficient to saturate absorption. When Chl exceeded 150 µg·m$^{-2}$, total absorption reached maximal values, and an increase in Chl content did not cause an increase in total absorption (Gitelson et al. 2003).

Simple linear regression coefficient $R^2$ and RMSE results indicated that wavelengths in green range (540-590 nm) and red edge (700-730 nm) have higher $R^2$ and lowest RMSE for both transmission and reflectance of Chl and N in 'Fuji' apple, poplar and almond (FIGS. 21 and 24). Larger $R^2$ with smaller RMSE indicated that the green and red edge can be used as the optimum wavelength for Chl and N assessment. In the green range (540-590 nm) and in red edge (700-730 nm), specific absorption coefficient of Chl in extract (like acetone) is very low; it does not exceed even 6% of that in the blue and red (Heath 1969, Lichtenthaler 1987); However, non-destructive fresh green leaves absorb more than 80% of incident light in the green and red edge (Gausman and Allen 1973, Gitelson and Merzlyak 1994). In these spectral ranges, depth of light penetration into the leaf was found to be four- to six-fold higher than in the blue and red range (Fukshansky et al. 1993, Merzlyak and Gitelson 1995). Therefore, in the green and red edge, absorption of light is high enough to provide high sensitivity of transmission or reflectance for Chl content assessment (FIGS. 21-24, Tables 21-24). In addition to high sensitivity, Chl light absorption in green and red edge has much larger buffer to avoid saturation for leaf Chl content from 1 to 1200 µg·m$^2$, whereas red light, to avoid saturation, can only be used to assess Chl even less than 150 µg·m$^{-2}$ (Gitelson et al. 2003). In plant leaf, N content is closely related to Chl content. Our result indicated that the spectra in green and red edge that sensitive to Chl can also be used to successfully assess leaf N content (FIG. 21-24, Table 21-24). Different species (i.e., 'Fuji' apple, poplar or almond) has different optimum wavelengths for Chl and/or N assessment (Table 21-24). Fortunately, the difference is relatively small and fell in green range (560±20 nm) and red edge (715±15 nm) two narrow wavebands. Thus it is possible to select one "common" optimum wavelength in green or red edge that is sensitive to Chl in combination with one NIR wavelength from 750-1000 nm that is not sensitive to Chl but sensitive to leaf texture to develop a more accurate meter than the current hand-held meter for assessing Chl and N in the leaf of different species. The red edge position is considered to be highly robust to confounding factors, and has a good signal-to-noise ratio (Adams et al., 1999), although some research has suggested that it may be somewhat sensitive to variation in leaf structure (Gitelson et al., 1996).

In addition to optimum wavelength, superior algorithm is also very important to meter accuracy. Transmission or reflectance with single optimum wavelength alone either in green or in red edge is more accurate than any of the handheld meter in measuring both Chl and N (Tables 21-24 T); however, optimum wavelength if incorporated with one NIR wavelength from 750 to 1000 nm as the form of simple ratio or any other superior algorithm to compensate for leaf texture difference can further increase the value of $R^2$ and regression accuracy (Table 22-23). This is especially important if the $R^2$ of single wavelength is smaller than 0.8000 for Chl or 0.6000 for N.

Besides the effect of wavelength and algorithm on meter accuracy, to keep light source consistent and constant is also very important to meter accuracy. SPAD-502 and CCM-200 use inside LEDs to keep light source constant, which is better than natural sun light used by CM-1000. As to CM-1000, the ambient light sensor and sample target sensor are not located on the same level but far from each other; thus, it is very easy to cause light intensity inconsistent between ambient light sensors and sample target sensor, which, in turn, will make either an overestimation or underestimation (FIGS. 26 and 27). This is one reason that CM-1000 is not as accurate as SPAD-502 and CCM-200. Another reason is the variation of sampling distance. CM-1000 recommended sampling distance by the meter producer is 28.4 to 183 cm. Within this recommended range, the result for the same leaf at different sampling distance should be the same or no significant difference; however our result indicated the different for different sampling distance is significant (FIG. 25). From the algorithms used by SPAD-502 and CM-1000, an increase in sampling distance will decrease light intensity received by the photodiode and result in an overestimation by SPAD-502 and CCM-200 or an underestimation by CM-1000. According to our result, SPAD-502 meter sampling distance is more constant than CCM-200, plus wavelength 650 nm used by SPAD-502 is better wavelength 660 used by CCM-200 resulting in that SPAD-502 is more accurate.

Part VIII

Figure 33B:
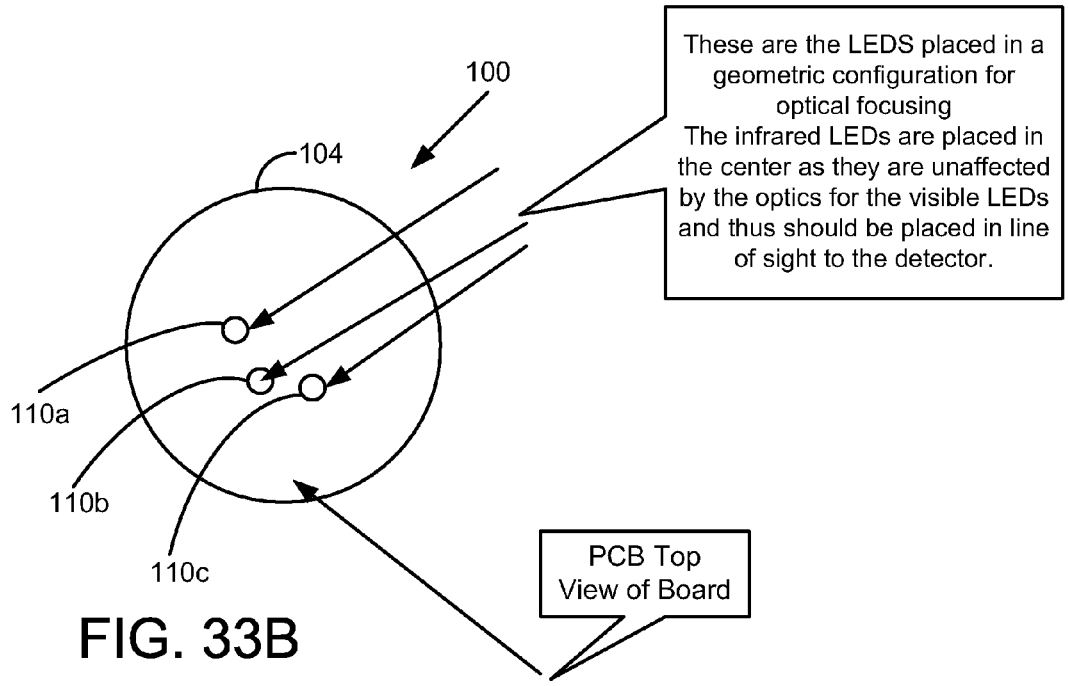
FIG. 33B is a schematic view of the positioning of the LED elements in some embodiments.
Figure 33A:
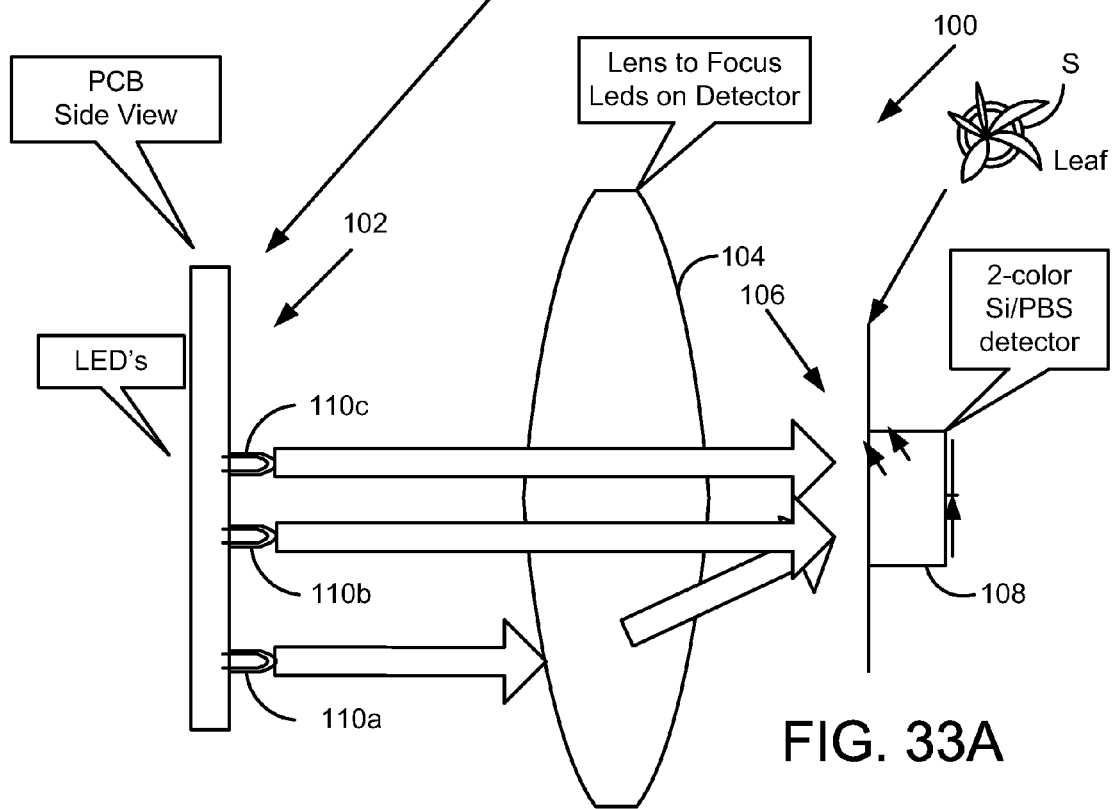
FIG. 33A is a schematic view of a detection portion of a meter or measurement device according to some embodiments.

A representative embodiment of a meter or measurement device 100 is shown schematically in FIGS. 33A and 33B. The measurement device 100 includes a light source 102 capable of producing multiple wavelengths of light and a lens 104 positioned to focus at least some of the light from the light source 102 toward a sample receiving area 106. The sample receiving area 106 is located generally opposite the lens 104 and provides an area where a sample S to be tested can be placed during testing. A photodetector 108 or other light detecting element is positioned adjacent the sample receiving area and senses a response, e.g., the transmittance and/or the reflectance of the sample S when subjected to a selected wavelength of light. One suitable photodetector is a 2-color Si/PBS photodetector, although other types can also be used.

The light source may be comprised of one or more LED elements. In the illustrated example, three LED elements 110a, 110b and 110c are shown. Each LED element may be configured to produce a selected wavelength (or range of wavelengths), or a single element may selectively produce multiple wavelengths.

In FIG. 33A, for example, the LED 110a is configured to produce two wavelength ranges: a first wavelength of about 520 nm to about 580 nm, and a second wavelength of about 690 nm to about 740 nm. The LED 110b is configured to produce a third wavelength of about 800 nm to about 1100 nm. The LED 110c is configured to produce a fourth wavelength of about 1420 nm to about 1510 nm.

FIG. 33B is a schematic depiction of a front view of the lens showing the relative positions of the LED elements 110a, 110b and 110c. The LED element 110c can be positioned nearest the center of the lens because it produces light in the infrared range and is not affected by the operation of the other LED elements. The LED element 110b can be positioned as shown because it produces light in the far-red to near infrared range. The LED element 110a can be positioned farthest from the optical axis to minimize the effects from the other LED elements. Other positioning arrangements are, of course, possible.

Figure 34:
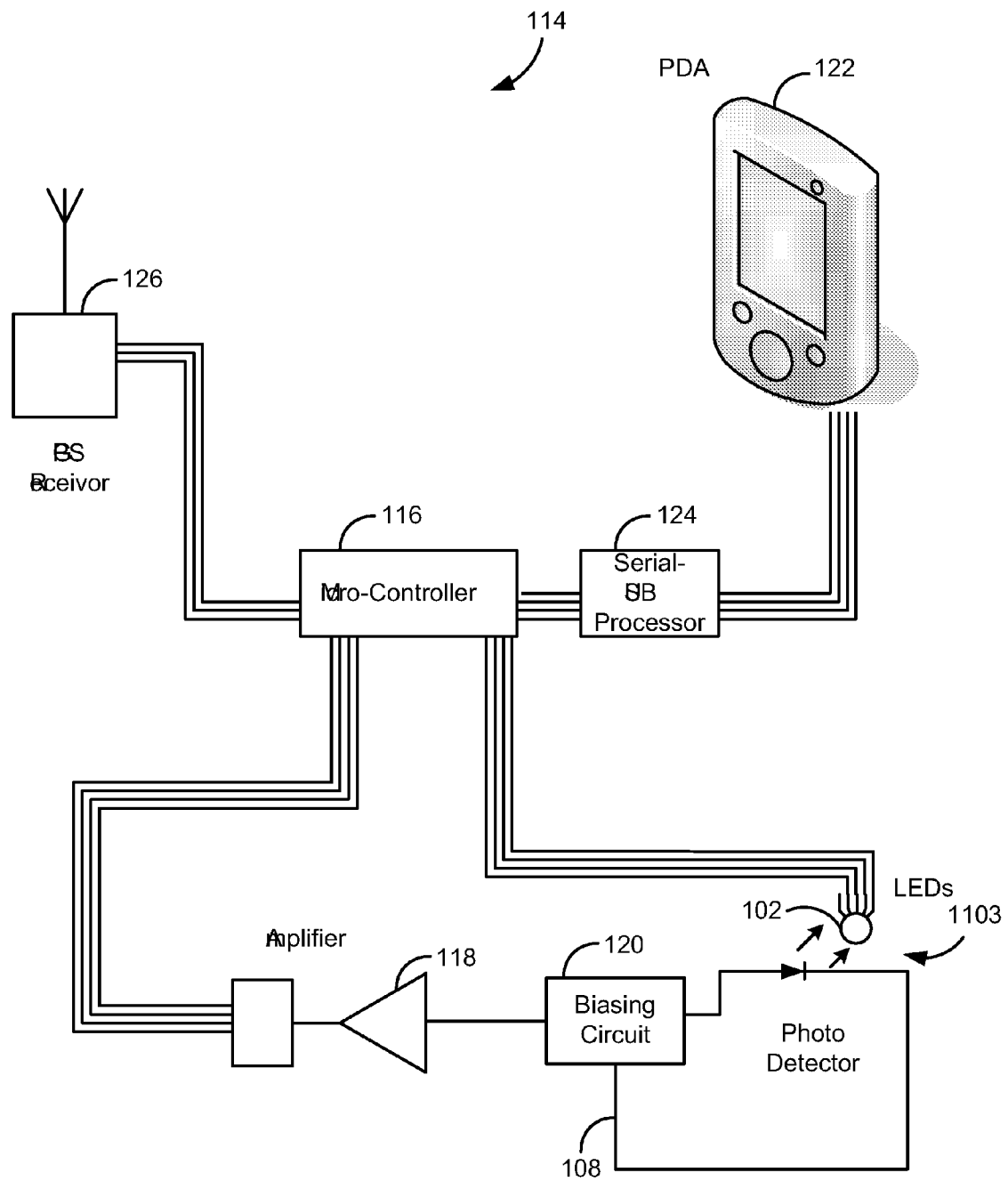
FIG. 34 is a schematic block diagram of the meter or measurement device within a circuit.

FIG. 34 is a schematic block diagram of the device 100 within a circuit 114. The circuit has a microcontroller 116 connected to the photodetector 108 through an amplifier 118 and a biasing circuit 120. The microcontroller 116 is also connected to the light source 102. Thus, the microcontroller 116 controls the light source 102 to emit light at multiple wavelengths, usually in a predetermined sequence, and receives signals from the photodetector indicating the sample's responses to each wavelength.

Figure 30A:
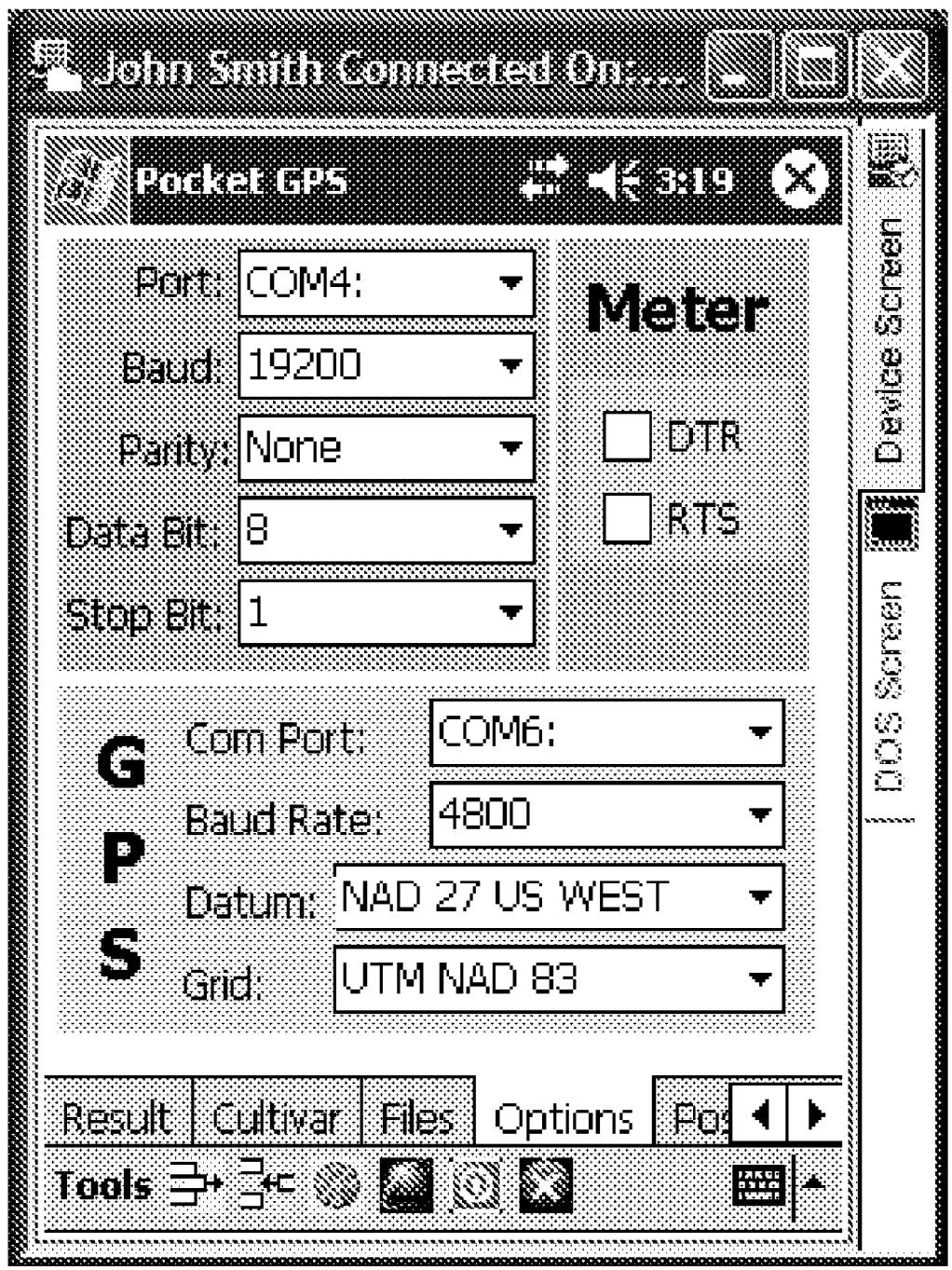
FIGS. 30A-30F are screen shots from an embodiment of a meter or measurement system with a PDA component and integrated GPS functions.
Figure 30B:
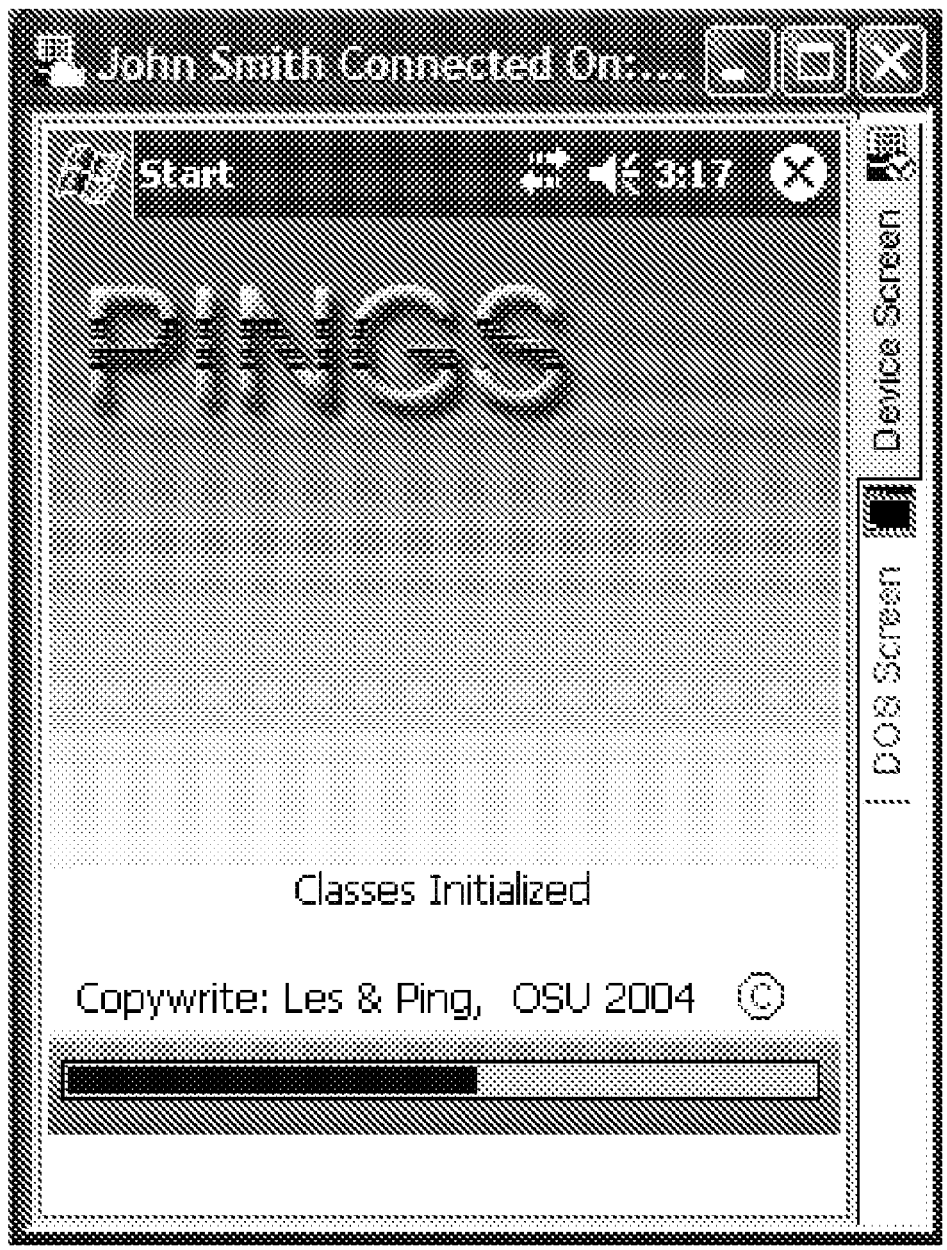
Figure 30C:
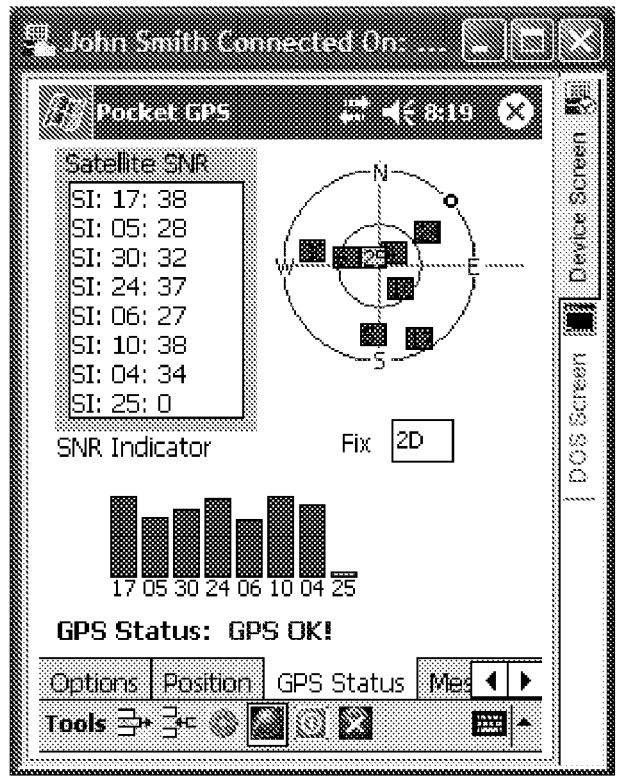
Figure 30D:
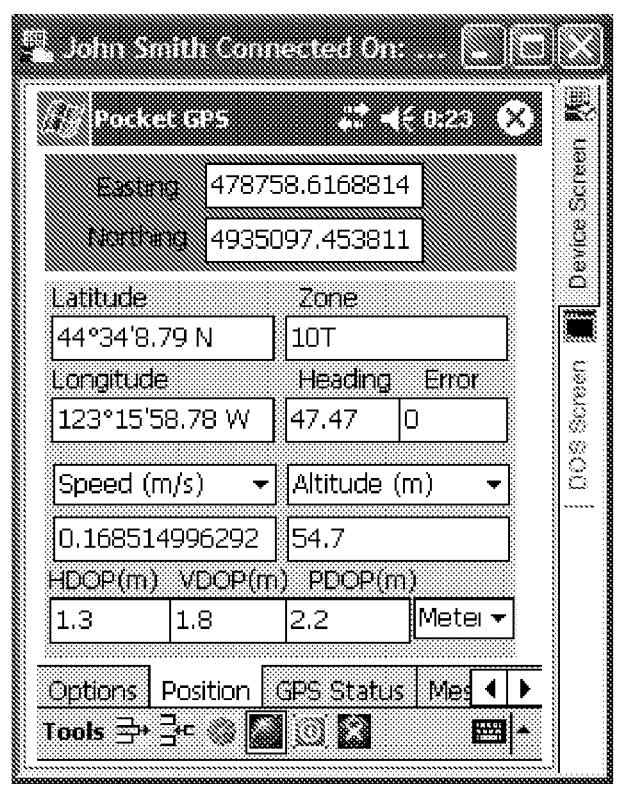
Figure 30E:
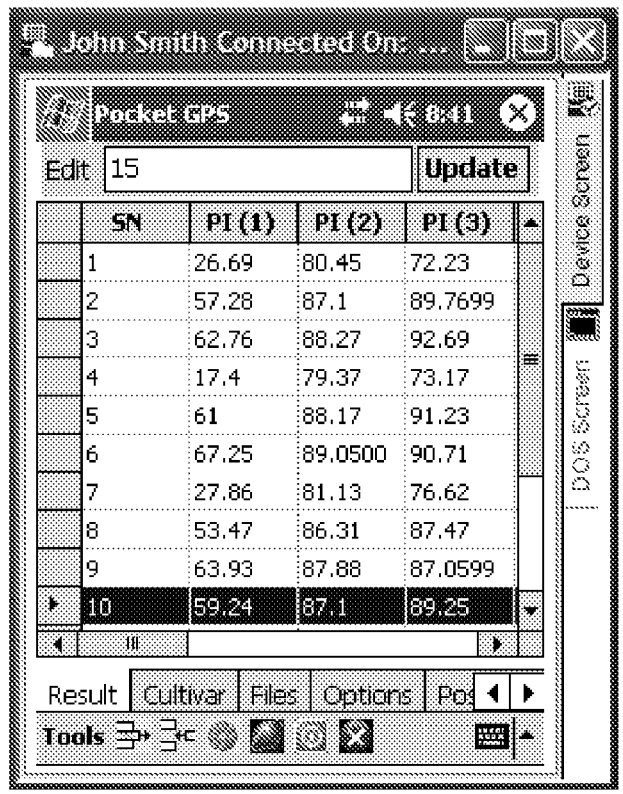
Figure 30F:
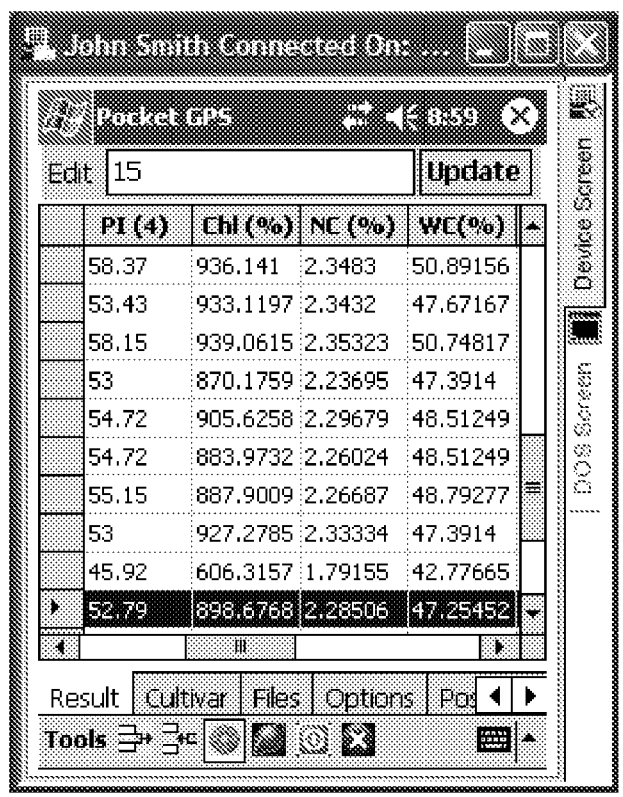

The microcontroller 116 can also be connected to a general purpose PDA (personal digital assistant) 122 or other computing device, such as via a serial-USB processor 124. In this way, the PDA 122 provides a user interface, via its display and controls, with the device 100. Examples of screen shots from a representative user interface are shown in FIGS. 30A to 30F. In FIGS. 30A and 30B, the device 100 is being initialized, including the establishment of an appropriate GPS datum. In FIG. 30C, the current status of the GPS receiver is shown. In FIG. 30D, the current position of the device 100 is shown based on the GPS information. In FIG. 30E, the raw values for a sample being tested with the device 100 are shown. In FIG. 30F, the Chl, N and water content results from the sample, which are directly determined from the raw values using the various algorithms, are shown.

The PDA 122 can be programmed to execute an application for operating the device 100. Some or all of the functions of the microcontroller 116 can be performed by a processor of the PDA 122.

Figure 31A:
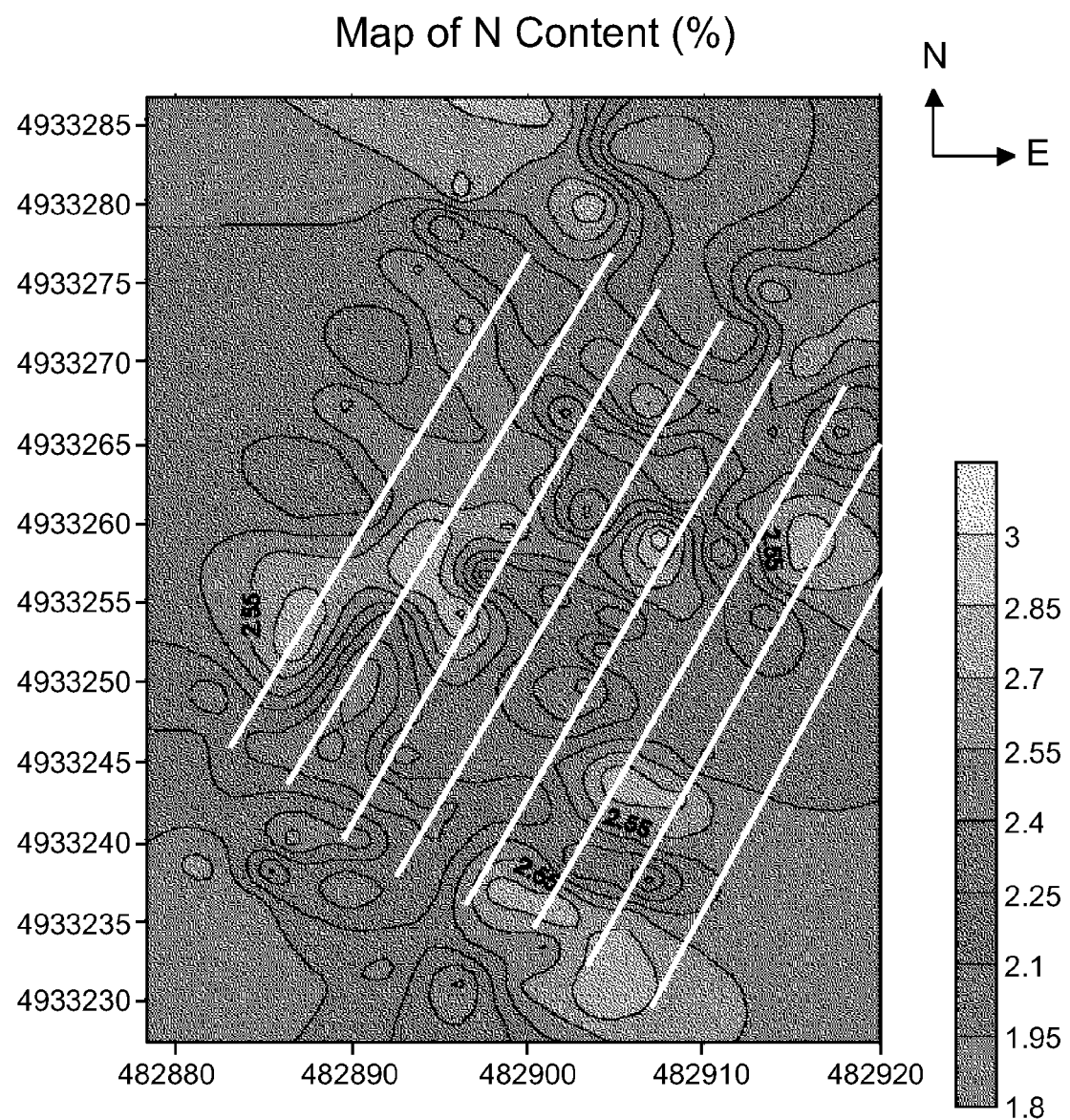
FIGS. 31A and 31B are schematic views of contour maps of a sampling location showing the relative distributions of nitrogen content and chlorophyll content, respectively, that can be generated and displayed with a device having GPS capabilities.
Figure 31B:
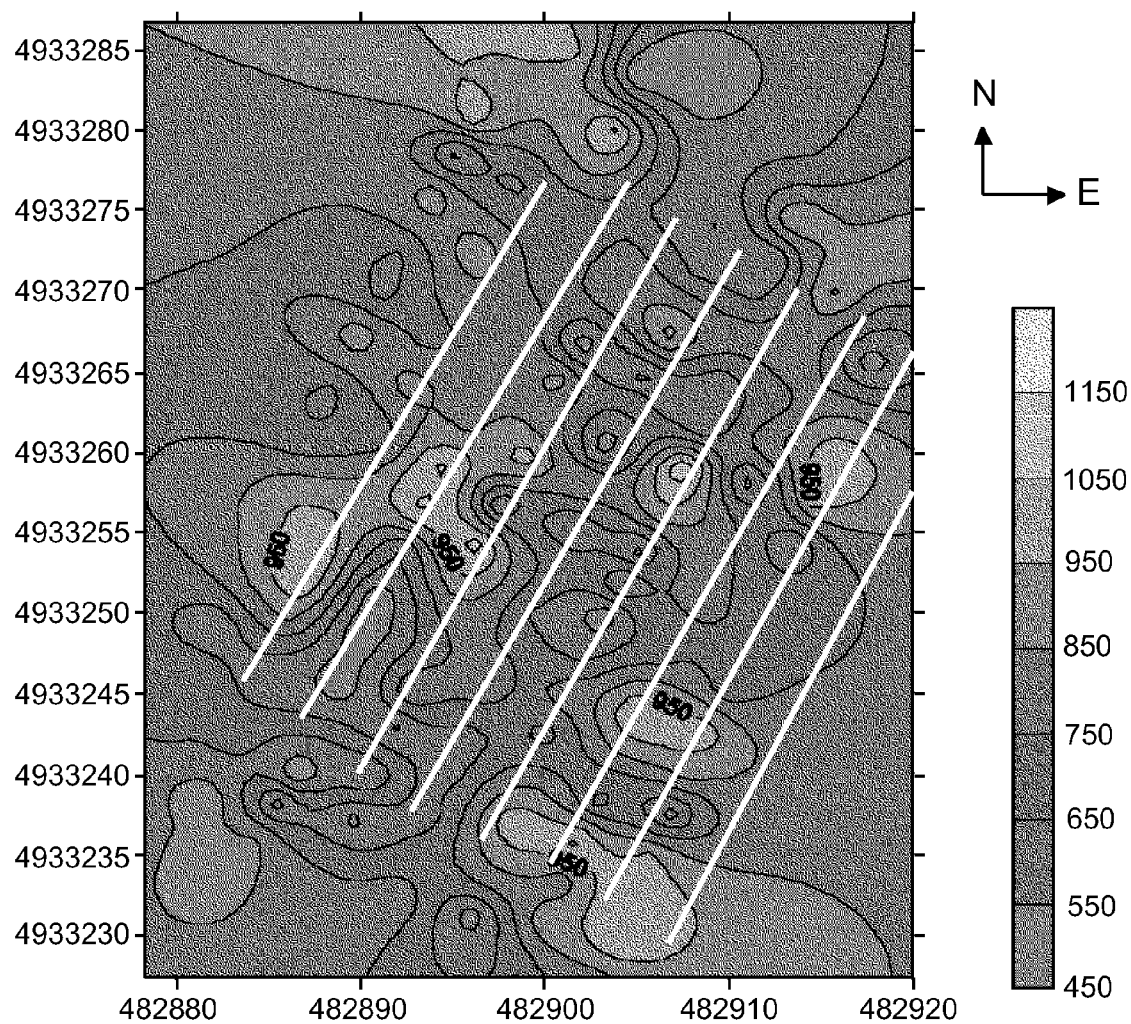
Figure 32:
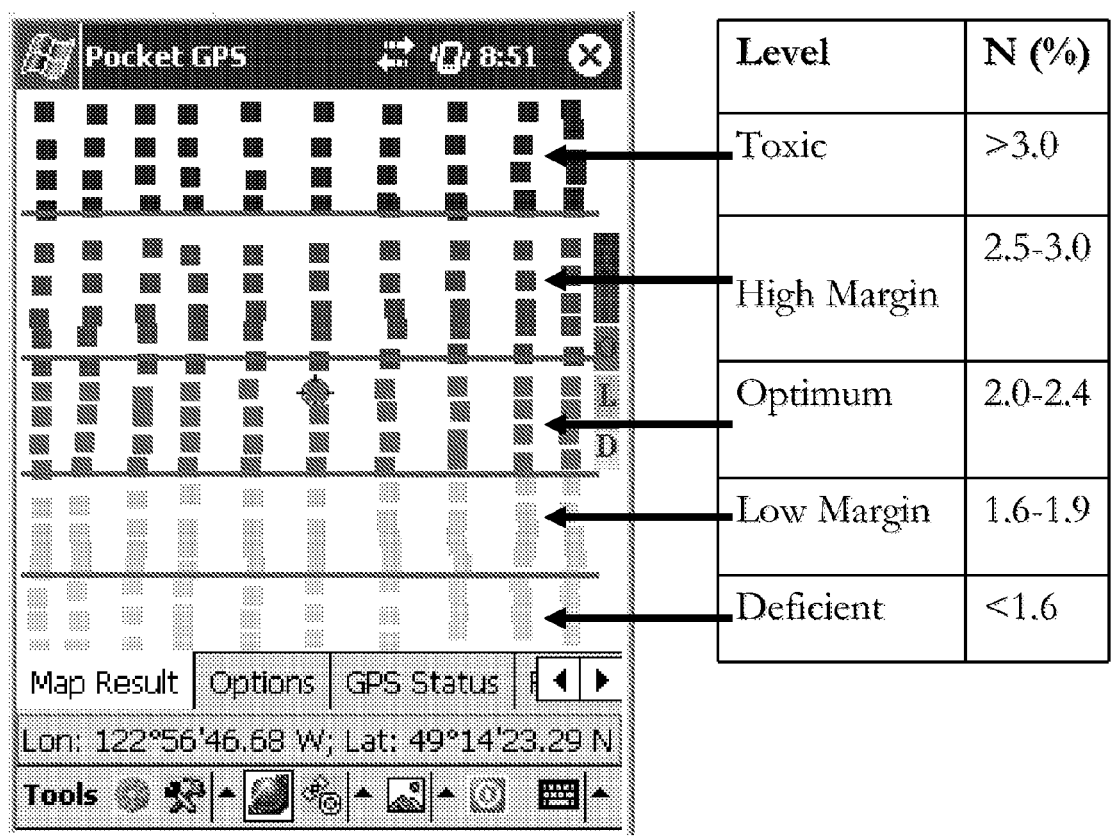
FIG. 32 is a screen shot showing another form of mapping graphics available in a device having GPS capabilities.

Optionally, the system can include a GPS receiver 126 connected to the microcontroller 116. The GPS receiver is operable to provide position information. Conveniently, the system can allow position information to be recorded during the testing of each sample, such as is shown in Table 25. In addition, the PDA 122 can use a mapping application to visually display the positions of the various samples relative to each other, and to indicate one or more of the parameters (e.g., chlorophyll content, nitrogen content, water content, etc.) of each sample for easy recognition and to show trends varying by location (e.g., different results for a shaded hillside). Examples of representative mapping graphics are shown in FIGS. 31A, 31B and 32.

Figure 28:
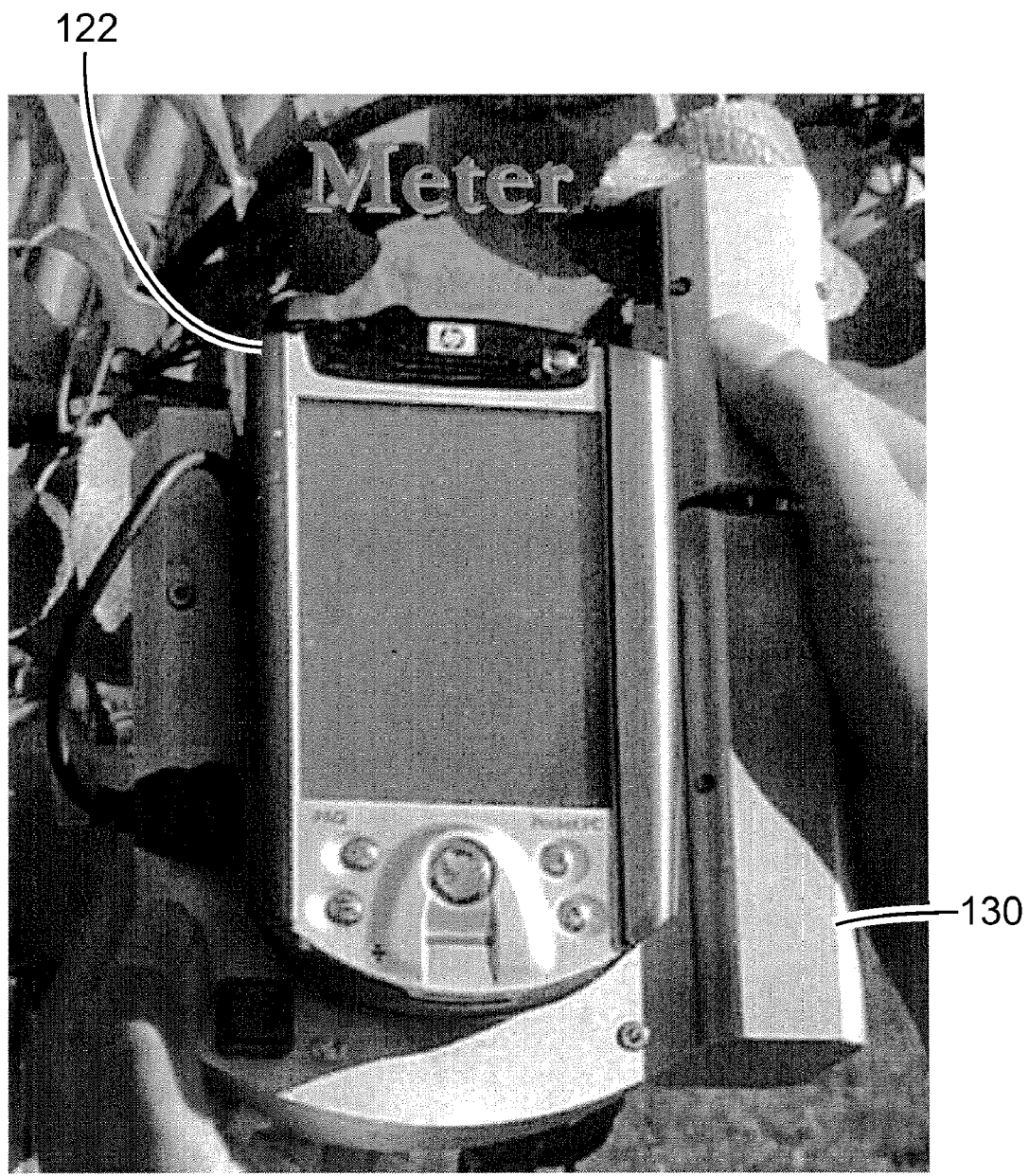
FIG. 28 is a front perspective view of one embodiment of a meter or measurement device with a PDA component.

FIG. 28 shows an exemplary system with a PDA 122 mounted to a body 130. Although not visible in the drawing, the body 130 supports the light source 102, the lens 104 and other components, and defines a sample receiving area. A switch allows the user to activate the system when desired.

Figure 29:
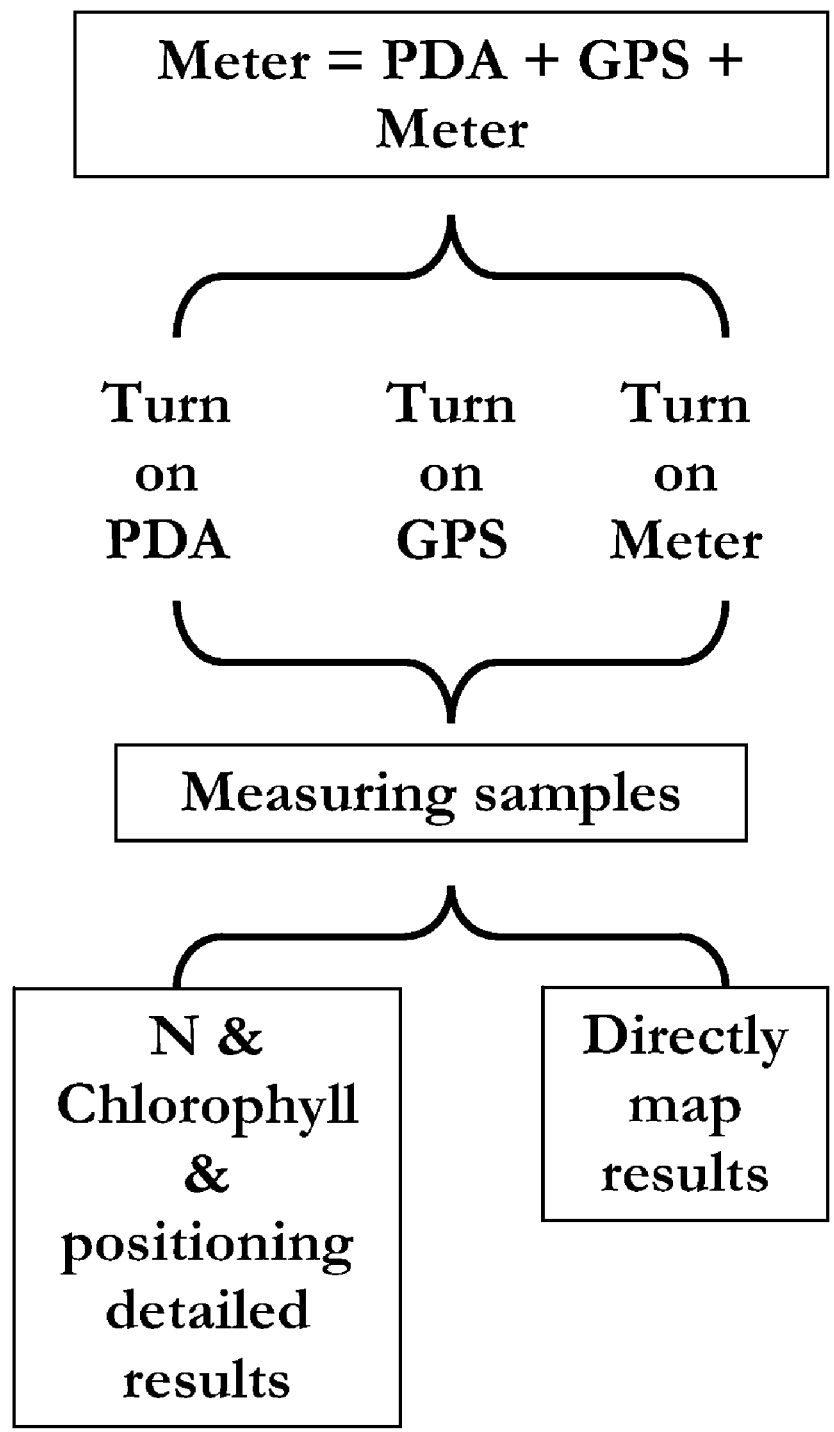
FIG. 29 is a flow chart illustrating major functions of the system.

FIG. 29 is a high-level flowchart showing the major functions of the system.

In view of the many possible embodiments to which the described principles may be applied, it should be recognized that the illustrated embodiments are only preferred examples and should not be taken as limiting in scope. Rather, the scope is defined by the following claims. We therefore claim all that comes within the scope and spirit of these claims.

The invention claimed is:

1. A method for determining chlorophyll content, comprising:
   providing a sample;
   subjecting the sample to light at a first wavelength and detecting a first wavelength response;
   subjecting the sample to light at a second wavelength and detecting a second wavelength response;
   subjecting the sample to light at a third wavelength and detecting a third wavelength response; and
   calculating a chlorophyll content of the sample with a device for determining chlorophyll content based on at least the first wavelength response, the second wavelength response, and the third wavelength response.

2. The method of claim 1, further comprising:
   subjecting the sample to light at a fourth wavelength and detecting a fourth wavelength response,
   wherein calculating a chlorophyll content of the sample is also based on the fourth wavelength response.

3. The method of claim 1, wherein the device for determining chlorophyll content is a handheld device, and wherein subjecting the sample to light at a first wavelength, subjecting the sample to light at a second wavelength, and subjecting the sample to light at a third wavelength are performed with the handheld device.

4. The method of claim 1, wherein subjecting the sample to light at a first wavelength comprises subjecting the sample to light at a wavelength of about 520 nm to about 580 nm.

5. The method of claim 1, wherein subjecting the sample to light at a first wavelength comprises subjecting the sample to light at a wavelength selected to indicate chlorophyll content.

6. The method claim 1, wherein subjecting the sample to light at a second wavelength comprises subjecting the sample to light at a wavelength of about 690 nm to about 740 nm.

7. The method of claim 1, wherein subjecting the sample to light at a second wavelength comprises subjecting the sample to light at a far-red wavelength selected to indicate nitrogen content.

8. The method of claim 1, wherein subjecting the sample to light at a third wavelength comprises subjecting the sample to light at a wavelength of about 800 nm to about 1100 nm.

9. The method of claim 1, wherein subjecting the sample to light at a third wavelength comprises subjecting the sample to light at an infrared wavelength selected to account for at least one of thickness and texture of the sample.

10. The method of claim 2, wherein subjecting the sample to light at a fourth wavelength comprises subjecting the sample to light at a wavelength of about 1420 nm to about 1510 nm.

11. The method of claim 2, wherein subjecting the sample to light at a fourth wavelength comprises subjecting the sample to light at an infrared wavelength selected to indicate water content.

12. The method of claim 1, further comprising storing position information regarding the sample's location.

13. The method of claim 12, wherein storing position information regarding the sample's location comprises storing GPS coordinates representing the sample's location.

14. The method of claim 1, wherein subjecting the sample to light at a first wavelength, subjecting the sample to light at a second wavelength, and subjecting the sample to light at a third wavelength comprises causing light to impinge upon the sample, and wherein detecting a first wavelength response, detecting a second wavelength response and detecting a third wavelength response comprise measuring reflectance from the sample.

15. The method of claim 1, wherein subjecting the sample to light at a first wavelength, subjecting the sample to light at a second wavelength, and subjecting the sample to light at a third wavelength comprises causing light to impinge upon the sample, and wherein detecting a first wavelength response, detecting a second wavelength response and detecting a third wavelength response comprise measuring transmittance from the sample.

16. The method of claim 1, further comprising determining a water content of the sample, and wherein the water content is a factor is calculating a chlorophyll content of the sample.

17. The method of claim 1, further comprising determining the sample's exterior characteristics, and wherein the exterior characteristics are a factor in calculating a chlorophyll content of the sample.

18. A device for determining chlorophyll content, comprising:
   a sample receiving area configured to accommodate a sample during testing;
   a light source positioned adjacent the sample receiving area and operable to subject a sample in the sample receiving area to at least three different wavelengths of light;
   a photodetector operatively arranged adjacent the sample receiving area and configured to detect responses to the at least three different wavelengths of light; and
   a microprocessor connected to the light source and to the photodetector, the microprocessor controlling the light source and the photodetector and calculating a chlorophyll value of a sample based on at least the responses to the at least three different wavelengths of light.

19. The device of claim 18, further comprising a lens positioned to focus light from the light source on a sample in the sample receiving area.

20. The device of claim 18, wherein the device is a handheld device.

21. The device of claim 18, wherein the light source comprises at least one light emitting diode (LED).

22. The device of claim 18, wherein the light source comprises at least one LED capable of generating the at least three different wavelengths of light.

23. The device of claim 18, wherein the light source is capable of generating light at four different wavelengths, including a first wavelength of about 520 nm to about 580 nm, a second wavelength of about 690 nm to about 740 nm, a third wavelength of about 800 nm to about 1100 nm and a fourth wavelength of about 1420 nm to about 1510 nm.

24. The device of claim 18, further comprising a lens positioned between the light source and the sample receiving area, the lens defining an optical axis extending towards the sample receiving area, wherein the light source comprises multiple LED elements, and wherein an LED element capable of generating light at the first wavelength is spaced farther from the optical axis than an LED element capable of generating light at a third wavelength.

25. The device of claim 21, wherein the photodetector is capable of sensing light at the first wavelength, at the second wavelength and at the third wavelength.

26. The device of claim 18, wherein the photodetector comprises a Si/PBS photodetector.

27. The device of claim 18, further comprising a GPS receiver connected to the microprocessor, the GPS receiver being capable of determining a current position.

28. The device of claim 21, further comprising a personal digital assistant connected to the microprocessor, the personal digital assistant having a display, an input device and a memory in which a program for interacting with the device is stored, the display and input device being used to control the operation of the device.

29. The device of claim 28, further comprising a GPS receiver connected to the microprocessor, and wherein the personal digital assistant is operable to display selected position information relative to a background map.

30. The device of claim 18, further comprising a biasing circuit and an amplifier.

31. The device of claim 18, wherein the device is portable and includes a source of DC power.

32. The device of claim 18, wherein the device determines chlorophyll content without harming the sample.

33. The method of claim 1, wherein calculating the chlorophyll content comprises:
obtaining a baseline transmittance value for each wavelength of light to which the sample is subjected;
obtaining a measured transmittance value for each wavelength of light; and
computing at least one index based on the measured transmittance values and the actual transmittance values.

34. The method of claim 33, further comprising computing a polynomial equation based on the at least one index.

35. The method of claim 34, wherein the polynomial equation is a quadratic equation.

36. The method of claim 33, further comprising computing an exponential equation in which the exponent is the index.

37. The method of claim 33, further comprising computing a power equation in which the index is raised to a power.

38. The method of claim 33, further comprising comparing the at least one index to corresponding stored values for a particular plant, and outputting a result.

39. The method of claim 38, wherein the stored values are for a particular plant variety.

40. The method of claim 33, wherein the baseline and measured transmittance values are directly proportional to voltage values.

41. The method of claim 33, wherein a first transmittance ratio is equal to the measured transmittance at the first wavelength divided by the baseline transmittance at the first wavelength,
wherein a third transmittance ratio is equal to the measured transmittance at the third wavelength divided by the baseline transmittance at the third wavelength, and
wherein computing at least one index includes computing a first index equal to the third transmittance ratio divided by the first transmittance ratio.

42. The method of claim 41, wherein a second transmittance ratio is equal to the measured transmittance at the second wavelength divided by the baseline transmittance at the second wavelength, and
wherein computing at least one index includes computing a second index equal to the third transmittance ratio divided by the second transmittance ratio.

43. The method of claim 41, wherein computing at least one index includes computing a third index equal to a quotient of the third transmittance ratio minus the first transmittance ratio divided by the third transmittance ratio plus the first transmittance ratio.

44. The method of claim 41, wherein computing at least one index includes computing a fourth index equal to a quotient of the third transmittance ratio minus the second transmittance ratio divided by the third transmittance ratio plus the second transmittance ratio.

45. The method of claim 33, wherein the at least one index is a first index, and multiple indices are computed, further comprising comparing each of the multiple indices to corresponding stored values, selecting one of the indices based on a predetermined criterion, and outputting results based on the selected one of the indices.

46. A method for determining chlorophyll content, comprising:
providing a sample;
subjecting the sample to light at multiple different wavelengths;
detecting a response for each of the different wavelengths;
determining a water content of the sample;
calculating a chlorophyll content of the sample with a device for determining chlorophyll content based on the response for each of the different wavelengths and the determined water content of the sample.

47. The method of claim 46, wherein calculating chlorophyll content of the sample with a device for determining chlorophyll content comprises using the determined water content of the sample to address any confounding factor based on the sample's water content in the response for each of the different chlorophyll-determining wavelengths.

48. The device of claim 28, wherein the personal digital assistant is connected to the microprocessor via a wireless connection.

49. The method of claim 1, wherein one of the first wavelength, second wavelength and third wavelength is in a red edge portion of the light spectrum.

50. The method of claim 1, wherein one of the first wavelength, the second wavelength and the third wavelength is in a range of about 800 nm to about 1100 nm, and wherein the response to the about 800 nm to about 1100 nm wavelength is used in calculating a chlorophyll content of the sample and in calculating a water content of the sample.

* * * * *